United States Patent
Zhang et al.

(10) Patent No.: US 12,269,810 B2
(45) Date of Patent: Apr. 8, 2025

(54) METHODS OF PREPARING SYNTHETIC CANNABICHROMENE AND CANNABICITRAN AND DERIVATIVES THEREOF

(71) Applicant: Purisys, LLC, Athens, GA (US)

(72) Inventors: Wen-Chun Zhang, Bogart, GA (US); Aaron P Honeycutt, Loganville, GA (US)

(73) Assignee: PURISYS, LLC, Athens, GA (US)

( * ) Notice: Subject to any disclaimer, the term of this patent is extended or adjusted under 35 U.S.C. 154(b) by 79 days.

(21) Appl. No.: 17/997,597

(22) PCT Filed: Apr. 29, 2021

(86) PCT No.: PCT/US2021/029952
§ 371 (c)(1),
(2) Date: Oct. 31, 2022

(87) PCT Pub. No.: WO2021/222609
PCT Pub. Date: Nov. 4, 2021

(65) Prior Publication Data
US 2023/0219916 A1    Jul. 13, 2023

Related U.S. Application Data

(60) Provisional application No. 63/019,063, filed on May 1, 2020.

(51) Int. Cl.
C07D 311/70    (2006.01)
C07D 493/04    (2006.01)
C07D 493/08    (2006.01)

(52) U.S. Cl.
CPC .......... C07D 311/70 (2013.01); C07D 493/04 (2013.01); C07D 493/08 (2013.01)

(58) Field of Classification Search
CPC ... C07D 311/70; C07D 493/04; C07D 493/08
USPC ........................................................ 549/384
See application file for complete search history.

(56) References Cited

U.S. PATENT DOCUMENTS 4,315,862 A    2/1982    Elsohly et al.

FOREIGN PATENT DOCUMENTS

| WO | WO 2021/127786 A1 | 7/2021 |
|----|-------------------|--------|
| WO | WO 2021/127787 A1 | 7/2021 |
| WO | WO 2021/133989 A1 | 7/2021 |

OTHER PUBLICATIONS

Caprioglio et al., "One-Pot Total Synthesis of Cannabinol via Iodine-Mediated Deconstructive Annulation," Organic Letters, 21(15):6122-6125, (Aug. 2, 2019).
Hanuš et al., "Phytocannabinoids: a unified critical inventory," Nat. Prod. Rep., 33:1357-1392, (2016).
Pollastro et al., "Cannabichromene," Natural Product Communications, 13(9):1189-1994, (Feb. 2, 2019).
WIPO Application No. PCT/US2021/029952, PCT International Preliminary Report on Patentability mailed Nov. 10, 2022.
WIPO Application No. PCT/US2021/29952, PCT International Search Report and Written Opinion of the International Searching Authority mailed Aug. 18, 2021.

*Primary Examiner* — Kristin A Vajda
(74) *Attorney, Agent, or Firm* — Alston & Bird LLP

(57) ABSTRACT

The present disclosure relates to the preparation of synthetic cannabinoid derivatives of Formulae I and II, and compositions made therefrom.

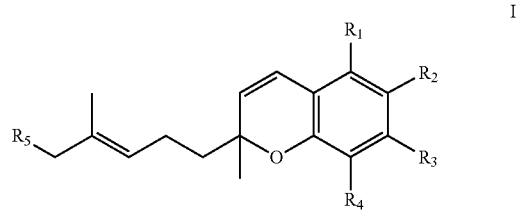
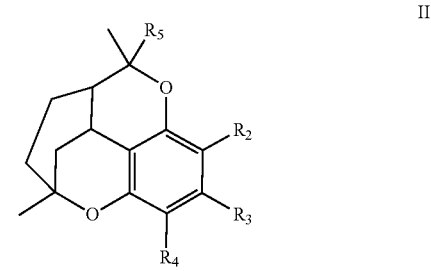

24 Claims, 34 Drawing Sheets

METHODS OF PREPARING SYNTHETIC CANNABICHROMENE AND CANNABICITRAN AND DERIVATIVES THEREOF

CROSS-REFERENCE TO RELATED APPLICATIONS

This application is a 35 U.S.C. § 371 national stage of International Application No. PCT/US2021/029952, filed Apr. 29, 2021, which claims the benefit of and priority to U.S. Provisional Application No. 63/019,063, filed on May 1, 2020, the contents of each of which are hereby incorporated by reference in their entirety.

FIELD

The subject matter described herein relates to methods for preparing synthetic cannabichromene and cannabicitran and derivatives and compositions thereof.

BACKGROUND

Cannabinoids make up a class of diverse chemical compounds that act on cannabinoid receptors in the brain. Ligands for these receptor proteins include the endocannabinoids produced naturally in the body by animals. Plants also produce cannabinoids, sometimes referred to as phytocannabinoids. Over 100 different cannabinoids have been isolated from *cannabis*.

The compound, 2-methyl-2(4-methyl-pent-3-enyl)-5-hydroxy-7-pentylchromene or cannabichromene (CBC) occurs naturally as a cannabinoid constituent of *cannabis*. It is non-psychoactive. Cannabichromene and its disclosed homologues have been found to be effective as anti-inflammatory agents in mammals, and can be used to reduce inflammation and to relieve pain in diseases such as arthritis, as well as to reduce and control edema. Cannabichromene has also been found to be effective in inducing hypothermia which is useful, for example, when a decrease in metabolic activity is desired. It has also shown anti-tumor properties in a breast cancer model.

The compound, (6AR,9R,10AS)-6,6,9-Trimethyl-3-pentyl-6A,7,8,9,10,10A-hexahydro-6H-1,9-epoxybenzo[C] chromene or cannabicitran (CBT) occurs naturally as a cannabinoid constituent of *cannabis*. Compared to major cannabinoids found in the *cannabis* plant, cannabicitran is found in relatively low concentrations. Therefore, it is considered a minor cannabinoid. However, it may contribute to the entourage effect seen in *cannabis* compounds. Its use as a pharmaceutical agent in mammals is less studied. There are reports that it may be useful to lower intraocular pressure.

Given that CBC and CBT are useful compounds that are sourced mostly from plant, and in the case of CBT is found naturally in only low concentrations, what is needed are new synthetic methods to prepare CBC and CBT, and derivatives thereof. The subject matter disclosed herein addresses these shortcomings of the art.

BRIEF SUMMARY

In certain aspects, the subject matter described herein is directed to methods of preparing a compound of Formula I or II,

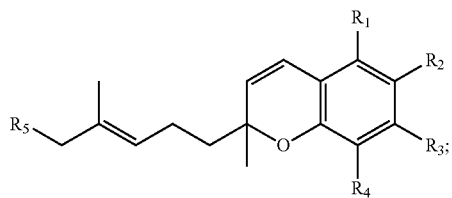

I

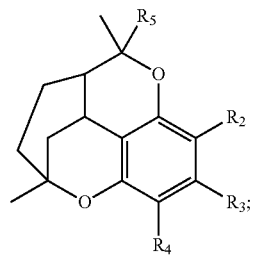

II wherein,
  $R_1$ is selected from the group consisting of hydroxyl and $C_{1-5}$alkoxy;
  $R_2$ and $R_4$ are in each instance independently selected from the group consisting of hydrogen, —$C_{1-5}$alkyl, —$CF_3$, cyano, nitro, phenyl, —$C(O)R_6$, —$NR_aR_b$, —$C(O)OR_6$, —O—$C(O)R_6$, —O—$R_6$, —O—$R_6$, —$C(H)$=$C(R_6)_2$, —$N(H)C(O)R_6$, halo, —$N(R_6)_3$;
    wherein, $R_a$ and $R_b$ are each independently hydrogen or $C_{1-5}$alkyl;
    wherein, $R_6$ is hydrogen or $C_{1-5}$alkyl;
  $R_3$ is selected from the group consisting of hydrogen, linear or branched $C_{1-10}$alkyl;
  $R_5$ is selected from the group consisting of hydrogen, $C_{1-5}$alkyl, $C_{1-5}$alkenyl and prenyl;
comprising:
  dosing at a first temperature above 65° C. a compound of Formula Ia

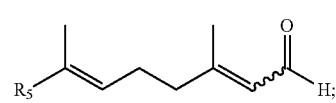

Ia wherein, $R_5$ is as described above;
to a first mixture, said first mixture comprising an amine and a compound of Formula Ib

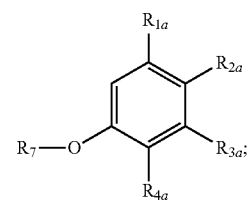

Ib wherein,
  $R_{1a}$ is selected from the group consisting of hydrogen, hydroxyl and $C_{1-5}$alkoxy;
  $R_{2a}$ and $R_{4a}$ are each as described above for $R_2$ and $R_4$;

R$_{3a}$ is selected from the group consisting of hydrogen, linear or branched C$_{1-10}$alkyl; and R$_7$ is selected from the group consisting of hydrogen, —C(O)R$_c$, wherein R$_c$ is hydrogen or C$_{1-5}$alkyl;

to form a second mixture; and, allowing the second mixture to react at a second temperature;

wherein, a compound of Formula I or II is prepared.

In certain aspects, the methods above are directed to preparing a compound of Formula I, which is cannabichromene (CBC).

In certain aspects, the methods above are directed to preparing a compound of Formula II, which is cannabicitran (CBT).

These and other aspects are described fully herein.

DETAILED DESCRIPTION

Figure 1:
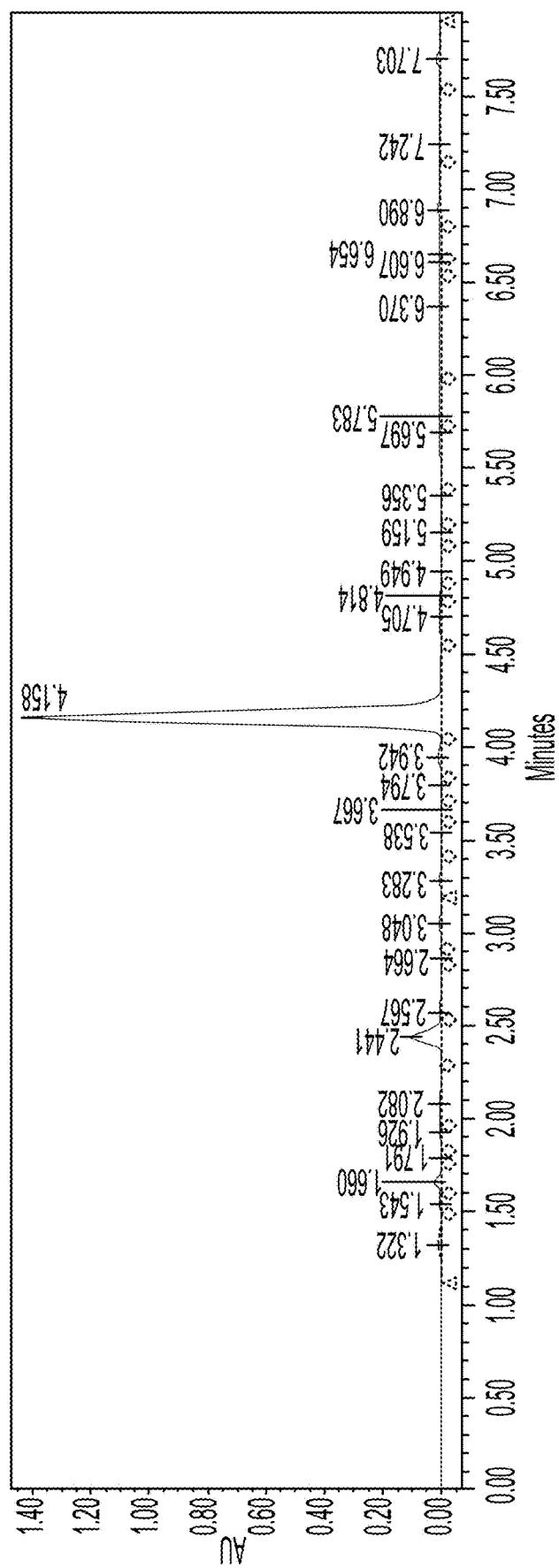
FIG. 1 depicts a HPLC chromatogram of the CBC reaction as described in Example 1.

Disclosed herein are novel synthetic routes for the preparation of compounds of Formulae I and II, such as cannabichromene and cannabicitran, respectively. The compounds are of the general Formula I or II,

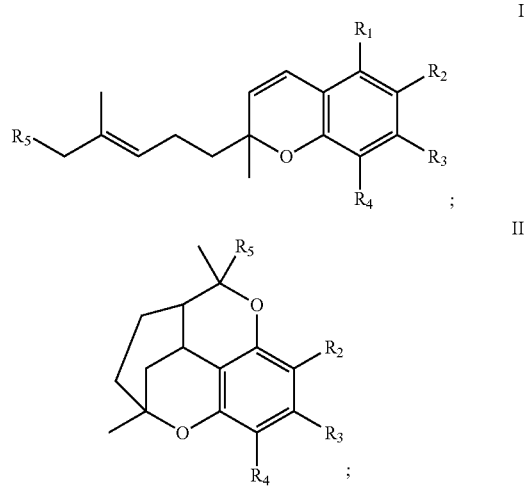

wherein,

R$_1$ is selected from the group consisting of hydroxyl and C$_{1-5}$alkoxy;

R$_2$ and R$_4$ are in each instance independently selected from the group consisting of hydrogen, —C$_{1-5}$alkyl, —CF$_3$, cyano, nitro, phenyl, —C(O)R$_6$, —NR$_a$R$_b$, —C(O)OR$_6$, —O—C(O)R$_6$, —O—R$_6$, —O—R$_6$, —C(H)=C(R$_6$)$_2$, —N(H)C(O)R$_6$, halo, —N(R$_6$)$_3$;

wherein, R$_a$ and R$_b$ are each independently hydrogen or C$_{1-5}$alkyl;

wherein, R$_6$ is hydrogen or C$_{1-5}$alkyl;

R$_3$ is selected from the group consisting of hydrogen, linear or branched C$_{1-10}$alkyl;

R$_5$ is selected from the group consisting of hydrogen, C$_{1-5}$alkyl, C$_{1-5}$alkenyl and prenyl.

These compounds of Formulae I and II are useful cannabinoids but are not readily obtainable by synthetic methods in significant quantity and/or purity. The synthesis of CBC according to literature methods (especially at large scales) was found to be very challenging. Art methods have been shown to yield 60-60%, whereas the methods described herein have been shown to yield over 80%, and repeatedly yield about 90%, of a relatively pure product. The challenges related to the art methods are also in part because significant purifications (e.g. multiple flash column chromatography) were required to remove numerous large impurities formed in the reaction. Upon further investigation, disclosed herein are new approaches for the synthesis of CBC. In an aspect, an improvement for the syntheses was achieved by dosing the citral/toluene solution into the heated reaction mixture (e.g. 90-110° C.) of olivetol, amine, and toluene solvent. Comparing to the conversion methods where all reagents are added altogether and heated to reflux, the improved synthesis is surprisingly clean and requires minimal purification, e.g., to remove any remaining amine, to afford CBC in pure form. We have also proven that the product can be distilled under vacuum to avoid labor intensive column purification and to make it feasible to scale up the process in kilo quantities.

If it is desired to prepare CBT or derivatives thereof, i.e., compounds of Formula II, it has been surprisingly discovered that a distillation process can prepare CBT from CBC in near quantitative yields. This provides a route to these valuable compounds and further evidences the utility of the methods described herein.

Comparing to the art conversion methods where all reagents are added altogether, or dosed and heated to reflux, the improved synthesis is unexpectedly clean and requires minimal purification to afford compounds of interest in pure form. The art routes have shown less than 60% conversion, long reflux periods and vigorous purification strategies leading to low yields less than 50% and purity of no more than 97%. The method described herein, have been shown to achieve a clean reaction, e.g. >80% conversion, by in process IPLC analysis. Final product after single column or after distillation has been isolated in excellent yields >75% with excellent >99% purity.

The methods described herein include a dosing step at elevated temperatures. While not being bound to theory, a rationale that developed over the investigations is that dosing the citral/solution to hot solution (e.g., 90-110° C.) prevents citral from decomposing before reacting with olivetol. This modification has been shown to provide a clean reaction, e.g. >80% conversion, by IPC HPLC. This is not intuitive since the decomposition could also increase at higher temperatures. While in a literature process (U.S. Pat. No. 4,315,862), a slow addition of citral has also been reported but at much lower temperature (i.e. 50-60° C.). In this literature method, the reaction was required to be kept for an additional 9 hours at reflux, leading to the formation of many large impurities. As described elsewhere herein, using a literature method the reaction yield is around only 59%.

Also it has been discovered that the methods described herein achieve a significantly high level of conversion, determined by way of in-process control ("IPC"), where IPC of a certain percentage that is not achievable by art methods leads to an improved process. Once the reaction IPC has reached these levels, the reaction is allowed to proceed to prepare compounds of Formula I or II, depending on which path is chosen.

This rate of conversion has been substantially improved upon by the methods described herein. Consistent high conversions of olivetol to cannabinoids, such as CBC and CBT with minimal impurity formation have been observed. The data disclosed herein shows substantially greater conversion and cleaner reactivity than using reported literature methods. Also advantageously, the methods involve the same upstream chemical pathway to prepare compounds of Formulae I and II.

The presently disclosed methods provide much needed routes for the synthesis of CBC at large scale by avoiding labor intensive column purification That is, because the reaction is clean, any purification is substantially less resource-intensive than the art methods, while the conversion, yield and purity are all significantly higher. The methods are also amendable to a continuous process. The method is applicable to other cannabinoid and CBC analogues.

The synthesis of Cannabichromene (CBC) was first reported by Elsohly and co-workers in U.S. Pat. No. 4,315,862 (1982). The authors reported they were able to synthesize CBC from citral and olivetol in the presence of a primary amine by using a tandem Knoevenagel-electrocyclic reaction. During this reaction, the authors slowly added citral to olivetol at 60° C. then, heated the reaction to reflux for another 9 hours. Overall, these reaction conditions were only able to produce CBC in 50-60% isolated yield. This synthesis involves adding to a three-necked round bottomed flask (100 ml capacity), fitted with a dropping funnel and a condenser, 5 g olivetol (27.8 mmole) and 2.03 g (2.96 ml., 27.8 mmole) t-butyl amine in 55 ml toluene. The mixture was heated to 50°–60° C., 4.23 g (4.76 ml., 27.8 mmole) of citral was then added dropwise. The mixture was refluxed for 9 hours, after which time it was cooled to room temperature and the solvent evaporated to give 9.3 g. of crude reaction mixture. Gas chromatographic analysis of the reaction mixture showed 59.46% CBC (molar conversion), 5.04% cannabicitran and trace amount of iso-CBC.

Although the synthesis of CBC can be in a one-step fashion, the reaction conditions itself produces other CBC and non-CBC derived impurities, including, but not limited to:

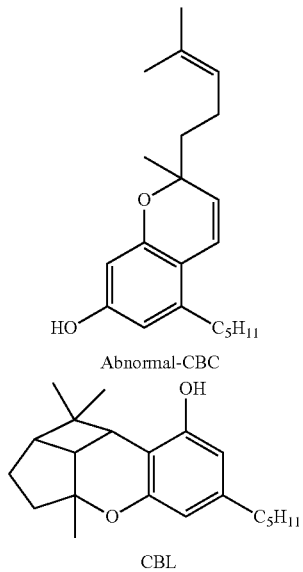

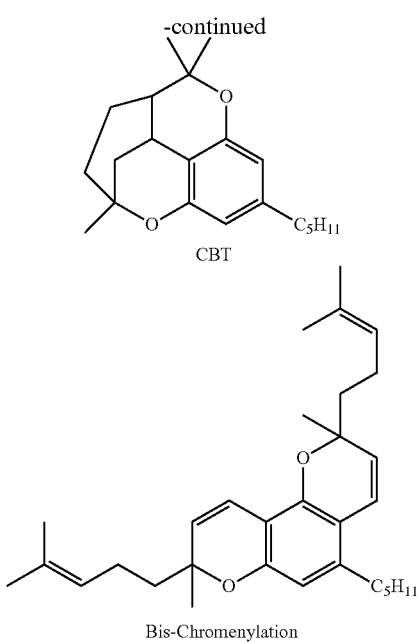

CBT

Bis-Chromenylation

The separation of these impurities from CBC has proven quite challenging during the purification process. Thereby, requiring multiple column purifications, rendering the process undesirable for scale-up. In addition, conventional distillation at atmospheric pressure is not an option as CBC readily decomposes under thermal conditions.

Recently, new methodologies have been developed to synthesize CBC from citral and olivetol. These new methodologies consist of using different amines (1°, 2°, or 3°), metal, or acid catalyst (Pollastro et al. *Natural Product Commun.* 2018, 13, 1189-1194; Hanus, L. O. Et al. Nat. Prod. Rep. 2016, 33, 1357-1392.) In the reported synthesis, citral is used at 1.09 eq. and olivetol is at 1.0 eq. From these developments, the mainly used catalyst to achieve higher conversion of CBC is ethylenediamine in scheme 2 of the article. However, the conversion to CBC only increased between the ranges of 60-80%. While the conversion of CBC was only a 1.3-fold increase, this decreased the production of some by-products like cannabacitran (CBT) to less than 1% as previous seen by Elsohly and co-workers.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

I. Definitions

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through or perpendicular across the end of a line in a structure indicates a specified point of attachment of a group. Unless chemically or structurally required, no directionality or stereochemistry is indicated or implied by the order in which a chemical group is written or named.

The prefix "$C_u$-$C_v$" indicates that the following group has from u to v carbon atoms. For example, "$C_1$-$C_6$alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±50%. In certain other embodiments, the term "about" includes the indicated amount±20%. In certain other embodiments, the term "about" includes the indicated amount±10%. In other embodiments, the term "about" includes the indicated amount±5%. In certain other embodiments, the term "about" includes the indicated amount±1%. In certain other embodiments, the term "about" includes the indicated amount±0.5% and in certain other embodiments, 0.1%. Such variations are appropriate to perform the disclosed methods or employ the disclosed compositions. Also, to the term "about x" includes description of "x". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art As used herein, the "CBC" refers to cannabichromene and "CBT" refers to cannabicitran. As used herein, a "derivative" refers to compounds of Formulae I and II, other than CBC and CBT.

The term "alkyl" as used herein refers to a saturated linear or branched-chain monovalent hydrocarbon radical of one to ten carbon atoms ($C_1$-$C_{10}$), wherein the alkyl radical may be optionally substituted independently with one or more substituents. In another embodiment, an alkyl radical is three to ten carbon atoms ($C_3$-$C_{10}$), or three to five carbon atoms ($C_3$-$C_5$), or one to six carbon atoms ($C_1$-$C_6$). Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl, and the like.

As used herein, "Alkenyl" refers to an alkyl group containing at least one carbon-carbon double bond and having from 2 to 10 carbon atoms (i.e., C$_2$-C$_{10}$ alkenyl), 2 to 8 carbon atoms (i.e., C$_2$-C$_8$ alkenyl), 2 to 6 carbon atoms (i.e., C$_2$-C$_6$ alkenyl) or 2 to 4 carbon atoms (i.e., C$_2$-C$_4$ alkenyl). Examples of alkenyl groups include, e.g., ethenyl, propenyl, butadienyl (including 1,2-butadienyl and 1,3-butadienyl).

As used herein, the term "dosing" refers to controllably allowing two or more reagents to contact each other. The dosing is controlled by rate. As used herein, the term "contacting" refers to allowing two or more reagents to contact each other. The contact may or may not be facilitated by mixing, agitating, stirring, and the like. A "controlled rate" as used herein refers to a deliberate rate of addition of reagent to prevent or lessen decomposition of the reagent before reaction and to provide a high IPC. Having been made aware of these specific parameters as described herein, one of skill in the art can through routine experimentation determine a dosing rate.

As used herein, the term "purity" refers to percentage purity of the compound of interest. Purity can be determined by any means known in the art. A preferred means is calculating purity using HPLC, and the like, to determine % AUC.

As used herein, the term "reduced impurities" and related terms refer to relative amounts of impurities compared to a compound of Formula I or II.

As used herein, and unless otherwise specified, the products comprising a CBC or CBT or derivative thereof can be in any form, in particular an oil or solid. Any form, such as an oil, that is "substantially chemically pure" is substantially free from other chemical compounds (i.e., chemical impurities). In certain embodiments, a solid form that is substantially chemically pure contains less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, oil or solid form, or composition that is "substantially free" of another chemical compound, oil or solid form, or composition means that the compound, oil or solid form, or composition contains, in certain embodiments, less than about 50%, 45%, 40%, 35%, 30%, 25%, 20%, 15%, 10%, 9%, 8%, 7%, 6%, 5%, 4%, 3%, 2%, %, 0.5%, 0.4%, 0.3%, 0.2% 0.1%, 0.05%, or 0.01% by weight of the other compound, oil or solid form, or composition.

Unless otherwise specified, the term "composition" as used herein is intended to encompass a product comprising the specified ingredient(s) (and in the specified amount(s), if indicated), as well as any product which results, directly or indirectly, from combination of the specified ingredient(s) in the specified amount(s). Additionally, the term "composition" refers to a mixture of compounds.

By "pharmaceutically acceptable," it is meant a diluent, excipient, or carrier in a formulation must be compatible with the other ingredient(s) of the formulation and not deleterious to the recipient thereof.

Unless otherwise specified, to the extent that there is a discrepancy between a depicted chemical structure of a compound provided herein and a chemical name of a compound provided herein, the chemical structure shall control.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of a particular disease.

A "patient" or "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the patient, individual, or subject is a human.

As used herein, the term "therapeutic amount" refers to an amount of a therapeutic agent, compound, formulation, material, or composition, as described herein effective to achieve a particular biological result. Such results may include, but are not limited to, the inhibition of a disease as determined by any means suitable in the art.

As used herein, the term "pharmaceutically acceptable excipient" refers to an ingredient in a pharmaceutical formulation, other than an active ingredient, which is nontoxic to a subject. A pharmaceutically acceptable excipient includes, but is not limited to, a buffer, carrier, stabilizer, or preservative.

Some compounds of Formulae I and II, or their pharmaceutically acceptable salts can include an asymmetric center and may thus give rise to enantiomers, diastereomers, and other stereoisomeric forms that may be defined, in terms of absolute stereochemistry, as (R) or (S) or, as (D) or (L) for amino acids. The present subject matter is meant to include all such possible isomers, as well as their racemic and optically pure forms. Optically active (+) and (−), (R) and (S), or (D) and (L) isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC). When the compounds described herein contain olefinic double bonds or other centers of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposable mirror images of one another.

"Diastereomers" are stereoisomers that have at least two asymmetric atoms, but which are not mirror-images of each other.

Additional definitions are provided below.

II. Methods of Preparing Compounds of Formulae I and II

In certain embodiments, the subject matter described herein is directed to methods of preparing a compound of Formula I or II,

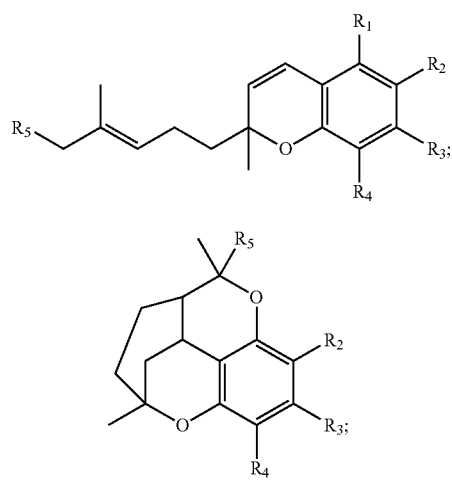

wherein,
- $R_1$ is selected from the group consisting of hydroxyl and $C_{1-5}$alkoxy;
- $R_2$ and $R_4$ are in each instance independently selected from the group consisting of hydrogen, —$C_{1-5}$alkyl, —$CF_3$, cyano, nitro, phenyl, —C(O)$R_6$, —$NR_aR_b$, —C(O)O$R_6$, —O—C(O)$R_6$, —O—$R_6$, —O—$R_6$, —C(H)=C($R_6$)$_2$, —N(H)C(O)$R_6$, halo, —N($R_6$)$_3$; wherein, $R_a$ and $R_b$ are each independently hydrogen or $C_{1-5}$alkyl;
  wherein, $R_6$ is hydrogen or $C_{1-5}$alkyl;
- $R_3$ is selected from the group consisting of hydrogen, linear or branched $C_{1-10}$alkyl;
- $R_5$ is selected from the group consisting of hydrogen, $C_{1-5}$alkyl, $C_{1-5}$alkenyl and prenyl;

comprising:
dosing at a first temperature above 65° C. a compound of Formula Ia

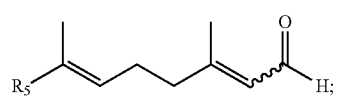

wherein, $R_5$ is as described above;
to a first mixture, said first mixture comprising an amine and a compound of Formula Ib

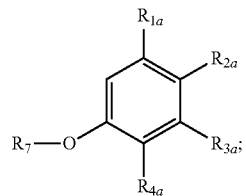

wherein,
- $R_{1a}$ is selected from the group consisting of hydroxyl and $C_{1-5}$alkoxy;
- $R_{2a}$ and $R_{4a}$ are each as described above for $R_2$ and $R_4$;
- $R_{3a}$ is selected from the group consisting of hydrogen, linear or branched $C_{1-10}$alkyl; and
- $R_7$ is selected from the group consisting of hydrogen, —C(O)$R_c$,
  wherein $R_c$ is hydrogen or $C_{1-5}$alkyl;

to form a second mixture; and,
allowing the second mixture to react at a second temperature;
wherein, a compound of Formula I or II is prepared.

The values of the R group variables in the starting materials of Formulae Ia and Ib will correspond to the respective variables in the final products of Formulae I and II.

In certain embodiments, $R_1$ is hydroxyl.

In certain embodiments, $R_2$ and $R_4$ are in each instance independently selected from the group consisting of hydrogen, cyano, C(O)O$R_6$, and halo, wherein, $R_6$ is hydrogen or $C_{1-5}$alkyl. In certain embodiments, $R_2$ and $R_4$ are in each instance independently selected from the group consisting of hydrogen and C(O)O$R_6$, wherein $R_6$ is hydrogen or $C_{1-5}$alkyl. In certain embodiments, $R_6$ is hydrogen. In certain embodiments, $R_2$ is C(O)OH and $R_4$ is hydrogen.

In certain embodiments, $R_3$ and $R_{3a}$ are each propyl, butyl or pentyl. In certain embodiments, $R_3$ is propyl, butyl or pentyl. In certain embodiments, $R_{3a}$ is propyl, butyl or pentyl.

In certain embodiments, $R_3$ is branched or linear $C_{3-10}$alkyl. In certain embodiments, $R_3$ is branched or linear $C_{3-5}$alkyl.

In all embodiments the values for $R_{1a}$, $R_{2a}$, $R_{3a}$ and $R_{4a}$ and $R_7$, in particular, the values for $R_{1a}$, $R_{2a}$, $R_{3a}$ and $R_{4a}$ are selected based on the desired values for $R_1$, $R_2$, $R_3$ and $R_4$, respectively in the compounds of Formula I or II.

In certain embodiments, the amine can be a primary amine, a secondary amine, a tertiary amine, or a diamine. In certain embodiments, the amine is a diamine. In certain embodiments, the amine is ethylenediamine, tetramethylethylene diamine, isopropylethylamine, piperidine, pyrrolidine, 1,6-hexane diamine. In certain embodiments, the amine is ethylenediamine.

In certain embodiments, the compound of Formula Ib has the formula:

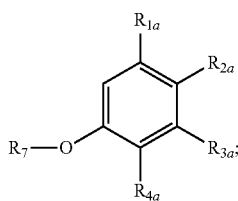

wherein,
$R_{1a}$ is selected from the group consisting of hydroxyl and $C_{1-5}$alkoxy;
$R_{2a}$ and $R_{4a}$ are as described above for $R_2$ and $R_4$;
$R_{3a}$ is selected from the group consisting of hydrogen, linear or branched $C_{1-10}$alkyl; and
$R_7$ is selected from the group consisting of hydrogen, —C(O)$R_c$,
wherein $R_c$ is hydrogen or $C_{1-5}$alkyl.

In certain embodiments, $R_{1a}$ is hydroxyl or $C_{1-5}$alkoxy; $R_{3a}$ is a linear $C_{1-10}$alkyl; and $R_7$ is selected from the group consisting of hydrogen, —C(O)$R_c$, wherein $R_c$ is hydrogen or $C_{1-5}$alkyl.

In certain embodiments, the compound of Formula Ib is:

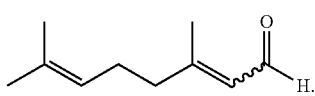

In certain embodiments, the compound of Formula Ia is:

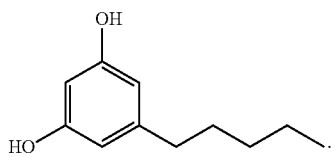

In certain embodiments, the first temperature is above 65° C., for example, 70° C. or higher. The first temperature can be from about 65° C. to about 200° C. In certain embodiments, the first temperature is above 75° C. to about 150° C. In certain embodiments, the first temperature is above 80° C. to about 110° C. In certain embodiments, the first temperature is above 80° C. to about 100° C. For example the first temperature is any integer from 65 to 200, including 80, 81, 82, 83, 84, 85, 86, 87, 88, 89, 90, 91, 92, 93, 94, 95, 96, 97, 98, 99 and 100.

In certain embodiments, the dosing of the compound of Formula Ia to the first mixture is at reflux. In certain embodiments, the dosing at a first temperature above 65° C. a compound of Formula Ia to a first mixture is at a controlled rate. In certain embodiments, the dosing at a first temperature above 65° C. a compound of Formula Ia to a first mixture is dropwise.

In certain embodiments, the dosing at a first temperature above 65° C. a compound of Formula Ia comprises contacting about 0.8 to about 1.3 molar equivalents of a compound of Formula Ia to a compound of Formula Ib. In certain embodiments, the dosing at a first temperature above 65° C. a compound of Formula Ia comprises contacting about 0.9 to about 1.18 molar equivalents of a compound of Formula Ia to a compound of Formula Ib. In certain embodiments, the dosing at a first temperature above 65° C. a compound of Formula Ia comprises contacting about 0.95 to about 1.09 molar equivalents of a compound of Formula Ia to a compound of Formula Ib. In certain embodiments, the dosing at a first temperature above 65° C. a compound of Formula Ia comprises contacting about 0.95, 0.96, 0.97, 0.98, 0.99, 1.0, 1.00, 1.01, 1.02, 1.03, 1.04, 1.05, 1.06, 1.07, 1.08 or 1.09 molar equivalents of a compound of Formula Ia to a compound of Formula Ib.

In certain embodiments, the first mixture comprises a solvent. In certain embodiments, the solvent is selected from the group consisting of toluene, xylene, THF, DMSO and DMF. In certain embodiments, the solvent is toluene.

In certain embodiments, the second temperature is above 65° C. to about 200° C. In certain embodiments, the second temperature is above 75° C. to about 150° C. In certain embodiments, the second temperature is above 80° C. to about 110° C. In certain embodiments, the second temperature is above 80° C. to about 100° C. For example the second temperature is any integer from 70 to 200, including 80, 81, 82, 83, 84, 85, 86, 87, 88, 89, 90, 91, 92, 93, 94, 95, 96, 97, 98, 99 and 100. In certain embodiments, the first temperature and the second temperature are the same.

In certain embodiments, the methods further comprise after the allowing the second mixture to react at a second temperature, separating an organic layer to collect an organic phase.

In certain embodiments, the methods further comprise distilling the organic phase to prepare a purified compound of Formula II. In this aspect, a chromatographic process is not used. The compound of Formula II is distilled directly after separating the organic layer.

In certain embodiments, the compound of Formula II has the structure:

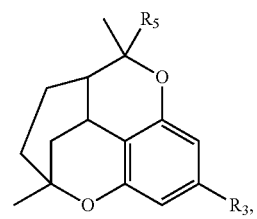

wherein, $R_3$ is selected from the group consisting of hydrogen, linear or branched $C_{1-10}$alkyl; and
$R_5$ is selected from the group consisting of hydrogen, $C_{1-5}$alkyl, $C_{1-5}$alkenyl and prenyl.

In certain embodiments, the compound of Formula II has the structure:

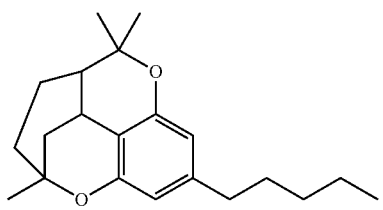

In certain embodiments, the methods further comprise contacting the organic phase with chromatographic media and collecting fractions containing a compound of Formula I. In certain embodiments, the chromatographic media is silica.

In certain embodiments, the fractions are distilled to prepare a purified compound of Formula I.

In certain embodiments, the compound of Formula I has the structure:

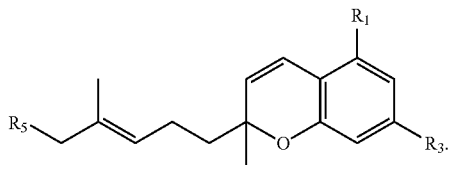

I

In certain embodiments, the compound of Formula I has the structure:

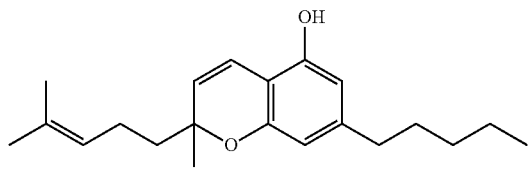

I

5.

In certain embodiments, the conversion to a compound of Formula I or II is greater than 80%, such as about 85%, about 90%, or about 95%.

In certain embodiments, the compound of Formula I has a purity of at least 80%. In certain embodiments, the compound of Formula I has a purity of at least 90%. In certain embodiments, the compound of Formula I has a purity of from about 90% to about 95%.

In certain embodiments, the compound of Formula II has a purity of at least 80%. In certain embodiments, the compound of Formula II has a purity of at least 90%. In certain embodiments, the compound of Formula II has a purity of from about 90% to about 95%.

In certain embodiments, by-products generally seen in known methods are reduced in the methods described herein. Relative to the compounds of Formula I and II, the by-products can be reduced by 1%, 5%, 10%, 15%, 20%, 25%, 30%, 35% or more. In certain embodiments, the relative amount(s) of by-products 1b, 2b and 3b to a compound of Formula I or II is reduced

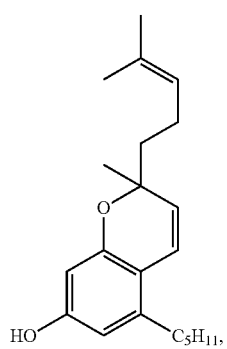

1b

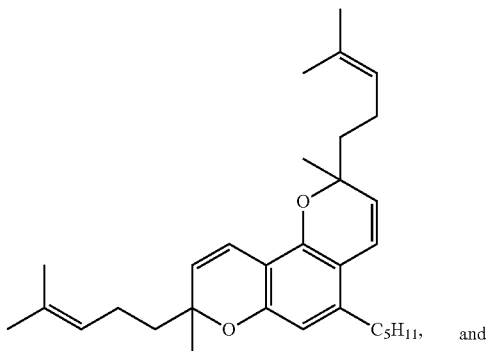

2b and

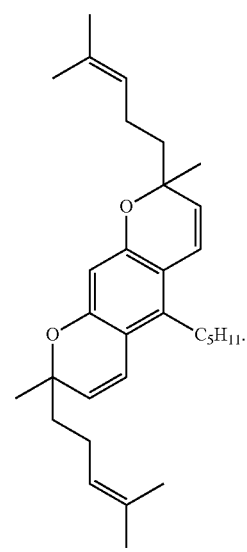

3b

In certain embodiments, the methods are directed to preparing a compound of Formula I,

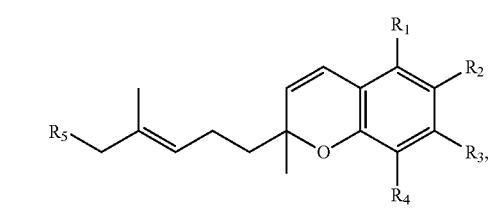

I wherein,
R$_1$ is selected from the group consisting of hydroxyl and C$_{1-5}$alkoxy;
R$_2$ and R$_4$ are in each instance independently selected from the group consisting of hydrogen, —C$_{1-5}$alkyl, —CF$_3$, cyano, nitro, phenyl, —C(O)R$_6$, —NR$_a$R$_b$, —C(O)OR$_6$, —O—C(O)R$_6$, —O—R$_6$, —O—R$_6$, —C(H)=C(R$_6$)$_2$, —N(H)C(O)R$_6$, halo, —N(R$_6$)$_3$; wherein, R$_a$ and R$_b$ are each independently hydrogen or C$_{1-5}$alkyl;
wherein, R$_6$ is hydrogen or C$_{1-5}$alkyl;
R$_3$ is selected from the group consisting of hydrogen, linear or branched C$_{1-10}$alkyl;
R$_5$ is selected from the group consisting of hydrogen, C$_{1-5}$alkyl, C$_{1-5}$alkenyl and prenyl;

comprising:
dosing at a first temperature above 65° C. a compound of Formula Ia

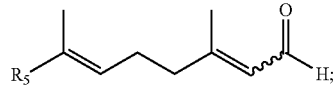

Ia wherein, $R_5$ is as described above;
to a first mixture, said first mixture comprising an amine and a compound of Formula Ib

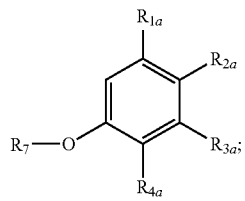

Ib wherein,
$R_{1a}$ is selected from the group consisting of hydroxyl and $C_{1-5}$alkoxy;
$R_{2a}$ and $R_{4a}$ are each as described above for $R_2$ and $R_4$;
$R_{3a}$ is selected from the group consisting of hydrogen, linear or branched $C_{1-10}$alkyl; and
$R_7$ is selected from the group consisting of hydrogen, —C(O)$R_c$,
wherein $R_c$ is hydrogen or $C_{1-5}$alkyl;
to form a second mixture;
allowing the second mixture to react at a second temperature;
separating an organic layer to collect an organic phase;
contacting the organic phase with chromatographic media;
eluting and collecting an eluate;
distilling the eluate;
wherein, a compound of Formula I is prepared.

In certain embodiments, to prepare a compound of Formula I, the dosing at a first temperature above 65° C. a compound of Formula Ia comprises contacting about 0.95 to about 1.09 molar equivalents of a compound of Formula Ia with a compound of Formula Ib.

In certain embodiments, to prepare a compound of Formula I, the first temperature and the second temperature are each independently from about from about 90° C. to about 110° C., or from about 80° C. to about 100° C.

In certain embodiments, to prepare a compound of Formula I, the amine is ethylenediamine.

In certain embodiments, the compound of Formula I is:

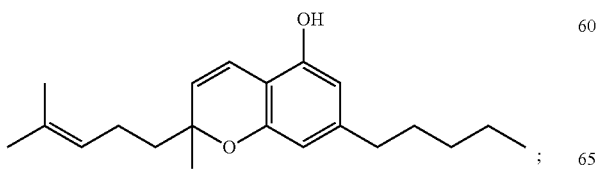

the compound of Formula Ia is:

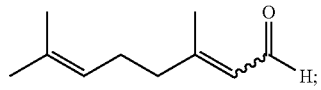

Ia and, the compound of Formula Ib is:

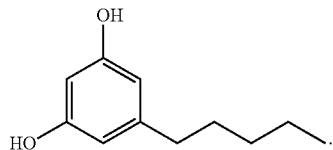

Ib

In certain embodiments, the methods are directed to preparing a compound of Formula II,

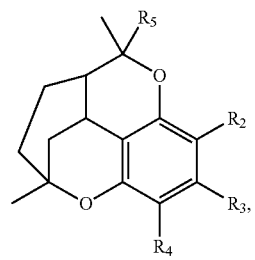

II wherein,
$R_2$ and $R_4$ are in each instance independently selected from the group consisting of hydrogen, —$C_{1-5}$alkyl, —$CF_3$, cyano, nitro, phenyl, —C(O)$R_6$, —N$R_aR_b$, —C(O)O$R_6$, —O—C(O)$R_6$, —O—$R_6$, —O—$R_6$, —C(H)=C($R_6$)$_2$, —N(H)C(O)$R_6$, halo, —N($R_6$)$_3$;
wherein, $R_a$ and $R_b$ are each independently hydrogen or $C_{1-5}$alkyl;
wherein, $R_6$ is hydrogen or $C_{1-5}$alkyl;
$R_3$ is selected from the group consisting of hydrogen, linear or branched $C_{1-10}$alkyl;
$R_5$ is selected from the group consisting of hydrogen, $C_{1-5}$alkyl, $C_{1-5}$alkenyl and prenyl;
comprising:
dosing at a first temperature above 65° C. a compound of Formula Ia

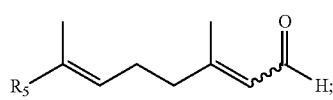

Ia wherein, $R_5$ is as described above;
to a first mixture, said first mixture comprising an amine and a compound of Formula Ib

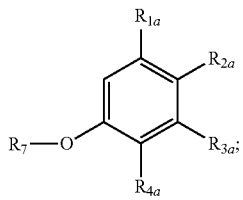

wherein,

R$_{1a}$ is selected from the group consisting of hydroxyl and C$_{1-5}$alkoxy;

R$_{2a}$ and R$_{4a}$ are each as described above for R$_2$ and R$_4$;

R$_{3a}$ is selected from the group consisting of hydrogen, linear or branched C$_{1-10}$alkyl; and R$_7$ is selected from the group consisting of hydrogen, —C(O)R$_c$, wherein R$_c$ is hydrogen or C$_{1-5}$alkyl;

to form a second mixture;

allowing the second mixture to react at a second temperature;

separating an organic layer to prepare an organic phase;

distilling the organic phase;

wherein, a compound of Formula II is prepared.

In certain embodiments, to prepare a compound of Formula II, the dosing at a first temperature above 65° C. a compound of Formula Ia comprises contacting about 0.95 to about 1.09 molar equivalents of a compound of Formula Ia with a compound of Formula Ib.

In certain embodiments, to prepare a compound of Formula II, the first temperature and the second temperature are each independently from about from about 90° C. to about 110° C., or from about 80° C. to about 100° C.

In certain embodiments, to prepare a compound of Formula II, the amine is ethylenediamine.

In certain embodiments, the compound of Formula II is:

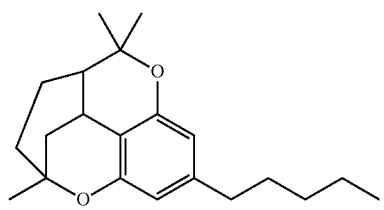

the compound of Formula Ia is:

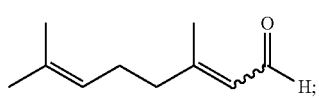

and, the compound of Formula Ib is:

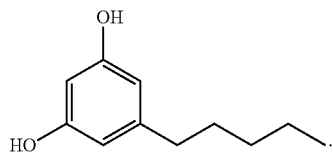

In certain embodiments, when the method comprises a distillation, the distilling is at a temperature of above 150° C.

In certain embodiments, any suitable solvent can be used. In certain embodiments, the solvent is selected from the group consisting of THF, DMSO, toluene, xylene, methanol, methyl-THF, ethanol, isopropanol, butanol or other C$_{1-4}$ alcohol, DMF and water, and mixtures thereof. In certain embodiments, the solvent is selected from the group consisting of toluene, benzene, xylene, THF, DMSO and DMF. In certain embodiments, the solvent is toluene.

In certain embodiments, the method does not comprise a chromatographic purification or only minimal chromatography compared to known methods. For example, the reaction is clean and may require only a single chromatographic procedure to achieve the desired purity, compared to art methods that require multiple procedures that may never result in the desired purity. In embodiments, the product of one step can be used in the next reaction step without purification. In certain embodiments, it is advantageous that the reaction can prepare the compounds of Formulae I and II without the need for column chromatography to purify a target compound. When a purification method is used, it is to be understood that the reaction is substantially cleaner than art methods and requires much less purification. As used herein, column chromatography refers to the separation of bulk substances based on differential adsorption of compounds to the adsorbent in a column, where compounds move through the column at different rates, which allows different compounds to be separated into fractions.

A result of the methods described herein, the overall reaction proceeds to prepare compounds of Formulae I and II at high conversion and purity. In certain embodiments, the compound of Formula I or II has a purity (area %, also referred to as AUC) of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In certain embodiments, the methods have a conversion of about 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "distillation" is intended to denote the type of separation conventional in chemical engineering and described, for example, in "Perry's Chemical Engineers' Handbook" in the 13th section of the 7th edition, and, is generally a method of separating mixtures based on differences in their volatilities in a boiling liquid mixture. The term "fractional distillation" is understood to mean a series of distillations where the distillate is withdrawn batch wise. Generally, a fractioning column is connected to a reflux condenser and a means for collecting fractions. Fractions can be collected at any desired temperature or range of temperatures.

In certain embodiments, one or more distillates are combined. In certain embodiments, the target compound in the distillate has a purity (AUC) of at least 80%. In certain embodiments, the target compound in the distillate has a purity (AUC) of at least 90%. In certain embodiments, the target compound in the distillate has a purity (AUC) of at least 99%, or about 99.1%, 99.2%, 99.3%, 99.4%, 99.5%, 99.6%, 99.7%, 99.8%, 99.9% or higher.

General Procedures

Compounds of Formulae I and II can be synthesized by synthetic routes described herein. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-23, Wiley, N.Y. (1967-2006 ed.), or Beilsteins Handbuch der organischen Chemie, 4, Aufl. ed. Springer-Verlag, Berlin, including supplements (also available via the Beilstein online database).

Those of skill in this art are aware of synthetic chemistry transformations and protecting group methodologies (protection and deprotection) that in combination with the reactions disclosed herein are useful in synthesizing Formula I compounds (and any intermediates) and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, 3rd Ed., John Wiley and Sons (1999); and L. Paquette, ed., Encyclopedia of Reagents for Organic Synthesis, John Wiley and Sons (1995) and subsequent editions thereof.

In preparing compounds of Formulae I and II, protection of functionality (e.g., alcohols) of intermediates may be necessary. The need for such protection will vary depending on the nature of the remote functionality and the conditions of the preparation methods. The need for such protection is readily determined by one skilled in the art. For a general description of protecting groups and their use, see T. W. Greene, Protective Groups in Organic Synthesis, John Wiley & Sons, New York, 1991.

Scheme 1 is a general synthetic route for preparing a compound of Formula I.

Scheme 1

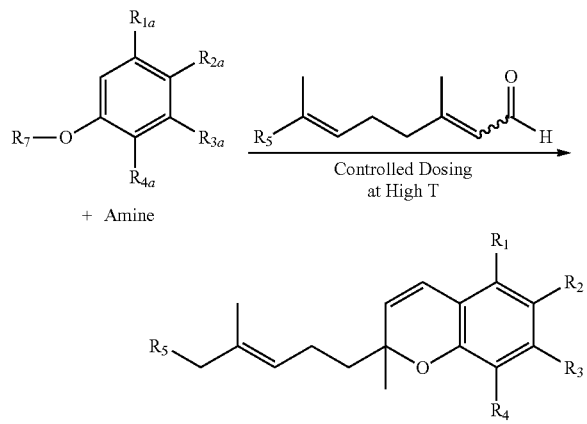

There are two parameters that preferably are controlled in the methods: dosing of citral to olivetol at elevated temperatures; and an IPC no less than about 80%. Dosing of the compound of Formula Ia, e.g. citral, at 0.95-1.09 equiv. results in a cleaner reaction. Equivalents tested outside the range, 1.18 eqv. and 0.90 eqv. results in unclean reactions. Dosing of the compound of Formula Ia, e.g., citral in toluene solution, at high temperature is shown to be advantageous. For example, the IPC result for the reaction with dosing at 60° C. was only ~70%. The IPC is preferably no less than about 83%; more preferably no less than 83%. As such, preferred IPCs include 83%, 84%, 85%, 86%, 87%, 88%, 89%, 90%, 91%, 92%, 93%, 94%, 95%, 96%, 97%, 98%, or 99%.

In certain embodiments, once the reaction IPC is at such a level, to prepare Formula I the methods comprise Steps 1-6; or to prepare Formula II compounds the methods comprise Steps 1-4a as outlined below:
1. Water wash
2. Separation of organic and aqueous layer
3. Drying of organic layer (optional)
4. Remove solvent
   4a. Distill to prepare purified compounds of Formula II
5. A purification method, such as extraction or silica column, to remove any unreacted amine;
6. Distill to prepare purified compounds of Formula I Scheme 2 is a general synthetic route for preparing a compound of Formula II.

Scheme 2

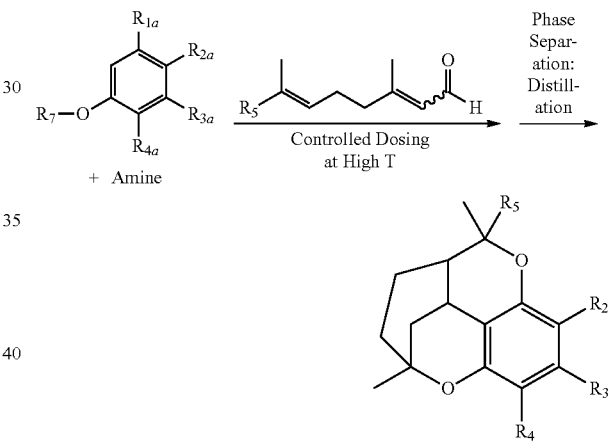

In certain embodiments, the synthetic route is used to prepare CBC (Scheme 3). Citral is dosed at a controlled rate at elevated temperature.

Scheme 3

In certain embodiments, the synthetic route is used to prepare CBT (Scheme 4). Citral is dosed at a controlled rate at elevated temperature.

Scheme 4

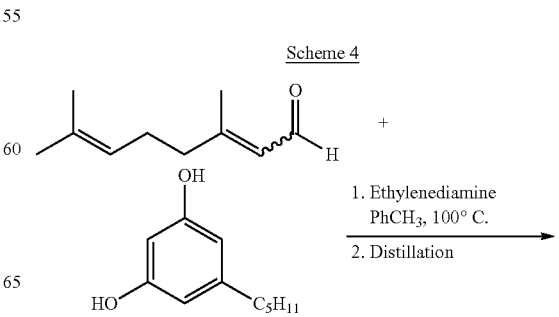

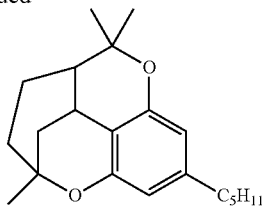

In certain embodiments, the methods further comprise quenching of the reaction mixture, whereby the reaction mixture is separated into a top organic layer and a bottom aqueous layer. In embodiments, the organic layer is extracted. In certain embodiments, the organic layer is washed with water.

The General Procedures and Examples provide exemplary methods for preparing Formulae I and II compounds. Those skilled in the art will appreciate that routine modifications to the synthetic routes may be used to synthesize the Formulae I and II compounds. Although specific starting materials and reagents are depicted and discussed in the schemes, General Procedures, and Examples, other starting materials and reagents may be substituted to provide a variety of derivatives and/or reaction conditions.

III. Indications and Methods of Treatment

It is contemplated that the compounds of Formulae I and II disclosed herein may be used as analgesics, antibiotics, to reduce intraocular pressure, and/or to treat a disease responsive to immunosuppressive and anti-inflammatory properties of cannabinoids. The diseases may include, but are not limited to, emesis, pain, epilepsy, Alzheimer's disease, Huntington's disease, Tourette's syndrome, glaucoma, osteoporosis, schizophrenia, cancer, obesity, autoimmune diseases, diabetic complications, infections against methicillin-resistant *Staphylococcus aureus*, nausea, depression, anxiety, Hypoxia-ischemia injuries, psychosis, and inflammatory diseases.

In certain embodiments, the subject matter described herein is directed to a method of treating a disease responsive to a compound of Formula I or II comprising administering to a subject an effective amount of the compound of Formula I or II.

Autoimmune diseases include, for example, Acquired Immunodeficiency Syndrome (AIDS), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, Parkinson's disease, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjögren's syndrome, stiff-man syndrome, systemic lupus erythematosus, Takayasu arteritis, temporal arteritis/giant cell arteritis, ulcerative colitis, uveitis, vitiligo and Wegener's granulomatosis.

Inflammatory disorders, include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, inflammatory bowel disease, sepsis, stroke, transplantation of tissue and organs, vasculitis, diabetic retinopathy and ventilator induced lung injury.

Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The compounds of Formula I or II can be administered by any route appropriate to the condition to be treated, including orally, intravenously, topically, as well as by ophthalmic (eye drops), and transdermal (skin patch) modes.

The compounds of Formula I or II can be used either alone or in combination with other agents in a therapy. For instance, the Formula I or II compounds or compositions may be co-administered with at least one additional therapeutic agent. Such combination therapies noted above encompass combined administration (where two or more therapeutic agents are included in the same or separate formulations), and separate administration, in which case, administration of the Formula I or II compounds or compositions can occur prior to, simultaneously, and/or following, administration of the additional therapeutic agent and/or adjuvant.

IV. Formulations

Pharmaceutical formulations where the active pharmaceutical ingredient (API) is a compound of Formula I or II as prepared by the methods described herein can be formulated for various routes of administration. The compound having the desired degree of purity is optionally mixed with one or more pharmaceutically acceptable excipients (Remington's Pharmaceutical Sciences (1980) 16th edition, Osol, A. Ed.). The compound can be formulated in accordance with standard pharmaceutical practice as a pharmaceutical composition. In embodiments, the compound formulation comprises a pharmaceutically acceptable excipient.

A typical formulation is prepared by mixing the compound with excipients, such as carriers and/or diluents.

Suitable carriers, diluents and other excipients are well known to those skilled in the art and include materials such as carbohydrates, waxes, water soluble and/or swellable polymers, hydrophilic or hydrophobic materials, gelatin, oils, solvents, water and the like. The particular carrier, diluent or other excipient used will depend upon the means and purpose for which the compound is being applied. Solvents are generally selected based on solvents recognized by persons skilled in the art as safe (GRAS) to be administered to a mammal.

In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEENÔ, PLURONICSÔ or polyethylene glycol (PEG).

The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the compound or aid in the manufacturing of the pharmaceutical product. The formulations may be prepared using conventional dissolution and mixing procedures.

Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound formulations can be sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution.

The pharmaceutical compositions comprising the compound can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutic amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

The compound can be formulated into pharmaceutical dosage forms to provide an easily controllable dosage of the drug and to enable patient compliance with the prescribed regimen. The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such 1,3-butanediol. The sterile injectable preparation may also be prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The amount of the compound that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 g of the active ingredient per milliliter of solution in order that infusion of a suitable volume at a rate of about 30 mL/hr can occur.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The subject matter described herein includes the following embodiments:

1. A method of preparing a compound of Formula I or II,

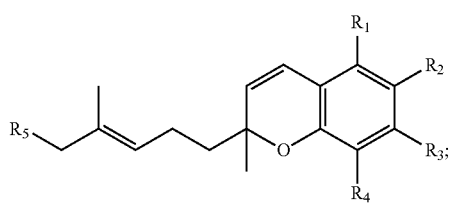

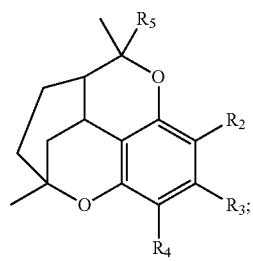

wherein, $R_1$ is selected from the group consisting of hydroxyl and $C_{1-5}$alkoxy;

$R_2$ and $R_4$ are in each instance independently selected from the group consisting of hydrogen, —$C_{1-5}$alkyl, —$CF_3$, cyano, nitro, phenyl, —$C(O)R_6$, —$NR_aR_b$, —$C(O)OR_6$, —O—$C(O)R_6$, —O—$R_6$, —O—$R_6$, —$C(H)$=$C(R_6)_2$, —$N(H)C(O)R_6$, halo, —$N(R_6)_3$;

wherein, $R_a$ and $R_b$ are each independently hydrogen or $C_{1-5}$alkyl;

wherein, $R_6$ is hydrogen or $C_{1-5}$alkyl;

$R_3$ is selected from the group consisting of hydrogen, linear or branched $C_{1-10}$alkyl;

$R_5$ is selected from the group consisting of hydrogen, $C_{1-5}$alkyl, $C_{1-5}$alkenyl and prenyl;

comprising:

dosing at a first temperature above 65, such as above 70° C. a compound of Formula Ia

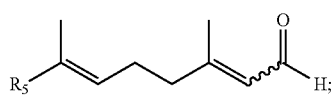

wherein, $R_5$ is as described above;

to a first mixture, said first mixture comprising an amine and a compound of Formula Ib

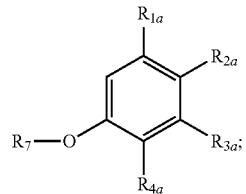

wherein, $R_{1a}$ is selected from the group consisting of hydroxyl and $C_{1-5}$alkoxy;

$R_{2a}$ and $R_{4a}$ are each as described above for $R_2$ and $R_4$;

$R_{3a}$ is selected from the group consisting of hydrogen, linear or branched $C_{1-10}$alkyl; and $R_7$ is selected from the group consisting of hydrogen, —$C(O)R_c$, wherein $R_c$ is hydrogen or $C_{1-5}$alkyl;

to form a second mixture; and, allowing the second mixture to react at a second temperature;

wherein, a compound of Formula I or II is prepared.

2. The method of embodiment 1, wherein $R_1$ is hydroxyl.

3. The method of any above embodiment, wherein $R_3$ is branched or linear $C_{3-10}$alkyl.

4. The method of any above embodiment, wherein the amine is a diamine.

5. The method of any above embodiment, wherein the amine is ethylenediamine.

6. The method of any above embodiment, wherein the compound of Formula Ib has the formula:

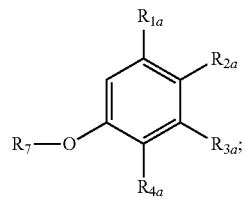

wherein, $R_{1a}$ is selected from the group consisting of hydroxyl and $C_{1-5}$alkoxy;

$R_{3a}$ is selected from the group consisting of hydrogen, linear or branched $C_{1-10}$alkyl; and $R_7$ is selected from the group consisting of hydrogen, —$C(O)R_c$, wherein $R_c$ is hydrogen or $C_{1-5}$alkyl.

7. The method of any above embodiment, wherein $R_{1a}$ is hydroxyl or $C_{1-5}$alkoxy;

$R_{3a}$ is a linear $C_{1-10}$alkyl; and $R_7$ is selected from the group consisting of hydrogen, —$C(O)R_c$, wherein $R_c$ is hydrogen or $C_{1-5}$alkyl.

8. The method of any above embodiment, wherein the compound of Formula Ib is:

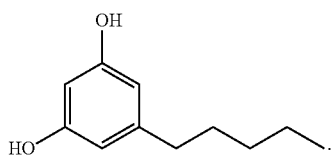

9. The method of any above embodiment, wherein the compound of Formula Ia is:

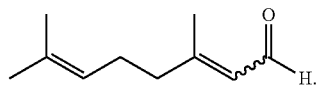

10. The method of any above embodiment, wherein the first temperature is above 70° C. to about 200° C.

11. The method of any above embodiment, wherein the first temperature is from about 75° C. to about 150° C.

12. The method of any above embodiment, wherein the first temperature is from about 80° C. to about 110° C.

13. The method of any above embodiment, wherein the first temperature is from about 80° C. to about 100° C.

14. The method of any above embodiment, wherein the dosing of the compound of Formula Ia to the first mixture is at reflux.

15. The method of any above embodiment, wherein the first mixture comprises a solvent.

16. The method of any above embodiment, wherein the solvent is selected from the group consisting of toluene, xylene, THF, DMSO and DMF.

17. The method of any above embodiment, wherein the solvent is toluene.

18. The method of any above embodiment, wherein the dosing at a first temperature above 70° C. a compound of Formula Ia to a first mixture is at a controlled rate.

19. The method of any above embodiment, wherein the dosing at a first temperature above 70° C. a compound of Formula Ia to a first mixture is dropwise.

20. The method of any above embodiment, wherein the dosing at a first temperature above 70° C. a compound of Formula Ia comprises contacting about 0.8 to about 1.3 molar equivalents of a compound of Formula Ia to a compound of Formula Ib.

21. The method of any above embodiment, wherein the contacting at a first temperature above 70° C. a compound of Formula Ia comprises contacting about 0.9 to about 1.18 molar equivalents of a compound of Formula Ia to a compound of Formula Ib.

22. The method of any above embodiment, wherein the contacting at a first temperature above 70° C. a compound of Formula Ia comprises contacting about 0.95 to about 1.09 molar equivalents of a compound of Formula Ia to a compound of Formula Ib.

23. The method of any above embodiment, wherein the second temperature is from about 70° C. to about 200° C.

24. The method of any above embodiment, wherein the second temperature is from about 80° C. to about 110° C.

25. The method of any above embodiment, wherein the second temperature is from about 80° C. to about 100° C.

26. The method of any above embodiment, further comprising after the allowing the second mixture to react at a second temperature, separating an organic layer to collect an organic phase.

27. The method of any above embodiment, further comprising distilling the organic phase to prepare a purified compound of Formula II.

28. The method of any above embodiment, wherein the compound of Formula II has the structure:

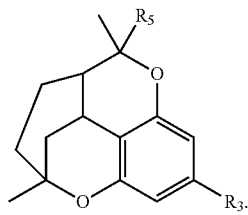

29. The method of any above embodiment, wherein the compound of Formula II has the structure:

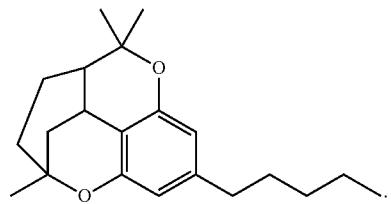

30. The method of any above embodiment, further comprising contacting the organic phase with chromatographic media and collecting fractions containing a compound of Formula I.

31. The method of any above embodiment, wherein the chromatographic media is silica.

32. The method of any above embodiment, wherein the fractions are distilled to prepare a purified compound of Formula I.

33. The method of any above embodiment, wherein the compound of Formula I has the structure:

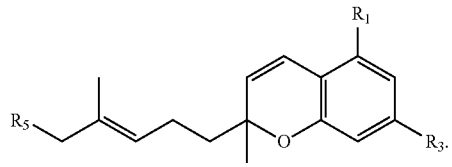

34. The method of any above embodiment, wherein the compound of Formula I has the structure:

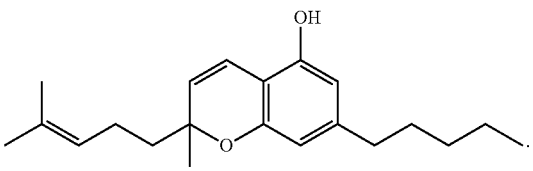

35. The method of any above embodiment, wherein the conversion to a compound of Formula I or II is greater than 80%.

36. The method of any above embodiment, wherein the compound of Formula II has a purity of at least 80%.

37. The method of any above embodiment, wherein the compound of Formula II has a purity of at least 90%.

38. The method of any above embodiment, wherein the compound of Formula II has a purity of from about 90% to about 95%.

39. The method of any above embodiment, wherein the compound of Formula I has a purity of at least 80%.

40. The method of any above embodiment, wherein the compound of Formula I has a purity of at least 90%.

41. The method of any above embodiment, wherein the compound of Formula II has a purity of from about 90% to about 95%.

42. The method of any above embodiment, wherein the relative amount of by-products 1b, 2b and 3b to a compound of Formula I or II is reduced

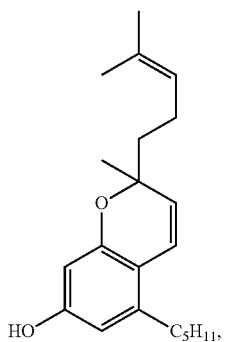
1b

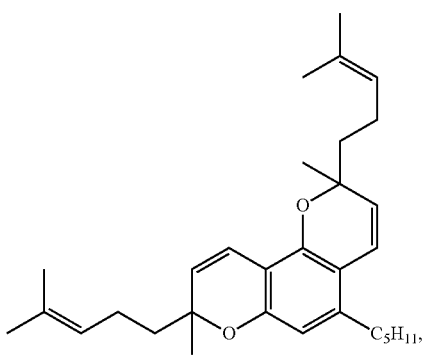
2b and

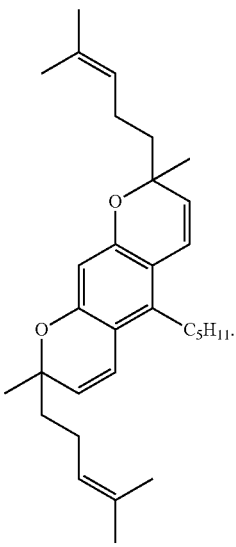
3b

43. The method of any above embodiment, for preparing a compound of Formula I,

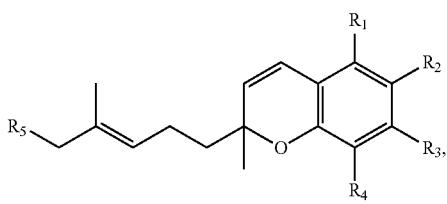
I wherein,
R$_1$ is selected from the group consisting of hydroxyl and C$_{1-5}$alkoxy;
R$_2$ and R$_4$ are in each instance independently selected from the group consisting of hydrogen, —C$_{1-5}$alkyl, —CF$_3$, cyano, nitro, phenyl, —C(O)R$_6$, —NR$_a$R$_b$, —C(O)OR$_6$, —O—C(O)R$_6$, —O—R$_6$, —O—R$_6$, —C(H)=C(R$_6$)$_2$, —N(H)C(O)R$_6$, halo, —N(R$_6$)$_3$;
wherein, R$_a$ and R$_b$ are each independently hydrogen or C$_{1-5}$alkyl;
wherein, R$_6$ is hydrogen or C$_{1-5}$alkyl;
R$_3$ is selected from the group consisting of hydrogen, linear or branched C$_{1-10}$alkyl;
R$_5$ is selected from the group consisting of hydrogen, C$_{1-5}$alkyl, C$_{1-5}$alkenyl and prenyl;
comprising:
dosing at a first temperature above 65° C., such as above 70° C. a compound of Formula Ia

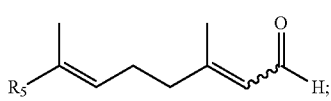
Ia wherein, R$_5$ is as described above;
to a first mixture, said first mixture comprising an amine and a compound of Formula Ib

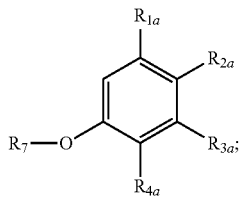

wherein,
- $R_{1a}$ is selected from the group consisting of hydroxyl and $C_{1-5}$alkoxy;
- $R_{2a}$ and $R_{4a}$ are each as described above for $R_2$ and $R_4$;
- $R_{3a}$ is selected from the group consisting of hydrogen, linear or branched $C_{1-10}$alkyl; and
- $R_7$ is selected from the group consisting of hydrogen, —C(O)$R_c$,
  - wherein $R_c$ is hydrogen or $C_{1-5}$alkyl;

to form a second mixture;
allowing the second mixture to react at a second temperature;
separating an organic layer to collect an organic phase;
contacting the organic phase with chromatographic media;
eluting and collecting an eluate;
distilling the eluate;
wherein, a compound of Formula I is prepared.

44. The method of any above embodiment, wherein the dosing at a first temperature above 70° C. a compound of Formula Ia comprises contacting about 0.95 to about 1.09 molar equivalents of a compound of Formula Ia with a compound of Formula Ib.

45. The method of any above embodiment, wherein the first temperature and the second temperature are each independently from about from about 80° C. to about 100° C.

46. The method of any above embodiment, wherein the amine is ethylenediamine.

47. The method of any above embodiment, wherein the compound of Formula I is:

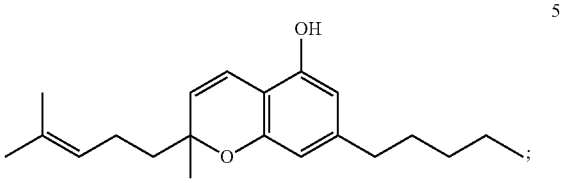 [SMILES: CCCCCc1cc(O)c2c(c1)OC(C)(CCC=C(C)C)C=C2]

the compound of Formula Ia is:

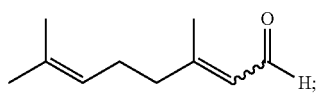

and, the compound of Formula Ib is:

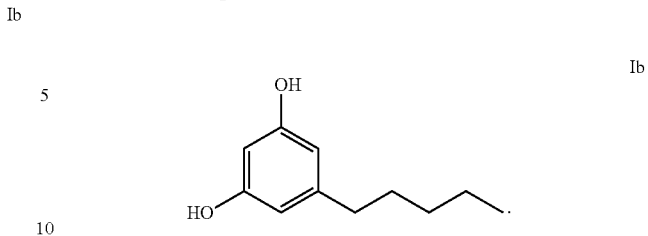

48. The method of any above embodiment, for preparing a compound of Formula II,

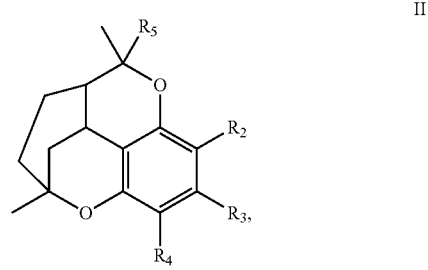

wherein,
- $R_2$ and $R_4$ are in each instance independently selected from the group consisting of hydrogen, —$C_{1-5}$alkyl, —$CF_3$, cyano, nitro, phenyl, —C(O)$R_6$, —N$R_aR_b$, —C(O)O$R_6$, —O—C(O)$R_6$, —O—$R_6$, —O—$R_6$, —C(H)=C($R_6$)$_2$, —N(H)C(O)$R_6$, halo, —N($R_6$)$_3$;
  wherein, $R_a$ and $R_b$ are each independently hydrogen or $C_{1-5}$alkyl;
  wherein, $R_6$ is hydrogen or $C_{1-5}$alkyl;
- $R_3$ is selected from the group consisting of hydrogen, linear or branched $C_{1-10}$alkyl;
- $R_5$ is selected from the group consisting of hydrogen, $C_{1-5}$alkyl, $C_{1-5}$alkenyl and prenyl;

comprising:
  dosing at a first temperature above 65° C., such as 70° C. a compound of Formula Ia

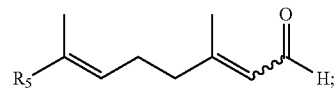

wherein, $R_5$ is as described above;
to a first mixture, said first mixture comprising an amine and a compound of Formula Ib

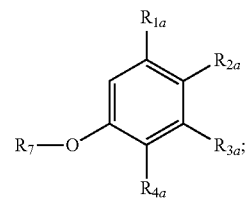

wherein,
- $R_{1a}$ is selected from the group consisting of hydroxyl and $C_{1-5}$alkoxy;

$R_{2a}$ and $R_{4a}$ are each as described above for $R_2$ and $R_4$;

$R_{3a}$ is selected from the group consisting of hydrogen, linear or branched $C_{1-10}$alkyl; and $R_7$ is selected from the group consisting of hydrogen, —C(O)$R_c$, wherein $R_c$ is hydrogen or $C_{1-5}$alkyl;

to form a second mixture;

allowing the second mixture to react at a second temperature;

separating an organic layer to prepare an organic phase;

distilling the organic phase;

wherein, a compound of Formula II is prepared.

49. The method of any above embodiment, wherein the dosing at a first temperature above 70° C. a compound of Formula Ia comprises contacting about 0.95 to about 1.09 molar equivalents of a compound of Formula Ia to a compound of Formula Ib.

50. The method of any above embodiment, wherein the first temperature and the second temperature are each independently from about from about 90° C. to about 110° C.

51. The method of any above embodiment, wherein the amine is ethylenediamine.

52. The method of any above embodiment, wherein the compound of Formula II is:

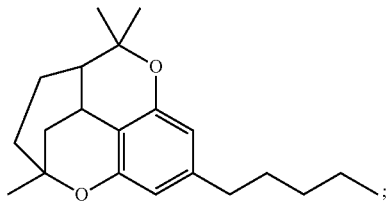

the compound of Formula Ia is:

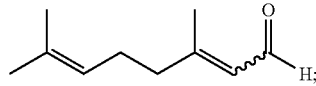

and, the compound of Formula Ib is:

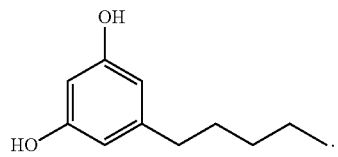

53. The method of embodiment 1, 43 or 48, wherein $R_2$ and $R_4$ are in each instance independently selected from the group consisting of hydrogen, cyano, —C(O)O$R_6$, and halo, wherein, $R_6$ is hydrogen or $C_{1-5}$alkyl.

54. The method of any above embodiment, wherein $R_2$ and $R_4$ are in each instance independently selected from the group consisting of hydrogen and —C(O)O$R_6$, wherein $R_6$ is hydrogen or $C_{1-5}$alkyl.

55. The method of any above embodiment, $R_6$ is hydrogen.

56. The method of any above embodiment, wherein $R_2$ is —C(O)OH and $R_4$ is hydrogen.

57. The method of embodiment 1, 43 or 48, wherein $R_3$ and $R_{3a}$ are each propyl, butyl or pentyl.

58. The method of any above embodiment, wherein $R_3$ is propyl, butyl or pentyl.

59. The method of any above embodiment, wherein $R_{3a}$ is propyl, butyl or pentyl.

60. The method of embodiment 27, wherein said distilling is at a temperature of above 150° C.

61. The method of embodiment 27, wherein said method does not comprise a chromatographic purification.

62. The method of any above embodiment, wherein the IPC is no less than 80%, or is preferably no less than about 83%; or more preferably no less than 83%.

63. A compound of Formula I or II made by the process of any above embodiment.

64. A pharmaceutical composition comprising a compound of Formula I or II and a pharmaceutically acceptable excipient.

65. A method of treating a disease responsive to a compound of Formula I or II comprising administering to a subject an effective amount of the compound of Formula I or II.

The disclosed subject matter is further described in the following non-limiting Examples. It should be understood that these Examples, while indicating preferred embodiments of the invention, are given by way of illustration only.

EXAMPLES

Example 1: Preparation of Cannabichrome

Materials:
  Citral (cis+trans) 95%; Alfa-Aesar, Lot #10220684; MW: 152.24 g/mo, D=0.888 g/mL; exp: Oct. 4, 2022
  Ethyelenediamine 99% (vendor: Alfa-Aesar, Lot #S22E009), MW: 60.10 g/mol; D=0.899 g/mL; exp: Jan. 22, 2002
  Toluene (anhydrous); Vendor: Sigma-Aldrich, Lot #SHBJ7776; Exp: Feb. 5, 2022.
  Olivetol; Vendor: SCI pharmtech inc; Lot #1805P122; Exp: Feb. 18, 2024; NC370
  Sodium Sulfate: BDH, Lot #1327C515, Exp. Feb. 17, 2025
  Heptane: Sky Chemicals; lot #T300C2L
  Heptane: VWR Chemicals; lot #0000232306; exp: Dec. 6, 2022
  Ethyl acetate: VWR Chemicals; Lot #18Z1278, exp: Jul. 23, 2021
  Silica Gel: SiliaFlash P60; size 40-63 m (230-400 mesh); lot: 040619; PN: R12030B Procedure:
  Prepared a 2-neck round bottom flask (250 mL) equipped with a reflux condenser and nitrogen blanket
  Charged olivetol (10.05 g, 56.0 mmol, 1.00 equiv.)
  Charged anhydrous toluene (125 mL)
  Charged ethylenediamine (0.67 g, 11.2 mmol, 20 mol %)
  Heated the reaction mixture to reflux Feb. 4, 2020 9:34:04 AM (GMT −05:00:00) Reached reflux at 9:55:24 AM (GMT −05:00:00)
  Charged citral (9.3 g, 61.4 mmol, 1.09 equiv.) toluene (30 mL) solution drop-wisely in 12 min. Started dosing at 9:55:32 AM (GMT −05:00:00)—Finished dosing at 10:07:17 AM (GMT −05:00:00)
  Turned off the heat at 11:09:08 AM (GMT −05:00:00)
  Cooled the reaction mixture to 25C
  Washed the reaction mixture with water (155 mL×2)

The top toluene/product layer was dried over sodium sulfate (15 g)

Filtered off the drying reagent

Washed the cake with toluene (10 mL)

Removed toluene using rotovap under vacuum at 60 C to obtain a brown crude oil

The crude reaction mixture TIPLC data are shown in FIG. 1 and Table 1.

TABLE 1

| | Name | Retention Time | Area | % Area | Height |
|---|---|---|---|---|---|
| 1 | | 1.322 | 69535 | 0.95 | 11812 |
| 2 | | 1.543 | 13688 | 0.19 | 2569 |
| 3 | | 1.660 | 71991 | 0.98 | 21313 |
| 4 | | 1.791 | 4548 | 0.06 | 1165 |
| 5 | | 1.926 | 14893 | 0.20 | 2591 |
| 6 | | 2.082 | 53558 | 0.73 | 6830 |
| 7 | | 2.441 | 434220 | 5.91 | 100661 |
| 8 | | 2.567 | 35813 | 0.49 | 7193 |
| 9 | | 2.864 | 971 | 0.01 | 230 |
| 10 | | 3.048 | 18251 | 0.25 | 3662 |
| 11 | | 3.283 | 16938 | 0.23 | 3718 |
| 12 | | 3.538 | 2077 | 0.03 | 327 |
| 13 | | 3.667 | 1186 | 0.02 | 229 |
| 14 | | 3.794 | 1391 | 0.02 | 254 |
| 15 | | 3.942 | 53437 | 0.73 | 11029 |
| 16 | CBC | 4.158 | 6314491 | 85.92 | 1405788 |
| 17 | | 4.705 | 12736 | 0.17 | 1132 |
| 18 | | 4.814 | 4019 | 0.05 | 819 |
| 19 | | 4.949 | 3933 | 0.05 | 509 |
| 20 | | 5.159 | 1049 | 0.01 | 203 |
| 21 | | 5.356 | 2489 | 0.03 | 305 |
| 22 | | 5.697 | 10468 | 0.14 | 990 |
| 23 | | 5.783 | 14291 | 0.19 | 1191 |
| 24 | | 6.370 | 58374 | 0.79 | 5433 |
| 25 | | 6.607 | 5210 | 0.07 | 1131 |
| 26 | | 6.654 | 9426 | 0.13 | 1154 |
| 27 | | 6.890 | 47064 | 0.64 | 7415 |
| 28 | | 7.242 | 7267 | 0.10 | 626 |
| 29 | | 7.703 | 65555 | 0.89 | 14705 |

Purification:

Purified the crude oil using column chromatography with an increasing gradient of (100% n-Heptane, then 3% EA/n-Heptane, v/v).

Three samples were collected: Sample A—Fraction 4-13 (9.30 g); Sample B—Fraction 14-19 (3.8 g); Sample C—Fraction 20-25 (1.88 g); Total: 14.98 g, yield=86%

Distillation of Sample A demonstrates the feasibility of distilling CBC as a purification method to avoid flash column chromatography, especially for the future product at large scales.

Example 2: Distillation Study

Purpose: To evaluate the feasibility of using distillation (a scale-up friendly process option) as the purification method for CBC synthesis. (Liturature J. Chem. SOC. (C), 1971, page 796: Reported BP 170° C. at 100 mtorr (133 mbar)).

Material: Crude CBC sample A above 9.0 g.

Procedure: At full vacuum (no meter was available, assume 0 mbar), gradually increased temperature as follows: 190° C. (thermo set at 190° C. and 2 L scale with a small heating mantle); increased temperature to 203° C.-205° C. (thermo set at 205° C. and 2 L scale with a small heating mantle). Bright yellow oil (7.5 g) distillates were collected.

Figure 2:
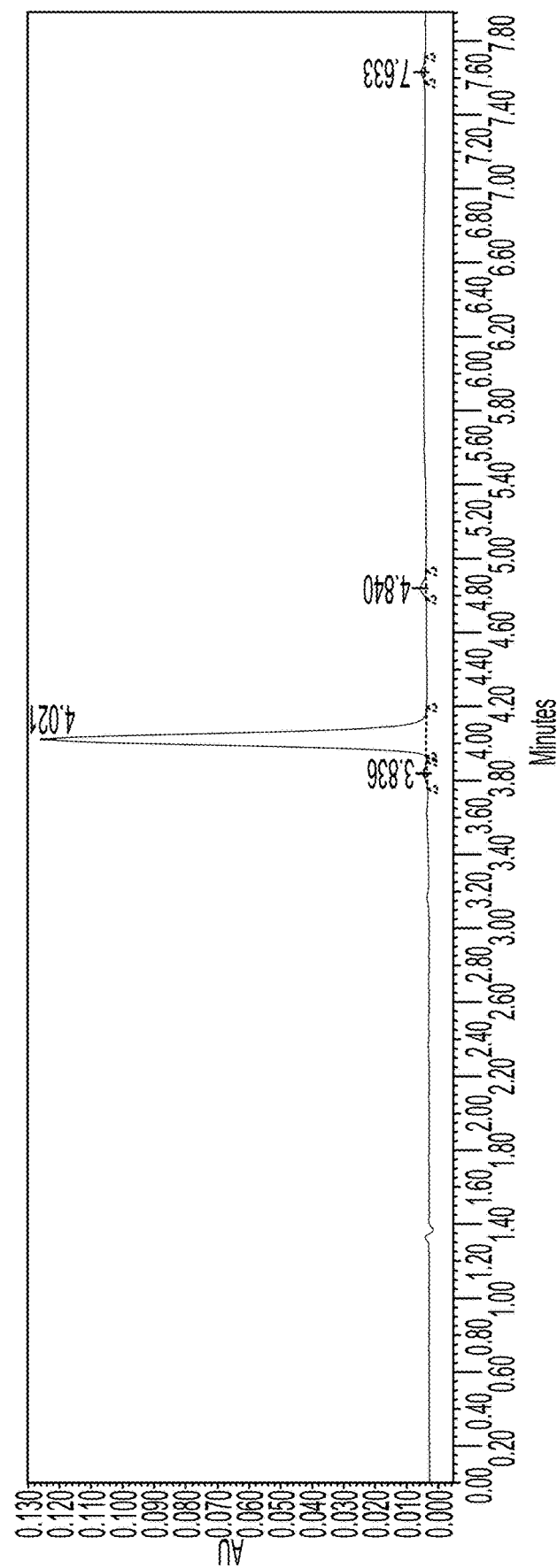
FIG. 2 depicts a HPLC chromatogram of the CBC reaction as described in Example 2.

The product HPLC data are shown in FIG. 2 and Table 2.

TABLE 2

| | Name | Retention Time | Area | % Area | Height |
|---|---|---|---|---|---|
| 1 | Unknown | 3.838 | 392 | 0.44 | 141 |
| 2 | CBC | 4.021 | 87345 | 99.01 | 19565 |
| 3 | Unknown | 4.840 | 250 | 0.28 | 123 |
| 4 | CBC Dimer | 7.633 | 230 | 0.26 | 104 |

Example 3: Preparation of Cannabichrome; Citral 1.09 Eq.

Materials:
Citral (cis+trans) 95%; Alfa-Aesar, Lot #10220684; MW: 152.24 g/mo, D=0.888 g/mL; exp: Oct. 4, 2022

Ethyelenediamine 99% (vendor: Alfa-Aesar, Lot #S22E009), MW: 60.10 g/mol; D=0.899 g/mL; exp: Jan. 2, 2022

Non-anhydrous Toluene; VWR Chemicals; Lot #18D104019; Exp: Apr. 3, 2022.

Olivetol; Vendor: SCI pharmtech inc; Lot #1805P122; Exp: Feb. 18, 2024; NC370

Procedure:
A EasyMax reactor (50 mL) equipped with a reflux condenser was loaded with olivetol (2.70 g, 15.0 mmol, 1.00 equiv.), Toluene (33 mL), and ethylenediamine (200 μL, 3.00 mmol, 20 mol %). Then the solution was heated to 100° C. (Note: The reaction turned cloudy when ethylenediamine was added. The solution turned clear while heating to 100° C.)

Next, citral (2.80 mL, 16.35 mmol, 1.09 equiv.) in Toluene (8.17 mL) was added over a ten minute period. (Note: The reaction bubbled during this time.)

The reaction mixture was stirred at 100° C. for 30 minutes (Note: The reaction was no longer bubbling after ~5 minutes.). After the allotted time, the reaction mixture was cooled to 20° C.

Conversion: 88.15%

Figure 3:
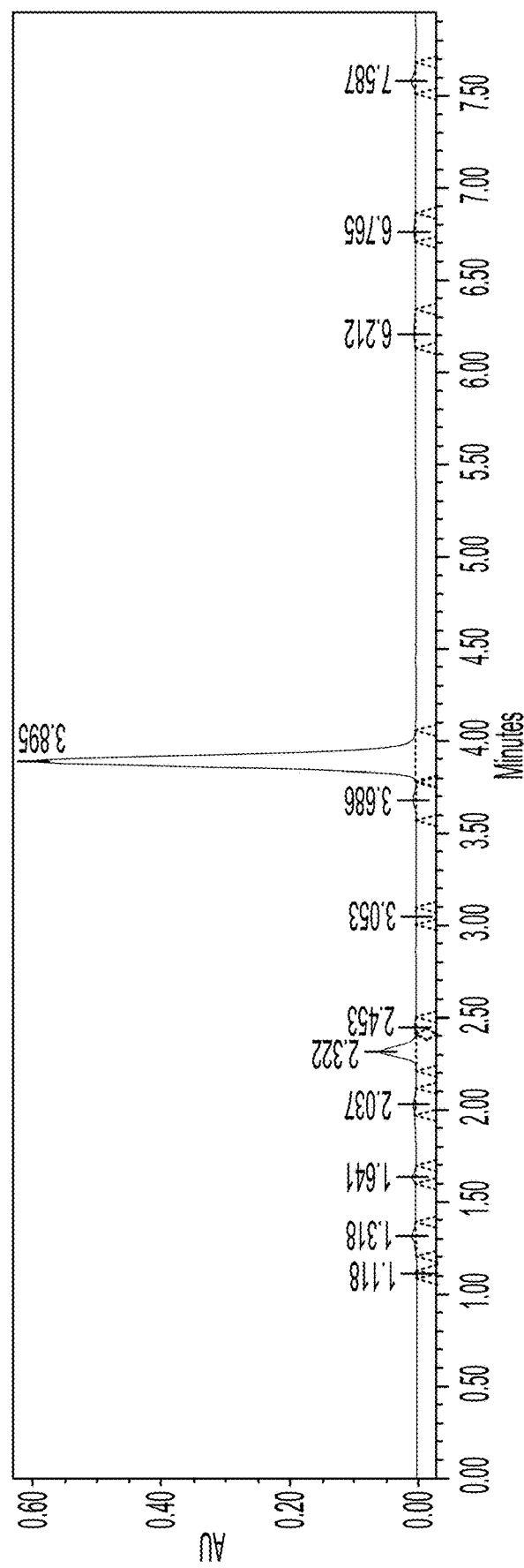
FIG. 3 depicts a HPLC chromatogram of the CBC reaction as described in Example 3.

The product HPLC data are shown in FIG. 3 and Table 3.

TABLE 3

| | Retention Time | Area | % Area | Height |
|---|---|---|---|---|
| 1 | 1.118 | 54 | 0.00 | 35 |
| 2 | 1.318 | 29003 | 0.95 | 6523 |
| 3 | 1.641 | 14370 | 0.47 | 5350 |
| 4 | 2.037 | 12588 | 0.41 | 3379 |
| 5 | 2.322 | 218824 | 7.21 | 54751 |
| 6 | 2.453 | 7742 | 0.25 | 2174 |
| 7 | 3.053 | 169 | 0.01 | 70 |
| 8 | 3.686 | 22107 | 0.73 | 4798 |
| 9 | 3.895 | 2677302 | 88.15 | 595727 |
| 10 | 6.212 | 14642 | 0.48 | 2264 |
| 11 | 6.765 | 12187 | 0.40 | 2353 |
| 12 | 7.587 | 28100 | 0.93 | 6828 |

Example 4: Preparation of Cannabichrome; Citral 1.00 Eq.

Procedure:
A EasyMax reactor (50 mL) equipped with a reflux condenser was loaded with olivetol (2.70 g, 15.0 mmol, 1.00 equiv.), Toluene (33 mL), and ethylenediamine (200 μL, 3.00 mmol, 20 mol %). Then the solution was heated to 100° C. (Note: The reaction turned cloudy when ethylenediamine was added. The solution turned clear while heating to 100° C.)

Next, citral (2.57 mL, 15.00 mmol, 1.00 equiv.) in Toluene (7.35 mL) was added over a ten minute period. (Note: The reaction bubbled during this time.)

The reaction mixture was stirred at 100° C. for 30 minutes (Note: The reaction was no longer bubbling after ~5 minutes.). After the allotted time, the reaction mixture was cooled to 20° C.

Conversion: 89.53%

Figure 4:
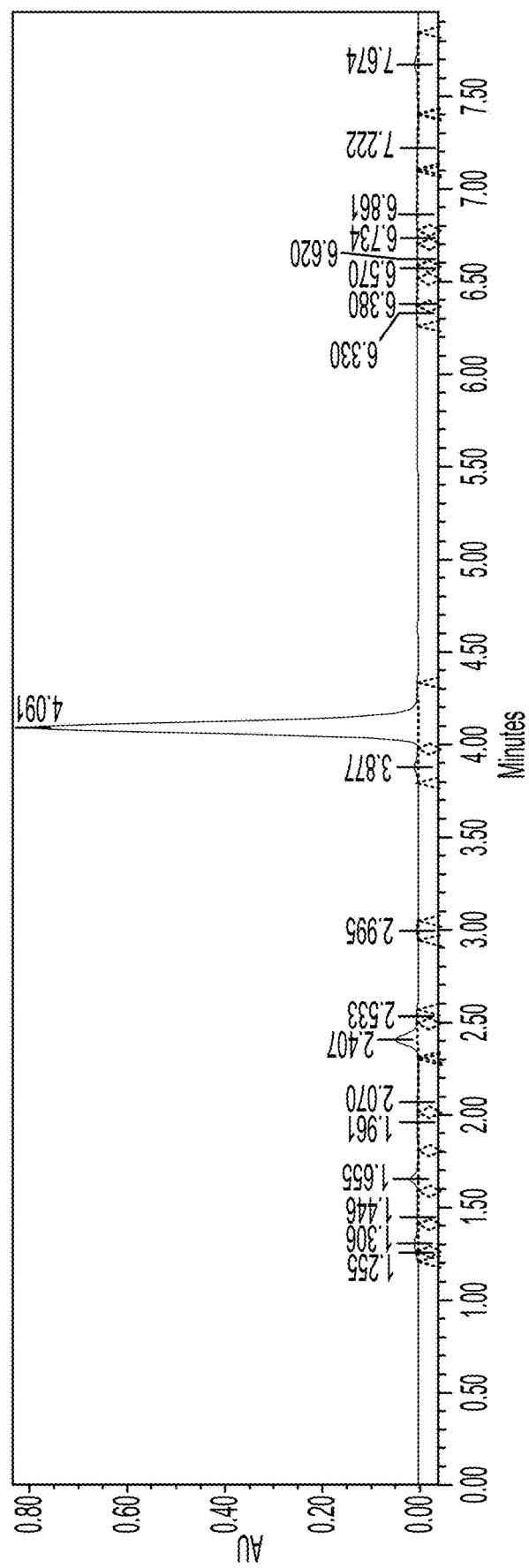
FIG. 4 depicts a HPLC chromatogram of the CBC reaction as described in Example 4.

The product HPLC data are shown in FIG. 4 and Table 4.

TABLE 4

|  | Retention Time | Area | % Area | Height |
|---|---|---|---|---|
| 1 | 1.255 | 7981 | 0.20 | 3841 |
| 2 | 1.306 | 32144 | 0.81 | 7272 |
| 3 | 1.446 | 7681 | 0.19 | 873 |
| 4 | 1.655 | 50423 | 1.28 | 15679 |
| 5 | 1.961 | 11907 | 0.30 | 1827 |
| 6 | 2.070 | 9478 | 0.24 | 1806 |
| 7 | 2.407 | 185206 | 4.69 | 45501 |
| 8 | 2.533 | 5139 | 0.13 | 1864 |
| 9 | 2.995 | 5664 | 0.14 | 1596 |
| 10 | 3.877 | 30790 | 0.78 | 6535 |
| 11 | 4.091 | 3535125 | 89.53 | 792499 |
| 12 | 6.330 | 7775 | 0.20 | 1718 |
| 13 | 6.380 | 5915 | 0.15 | 1559 |
| 14 | 6.570 | 854 | 0.02 | 334 |
| 15 | 6.620 | 2079 | 0.05 | 432 |
| 16 | 6.734 | 619 | 0.02 | 165 |
| 17 | 6.861 | 16883 | 0.43 | 3014 |
| 18 | 7.222 | 2103 | 0.05 | 356 |
| 19 | 7.674 | 30785 | 0.78 | 6907 |

Example 5: Preparation of Cannabichrome; Citral 0.95 Eq.

Procedure:

A EasyMax reactor (50 mL) equipped with a reflux condenser was loaded with olivetol (2.70 g, 15.0 mmol, 1.00 equiv.), Toluene (33 mL), and ethylenediamine (200 µL, 3.00 mmol, 20 mol %). Then the solution was heated to 100° C. (Note: The reaction turned cloudy when ethylenediamine was added. The solution turned clear while heating to 100° C.)

Next, citral (2.44 mL, 14.25 mmol, 0.95 equiv.) in Toluene (6.98 mL) was added over a ten minute period. (Note: The reaction bubbled during this time.)

The reaction mixture was stirred at 100° C. for 30 minutes (Note: The reaction was no longer bubbling after ~5 minutes.). After the allotted time, the reaction mixture was cooled to 20° C.

Conversion: 90.64%

Figure 5:
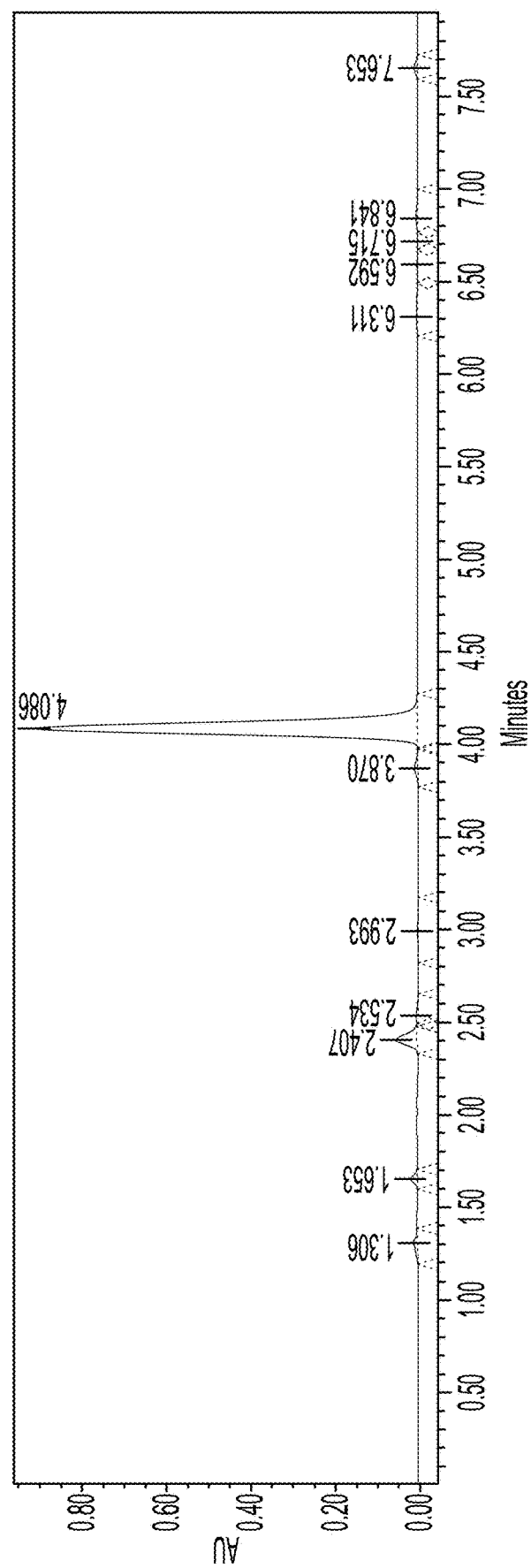
FIG. 5 depicts a HPLC chromatogram of the CBC reaction as described in Example 5.

The product HPLC data are shown in FIG. 5 and Table 5.

TABLE 5

|  | Retention Time | Area | % Area | Height |
|---|---|---|---|---|
| 1 | 1.306 | 43170 | 0.97 | 8391 |
| 2 | 1.653 | 46550 | 1.04 | 16329 |
| 3 | 2.407 | 192383 | 4.31 | 49453 |
| 4 | 2.534 | 19063 | 0.43 | 4303 |
| 5 | 2.993 | 9310 | 0.21 | 2035 |
| 6 | 3.870 | 34431 | 0.77 | 7443 |
| 7 | 4.086 | 4047071 | 90.64 | 909862 |
| 8 | 6.311 | 19262 | 0.43 | 2357 |
| 9 | 6.592 | 4034 | 0.09 | 537 |
| 10 | 6.715 | 1280 | 0.03 | 250 |
| 11 | 6.841 | 19497 | 0.44 | 3554 |
| 12 | 7.653 | 28880 | 0.65 | 7463 |

Example 6: Preparation of Cannabichrome; Citral 0.95 Eq.

Procedure:

A EasyMax reactor (50 mL) equipped with a reflux condenser was loaded with olivetol (2.70 g, 15.0 mmol, 1.00 equiv.), Toluene (33 mL), and ethylenediamine (200 µL, 3.00 mmol, 20 mol %). Then the solution was heated to 100° C. (Note: The reaction turned cloudy when ethylenediamine was added. The solution turned clear while heating to 100° C.)

Next, citral (3.03 mL, 17.7 mmol, 1.18 equiv.) in Toluene (8.67 mL) was added over a ten minute period. (Note: The reaction bubbled during this time.)

The reaction mixture was stirred at 100° C. for 30 minutes (Note: The reaction was no longer bubbling after ~5 minutes.). After the allotted time, the reaction mixture was cooled to 20° C.

Conversion: 82.56%

Figure 6:
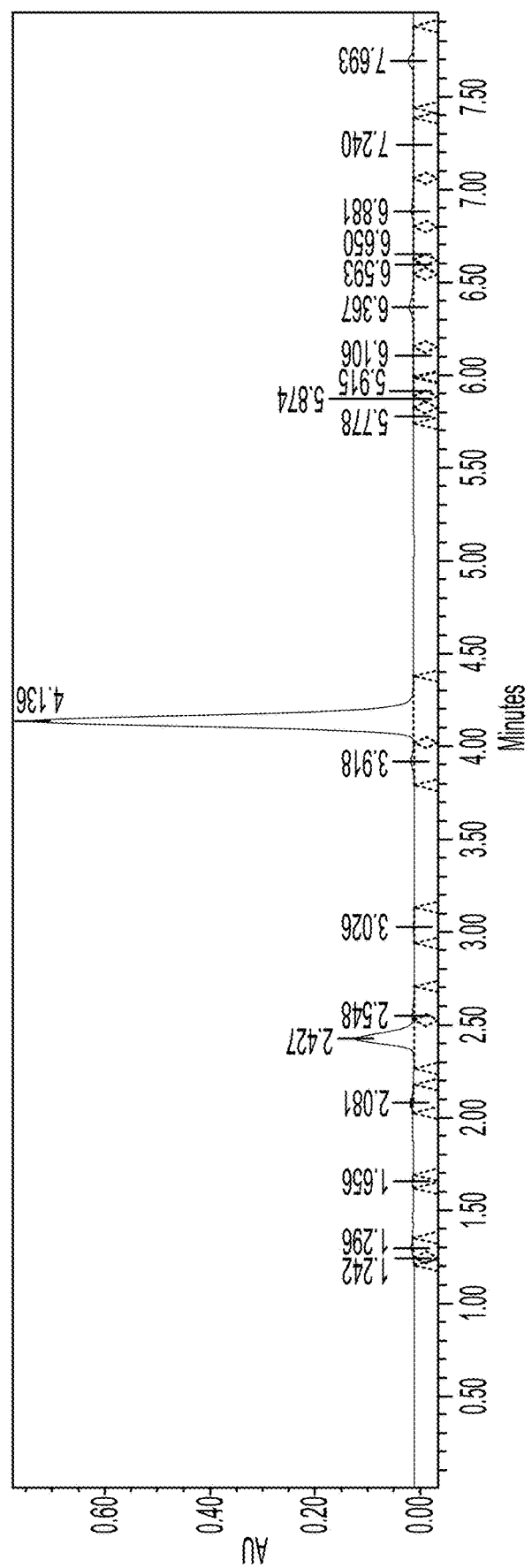
FIG. 6 depicts a HPLC chromatogram of the CBC reaction as described in Example 6.

The product HPLC data are shown in FIG. 6 and Table 6.

TABLE 6

|  | Retention Time | Area | % Area | Height |
|---|---|---|---|---|
| 1 | 1.242 | 1379 | 0.03 | 858 |
| 2 | 1.296 | 13808 | 0.35 | 3933 |
| 3 | 1.656 | 7561 | 0.19 | 3080 |
| 4 | 2.081 | 17947 | 0.45 | 4954 |
| 5 | 2.427 | 469128 | 11.82 | 112003 |
| 6 | 2.548 | 15120 | 0.38 | 3605 |
| 7 | 3.026 | 4679 | 0.12 | 1004 |
| 8 | 3.918 | 27397 | 0.69 | 5794 |
| 9 | 4.136 | 3277468 | 82.56 | 735894 |
| 10 | 5.778 | 966 | 0.02 | 280 |
| 11 | 5.874 | 674 | 0.02 | 216 |
| 12 | 5.915 | 948 | 0.02 | 245 |
| 13 | 6.106 | 1284 | 0.03 | 219 |
| 14 | 6.367 | 50783 | 1.28 | 7598 |
| 15 | 6.593 | 2508 | 0.06 | 661 |
| 16 | 6.650 | 5010 | 0.13 | 705 |
| 17 | 6.881 | 25134 | 0.63 | 4427 |
| 18 | 7.240 | 2147 | 0.05 | 240 |
| 19 | 7.693 | 45948 | 1.16 | 10436 |

Example 7: Preparation of Cannabichrome; Lower Conversion

Materials:

Citral (cis+trans) 95% (Vendor: Alfa-Aesar, Lot: 10213379), MW: 152.24 g/mo, D=0.888 g/mL.

Ethyelenediamine 99% (vendor: Alfa-Aesar, Lot: S22E009), MW: 60.10 g/mol; D=0.899 g/mL.

Toluene; Vendor: VWR Chemicals; Lot:18D104019; Exp: Apr. 22, 2011.

Olivetol; Vendor: SCI pharmtech inc; Lot: 1805P122; Exp: Feb. 18, 2024.

Heptane 99%: Brenntag; lot: T30C2L; exp: Mar. 14, 2022

Celite 545; Lot: 11EW05170; from SSPF; Exp: Apr. 22, 2029

Procedure: A 2-neck round bottom flask (2 L) equipped with a reflux condenser was loaded with olivetol (20.2 g, 112.0 mmol, 1 equiv.), Toluene (250 mL), and citral (21.0 mL, 122.8 mmol, 1.09 equiv). Next, ethylenediamine (1.5 mL, 22.4 mmol, 20 mol %) was added to the reaction dropwise while stirring. The resulting solution was stirred at reflux while being monitored by HPLC analysis. After 4 hours, the reaction showed no further signs of consuming the remaining olivetol. The reaction mixture was then allowed to cooled to room temperature. Next, the reaction mixture was filtered through a pad of celite and the solvent was removed by roto evaporation. The reaction mixture was then purified by FCC using an increasing gradient of 15 to 5000 DCM/heptane. The collected fractions were then combined and the solvent was removed by roto evaporation. Collected 19.8 g of a yellow oil (93.3% o purity).

Conversion: 66.85%

Figure 7:
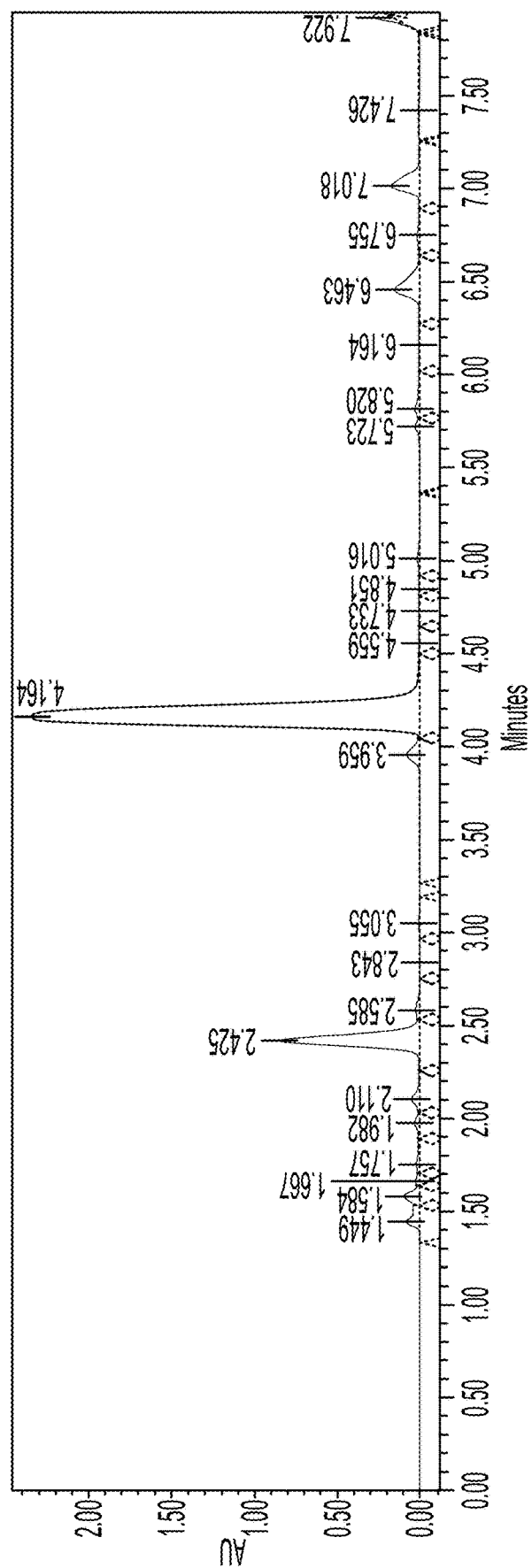
FIG. 7 depicts a HPLC chromatogram of the CBC reaction as described in Example 7.

The crude reaction mixture TIPLC data are shown in FIG. 7 and Table 7.

TABLE 7

| | Retention Time | Area | % Area | Height |
|---|---|---|---|---|
| 1 | 1.449 | 383066 | 1.51 | 81235 |
| 2 | 1.584 | 359643 | 1.42 | 95326 |
| 3 | 1.667 | 78999 | 0.31 | 23569 |
| 4 | 1.757 | 134031 | 0.53 | 17563 |
| 5 | 1.982 | 146627 | 0.58 | 30897 |
| 6 | 2.110 | 246062 | 0.97 | 48970 |
| 7 | 2.425 | 3615456 | 14.30 | 848231 |
| 8 | 2.585 | 143725 | 0.57 | 23411 |
| 9 | 2.843 | 20961 | 0.08 | 2716 |
| 10 | 3.055 | 35135 | 0.14 | 6812 |
| 11 | 3.959 | 419290 | 1.66 | 78384 |
| 12 | 4.164 | 16905936 | 66.85 | 2341472 |
| 13 | 4.559 | 28276 | 0.11 | 3420 |
| 14 | 4.733 | 36719 | 0.15 | 4799 |
| 15 | 4.851 | 16645 | 0.07 | 3020 |
| 16 | 5.016 | 81560 | 0.32 | 13040 |
| 17 | 5.723 | 106882 | 0.42 | 24500 |
| 18 | 5.820 | 163091 | 0.64 | 26931 |
| 19 | 6.164 | 44643 | 0.18 | 4029 |
| 20 | 6.463 | 958667 | 3.79 | 151918 |
| 21 | 6.755 | 89046 | 0.35 | 10645 |
| 22 | 7.018 | 915313 | 3.62 | 168417 |
| 23 | 7.426 | 55096 | 0.22 | 2544 |
| 24 | 7.922 | 306100 | 1.21 | 117384 |

Example 8: Preparation of Cannabichrome; Lower Conversion

Procedure: Next, ethylenediamine (1.5 mL, 22.4 mmol, 20 mol %) was added to the reaction dropwise while stirring. The resulting solution was stirred at reflux while being monitored by HPLC analysis. After 4 hours, the reaction showed no further signs of consuming the remaining olivetol. The reaction mixture was then allowed to cooled to room temperature. Next, the reaction mixture was filtered through a pad of celite and the solvent was removed by roto evaporation. The reaction mixture was then purified by FCC using an increasing gradient of 15 to 50% DCM/heptane. The collected fractions were then combined and the solvent was removed by roto evaporation.

Conversion: 76.06%

Figure 8:
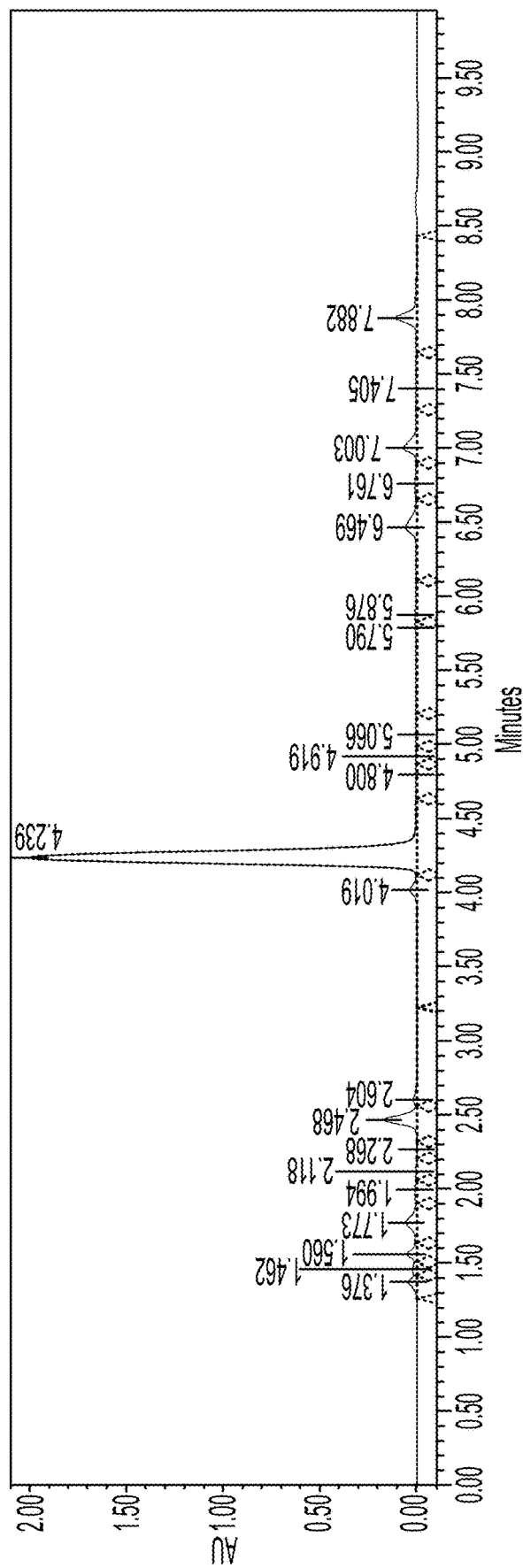
FIG. 8 depicts a HPLC chromatogram of the CBC reaction as described in Example 8.

The crude reaction mixture HPLC data are shown in FIG. 8 and Table 8.

TABLE 8

| | Retention Time | Area | % Area | Height |
|---|---|---|---|---|
| 1 | 1.376 | 177199 | 1.21 | 42364 |
| 2 | 1.462 | 89073 | 0.61 | 21185 |
| 3 | 1.560 | 183000 | 1.25 | 48592 |
| 4 | 1.773 | 346875 | 2.36 | 54099 |
| 5 | 1.994 | 49252 | 0.34 | 8753 |
| 6 | 2.118 | 16725 | 0.11 | 3171 |
| 7 | 2.268 | 5280 | 0.04 | 1072 |
| 8 | 2.468 | 705638 | 4.81 | 169618 |
| 9 | 2.604 | 80618 | 0.55 | 14615 |
| 10 | 4.019 | 188262 | 1.28 | 33949 |

TABLE 8-continued

| | Retention Time | Area | % Area | Height |
|---|---|---|---|---|
| 11 | 4.239 | 11160941 | 76.06 | 2007505 |
| 12 | 4.800 | 37836 | 0.26 | 3434 |
| 13 | 4.919 | 18665 | 0.13 | 3076 |
| 14 | 5.066 | 36048 | 0.25 | 4310 |
| 15 | 5.790 | 93580 | 0.64 | 6021 |
| 16 | 5.876 | 71236 | 0.49 | 6512 |
| 17 | 6.469 | 440674 | 3.00 | 54998 |
| 18 | 6.761 | 63902 | 0.44 | 6153 |
| 19 | 7.003 | 361787 | 2.47 | 65314 |
| 20 | 7.405 | 24985 | 0.17 | 2005 |
| 21 | 7.882 | 523192 | 3.57 | 106301 |

Example 9: Preparation of Cannabichrome; Lower Conversion

Procedure: A EasyMax reactor (125 mL) equipped with a reflux condenser was loaded with olivetol (2.70 g, 15.0 mmol, 1.00 equiv.), Toluene (33 mL), and citral (2.80 mL, 16.35 mmol, 1.09 equiv.). The reaction mixture was stirred (400 rpm) at 25° C. until the solution became clear. Next, ethylenediamine (200 µL, 3.00 mmol, 20 mol %) was added to the reaction mixture dropwise over a 2 minute period (Note: The solution turned to a cloudy light yellow color). The resulting reaction mixture was stirred at reflux (110° C.) while being monitored by HPLC analysis. After 3 hours, the reaction showed no further signs of consuming the remaining olivetol. The reaction mixture was then cooled to room temperature.

Conversion: 56.71%

Figure 9:
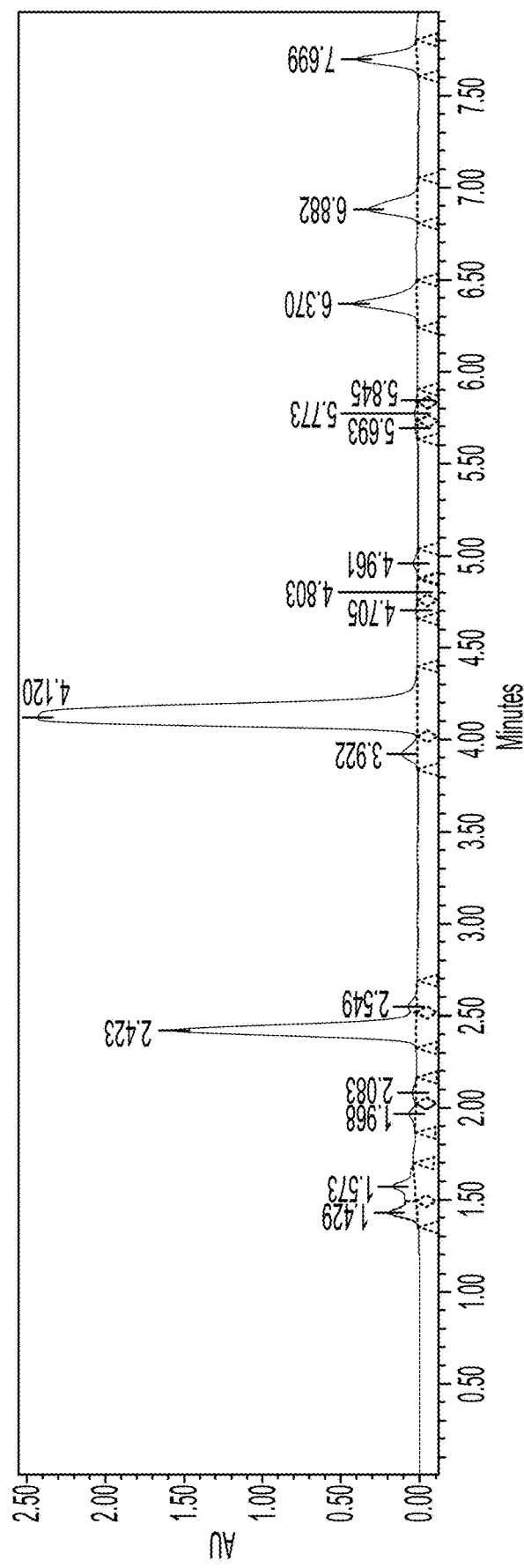
FIG. 9 depicts a HPLC chromatogram of the CBC reaction as described in Example 9.

The crude reaction mixture HPLC data are shown in FIG. 9 and Table 9.

TABLE 9

| | Retention Time | Area | % Area | Height |
|---|---|---|---|---|
| 1 | 1.429 | 730906 | 2.22 | 176077 |
| 2 | 1.573 | 757015 | 2.30 | 140645 |
| 3 | 1.968 | 176494 | 0.54 | 42837 |
| 4 | 2.083 | 105103 | 0.32 | 20870 |
| 5 | 2.423 | 6379072 | 19.37 | 1548813 |
| 6 | 2.549 | 206636 | 0.63 | 52365 |
| 7 | 3.922 | 501843 | 1.52 | 101213 |
| 8 | (CBC) 4.120 | 18613538 | 56.52 | 2420661 |
| 9 | 4.705 | 29151 | 0.09 | 7979 |
| 10 | 4.803 | 18165 | 0.06 | 4748 |
| 11 | 4.961 | 113086 | 0.34 | 27357 |
| 12 | 5.693 | 63107 | 0.19 | 18278 |
| 13 | 5.773 | 77464 | 0.24 | 20116 |
| 14 | 5.845 | 13715 | 0.04 | 5215 |
| 15 | 6.370 | 1956135 | 5.94 | 402809 |
| 16 | 6.882 | 1556413 | 4.73 | 313814 |
| 17 | 7.699 | 1634426 | 4.96 | 387292 |

Example 10: Preparation of Cannabichrome

Procedure: A EasyMax reactor (125 mL) equipped with a reflux condenser was loaded with olivetol (2.70 g, 15.0 mmol, 1.00 equiv.), Toluene (33 mL), and citral (2.80 mL, 16.35 mmol, 1.09 equiv.). The reaction mixture was stirred (400 rpm) at 25° C. until the solution became clear. Next, ethylenediamine (200 µL, 3.00 mmol, 20 mol %) was added to the reaction mixture dropwise over a 2 minute period (Note: The solution turned to a cloudy light yellow color). The resulting reaction mixture was stirred at reflux (110° C.) while being monitored by HPLC analysis. After 3 hours, the reaction showed no further signs of consuming the remaining olivetol. The reaction mixture was then cooled to room temperature.

Conversion: 53.66%

Figure 10:
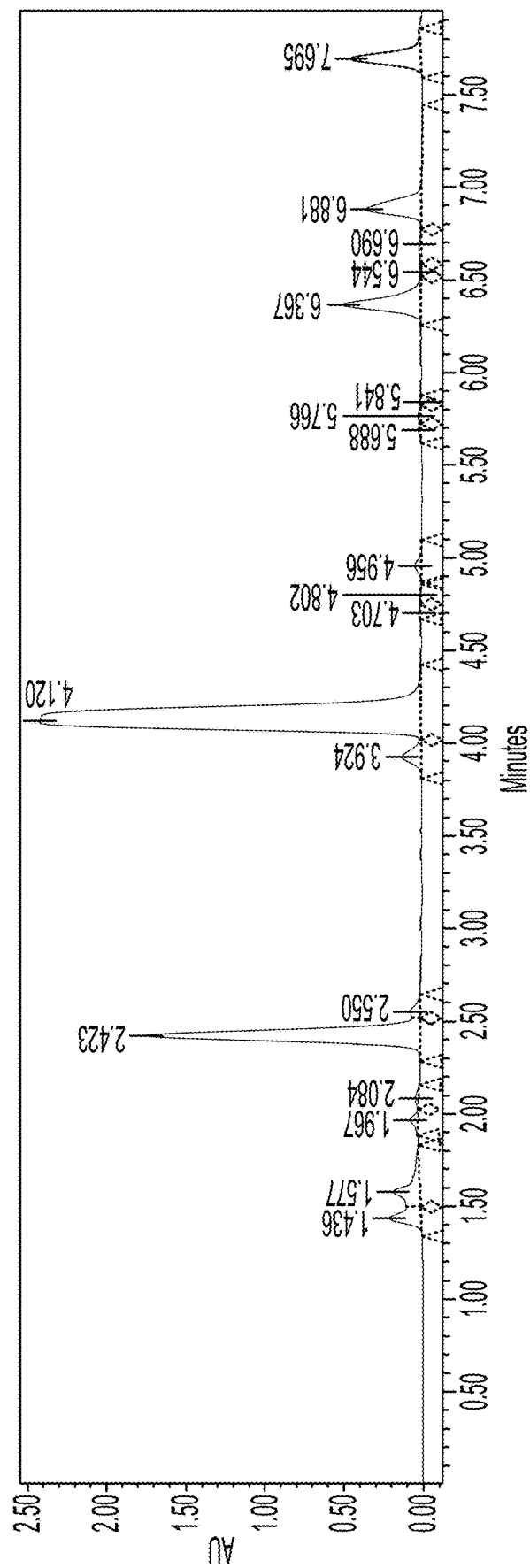
FIG. 10 depicts a HPLC chromatogram of the CBC reaction as described in Example 10.

The crude reaction mixture HPLC data are shown in FIG. 10 and Table 10.

TABLE 10

|    | Retention Time | Area     | % Area | Height  |
|----|----------------|----------|--------|---------|
| 1  | 1.436          | 870359   | 2.42   | 201707  |
| 2  | 1.577          | 1140706  | 3.17   | 168958  |
| 3  | 1.967          | 179525   | 0.50   | 49196   |
| 4  | 2.084          | 94517    | 0.26   | 19926   |
| 5  | 2.423          | 7263412  | 20.16  | 1734648 |
| 6  | 2.550          | 250104   | 0.69   | 61637   |
| 7  | 3.924          | 590106   | 1.64   | 119612  |
| 8  | (CBC) 4.120    | 19141794 | 53.13  | 2409827 |
| 9  | 4.703          | 13481    | 0.04   | 4880    |
| 10 | 4.802          | 12219    | 0.03   | 3717    |
| 11 | 4.956          | 162299   | 0.45   | 38629   |
| 12 | 5.688          | 50103    | 0.14   | 14677   |
| 13 | 5.766          | 60404    | 0.17   | 16233   |
| 14 | 5.841          | 6569     | 0.02   | 2874    |
| 15 | 6.367          | 2402650  | 6.67   | 491842  |
| 16 | 6.544          | 25225    | 0.07   | 6628    |
| 17 | 6.690          | 84913    | 0.24   | 10597   |
| 18 | 6.881          | 1787798  | 4.96   | 348060  |
| 19 | 7.695          | 1895371  | 5.26   | 441089  |

Example 11: Preparation of Cannabichrome

Procedure: A EasyMax reactor (125 mL) equipped with a reflux condenser was loaded with olivetol (2.70 g, 15.0 mmol, 1.00 equiv.), toluene (33 mL), and citral (2.80 mL, 16.35 mmol, 1.09 equiv.). The reaction mixture was stirred (400 rpm) at 25° C. until the solution became clear. Next, ethylenediamine (200 μL, 3.00 mmol, 20 mol %) was added to the reaction mixture dropwise over a 2 minute period (Note: The solution turned to a cloudy light yellow color). The resulting reaction mixture was stirred at reflux (110° C.) while being monitored by HPLC analysis. After 3 hours, the reaction showed no further signs of consuming the remaining olivetol. The reaction mixture was then cooled to room temperature.

Conversion: 53.66%

Figure 11:
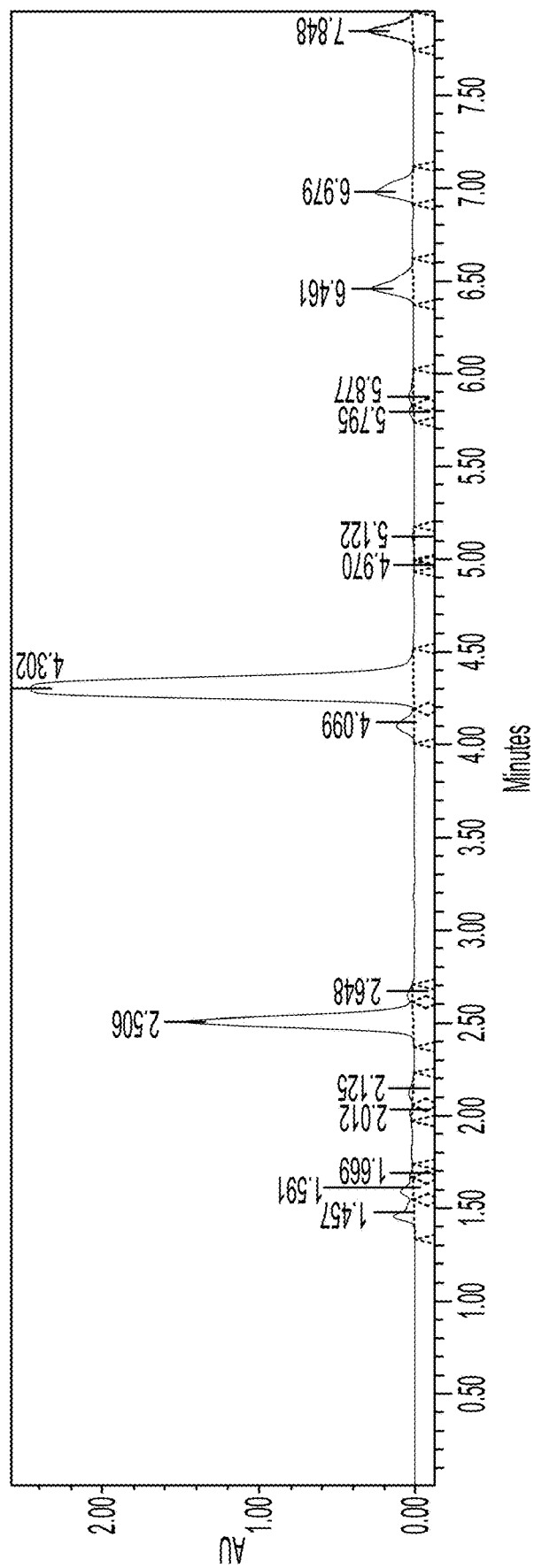
FIG. 11 depicts a HPLC chromatogram of the CBC reaction as described in Example 11.

The crude reaction mixture HPLC data are shown in FIG. 11 and Table 11.

TABLE 11

|    | Retention Time | Area     | % Area | Height  |
|----|----------------|----------|--------|---------|
| 1  | 1.457          | 531386   | 1.75   | 132045  |
| 2  | 1.591          | 333915   | 1.10   | 81464   |
| 3  | 1.669          | 38999    | 0.13   | 17560   |
| 4  | 2.012          | 31331    | 0.10   | 11641   |
| 5  | 2.125          | 125104   | 0.41   | 26324   |
| 6  | 2.506          | 6252753  | 20.57  | 1460857 |
| 7  | 2.648          | 116660   | 0.38   | 32322   |
| 8  | 4.099          | 557108   | 1.83   | 114325  |
| 9  | (CBC) 4.302    | 18200920 | 59.88  | 2443952 |
| 10 | 4.970          | 1040     | 0.00   | 529     |
| 11 | 5.122          | 37191    | 0.12   | 9406    |
| 12 | 5.795          | 95162    | 0.31   | 28818   |
| 13 | 5.877          | 167208   | 0.55   | 33742   |
| 14 | 6.461          | 1408913  | 4.64   | 262897  |
| 15 | 6.979          | 1262060  | 4.15   | 240136  |
| 16 | 7.848          | 1237065  | 4.07   | 279994  |

Example 12: Preparation of Cannabichromene

Figure 12:
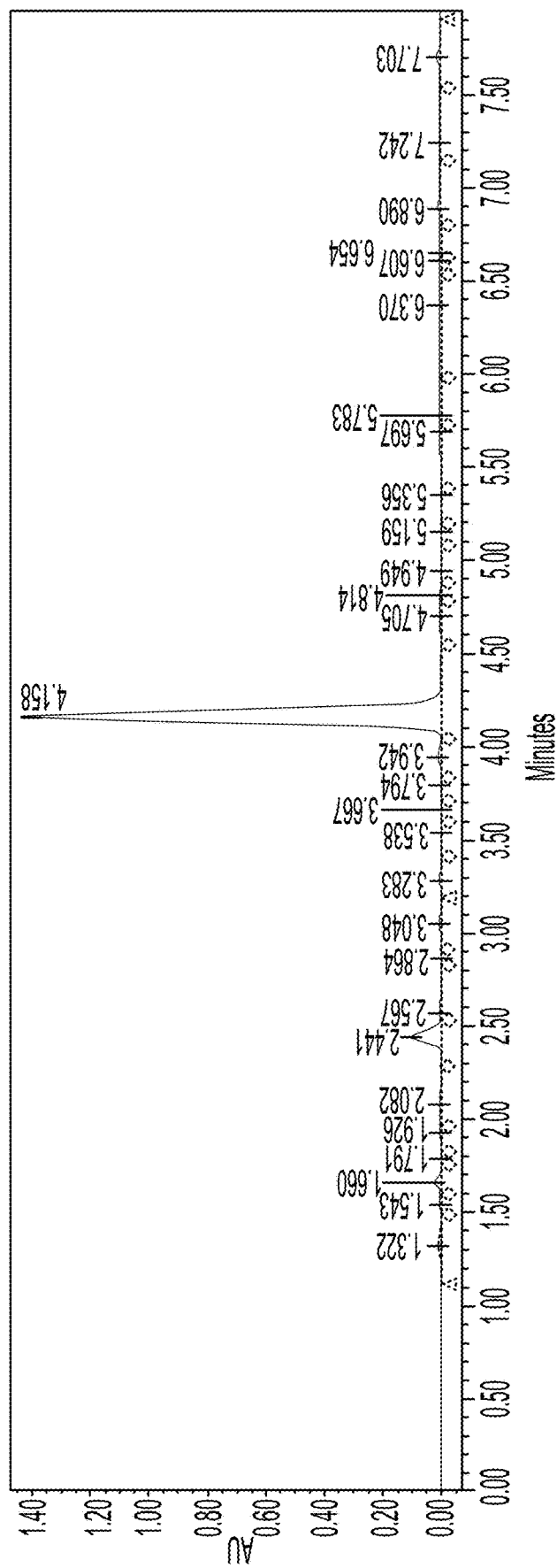
FIG. 12 depicts a HPLC chromatogram of the CBC reaction as described in Example 12.

Prepare a 2-neck round bottom flask (250 mL) equipped with a reflux condenser and nitrogen blanket. Charge olivetol (10.05 g, 56.0 mmol, 1.00 equiv.) Charge anhydrous toluene (125 mL). Charge ethylenediamine (0.67 g, 11.2 mmol, 20 mol %). Heat the reaction mixture to reflux. Charge citral (9.3 g, 61.4 mmol, 1.09 equiv.) toluene (30 mL) solution drop-wisely in 12 min. The reaction IPC (CBC at RT 4.19 min: 85.92%) is shown in FIG. 12.

Cooled the reaction mixture to 25° C. Washed the reaction mixture with water (155 mL×2). The top toluene/product layer was dried over sodium sulfate (15 g). Filtered off the drying reagent. Washed the cake with toluene (10 mL). Removed toluene using rotovap under vacuum at 60° C. to obtain a brown crude oil. Purified the crude oil using column chromatography with an increasing gradient of (100% n-Heptane, then 3% Ethyl acetate/n-Heptane, v/v). Three samples (A, B & C) were collected.

Figure 13:
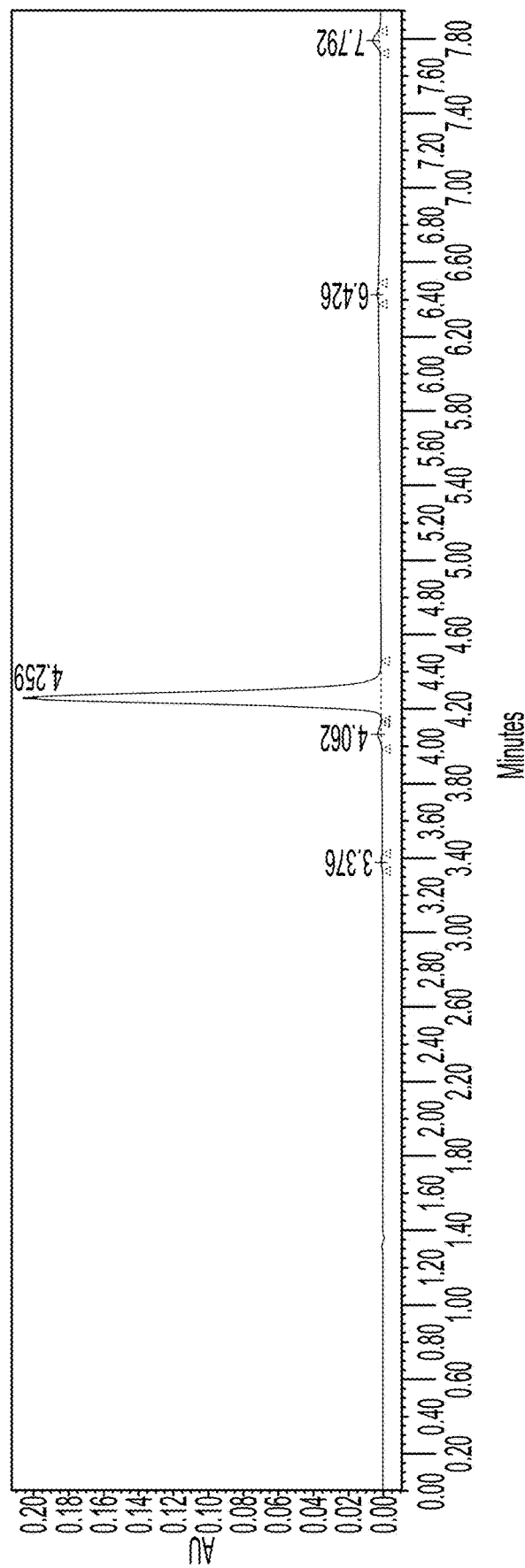
FIG. 13 depicts a HPLC chromatogram of the CBC reaction as described in Example 12.

Sample A (9.30 g, 97.20 area %) HPLC data shown in FIG. 13 and Table 12.

TABLE 12

|   | Name         | Retention Time | Area   | % Area | Height |
|---|--------------|----------------|--------|--------|--------|
| 1 | Unknown      | 3.376          | 1651   | 0.18   | 496    |
| 2 | Abnormal CBC | 4.062          | 7775   | 0.84   | 1863   |
| 3 | CBC          | 4.259          | 903008 | 97.20  | 201265 |
| 4 | Unknown      | 6.426          | 3033   | 0.33   | 856    |
| 5 | CBC dimmer   | 7.792          | 13559  | 1.46   | 3676   |

Figure 14:
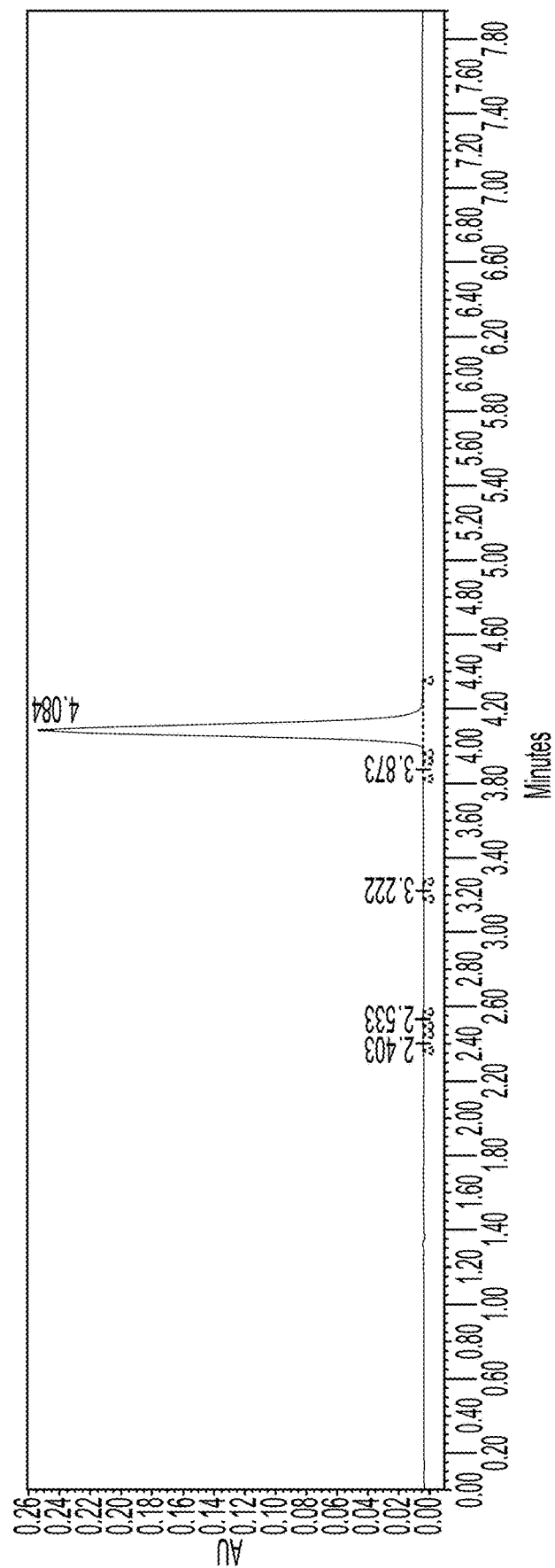
FIG. 14 depicts a HPLC chromatogram of the CBC reaction as described in Example 12.

Sample B (3.80 g, 99.46 area %) HPLC is shown in FIG. 14 and Table 13.

TABLE 13

|   | Name         | Retention Time | Area    | % Area | Height |
|---|--------------|----------------|---------|--------|--------|
| 1 | Unknown      | 2.403          | 995     | 0.09   | 334    |
| 2 | Unknown      | 2.533          | 1988    | 0.18   | 578    |
| 3 | Unknown      | 3.221          | 2362    | 0.22   | 569    |
| 4 | Abnormal CBC | 3.877          | 558     | 0.05   | 139    |
| 5 | CBC          | 4.084          | 1089120 | 99.46  | 244438 |

Figure 15:
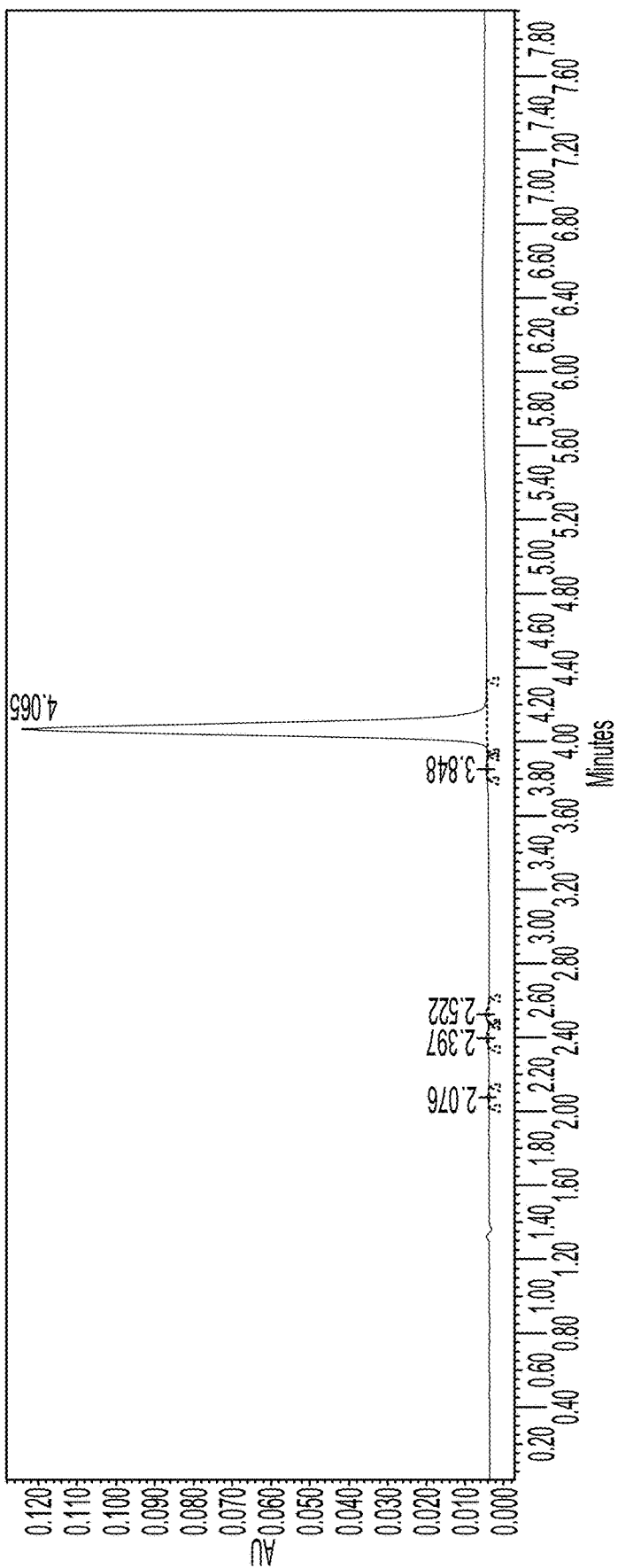
FIG. 15 depicts a HPLC chromatogram of the CBC reaction as described in Example 12.

Sample C (1.88 g, 98.56 area %) HPLC is shown in FIG. 15 and Table 14.

TABLE 14

|   | Name         | Retention Time | Area   | % Area | Height |
|---|--------------|----------------|--------|--------|--------|
| 1 | Unknown      | 2.076          | 1292   | 0.24   | 360    |
| 2 | Unknown      | 2.397          | 2520   | 0.47   | 689    |
| 3 | Unknown      | 2.522          | 2580   | 0.48   | 798    |
| 4 | Abnormal CBC | 3.848          | 1283   | 0.24   | 321    |
| 5 | CBC          | 4.065          | 524798 | 98.56  | 117926 |

Example 13: Distillation of Sample A

Figure 16:
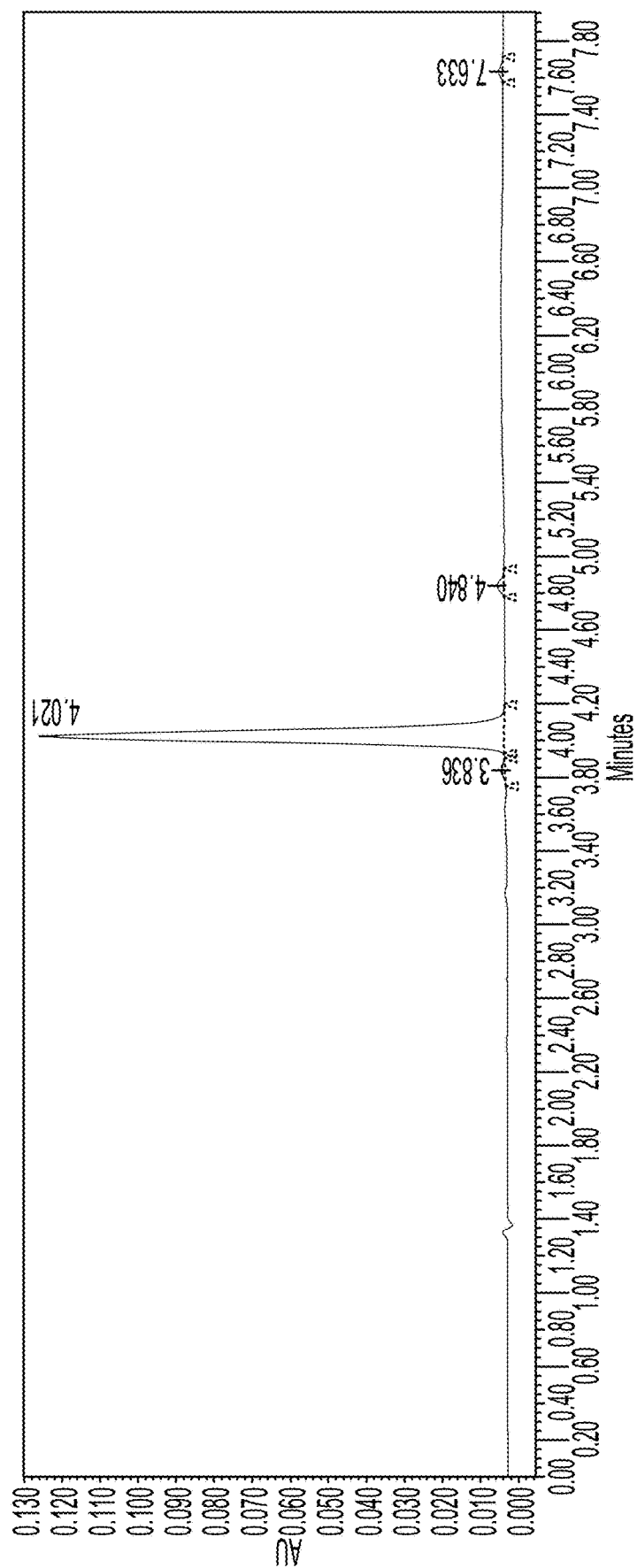
FIG. 16 depicts a HPLC chromatogram of the CBC reaction as described in Example 13.

The HPLC of CBC product after distillation is shown in FIG. 16 and Table 15.

TABLE 15

|   | Name    | Retention Time | Area  | % Area | Height |
|---|---------|----------------|-------|--------|--------|
| 1 | Unknown | 3.838          | 392   | 0.44   | 141    |
| 2 | CBC     | 4.021          | 87345 | 99.01  | 19565  |

TABLE 15-continued

| | Name | Retention Time | Area | % Area | Height |
|---|---|---|---|---|---|
| 3 | Unknown | 4.840 | 250 | 0.28 | 123 |
| 4 | CBC Dimer | 7.633 | 230 | 0.26 | 104 |

Example 14: Preparation of Cannabichromene; High Conversion

A reactor (2 L) equipped with a reflux condenser was loaded with olivetol (100 g, 0.554 mol, 1.00 equiv.), Toluene (1.23 L). Heat to 30° C. Ethylenediamine (7.4 mL, 0.110 mol, 20 mol %) was added once all of the olivetol was dissolved. (Note: While adding ethylenediamine, the temperature of the reaction increased to 29.5° C. from 30.7° C. and turned cloudy). Then the solution was heated to 100° C. (actual temperature: 99.3° C.) (Bath: 115.1° C.) (Note: The solution turned clear while heating to 100° C. (Bath: 115.1° C.).) Turned clear at 39.6° C. Next, citral (94.8 mL, 0.554 mol, 1.00 equiv.) in Toluene (270 mL) was added. (Note: Agitation speed 520 rpm. The reaction bubbled during this time.) Dose the citral solution to the reaction drop wisely. The reaction mixture was stirred at 100° C. for an additional 30 minutes. The reaction mixture was cooled to 20° C.

Figure 17:
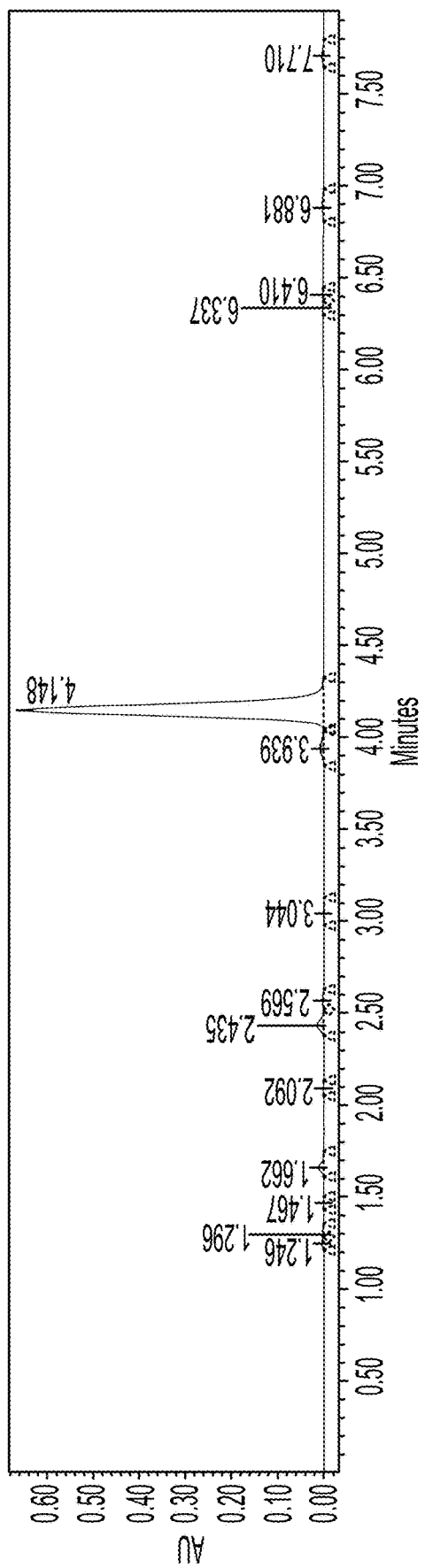
FIG. 17 depicts a HPLC chromatogram of the IPC of the CBC reaction as described in Example 14.

The reaction IPC (CBC at RT 4.148 min: 97.71%) is shown in FIG. 17.

Washed the reaction mixture with water (1.5 L×2). The organic phase was dried over sodium sulfate (150 g). Filtered off the drying reagent. To ⅔ of the product solution, add 275 g silica gel. Removed solvent to free flow silica/product powder (Note: Rotovap water bath set at 45C and reached 57C. Took about 1 hour to dry to free flow powder). Loaded 1 kg silica gel in a 3 L-frit funnel. Loaded the brown silica/product powder on top of the clean silica. Rinsed the silica gel pad with 3% EA/n-Heptane (v/v).

Figure 18:
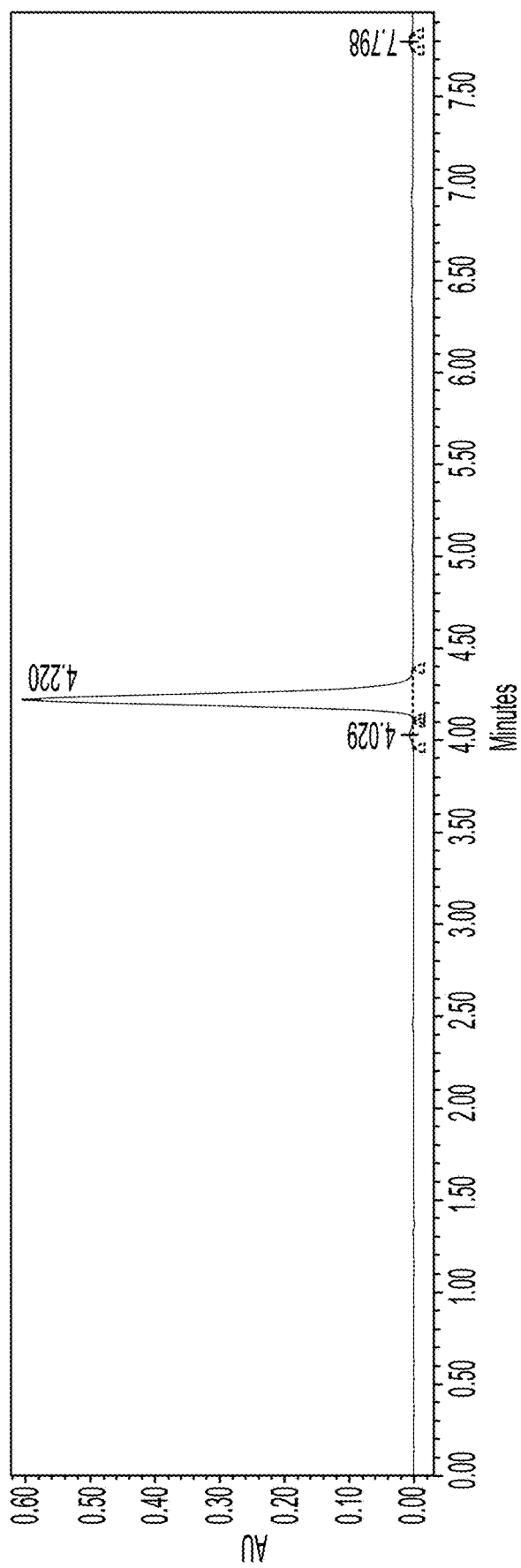
FIG. 18 depicts a HPLC chromatogram of the CBC reaction as described in Example 14.

Four samples were collected into 4X 4L Erlenmeyer flasks and HPLC indicated the almost all product was contained in the first 2 Erlenmeyer flasks. Removed the solvents in the first 2 Erlenmeyer flasks to afford pure CBC product (99.05%, see HPLC, FIG. 18 and Table 16).

TABLE 16

| | Name | Retention Time | Area | % Area | Height |
|---|---|---|---|---|---|
| 1 | Unknown | 4.029 | 17669 | 0.65 | 4555 |
| 2 | CBC | 4.220 | 2693610 | 99.05 | 592183 |
| 3 | CBC dimer | 7.796 | 8255 | 0.30 | 3108 |

Example 15: Preparation of Cannabicitran by Distillation

Figure 19:
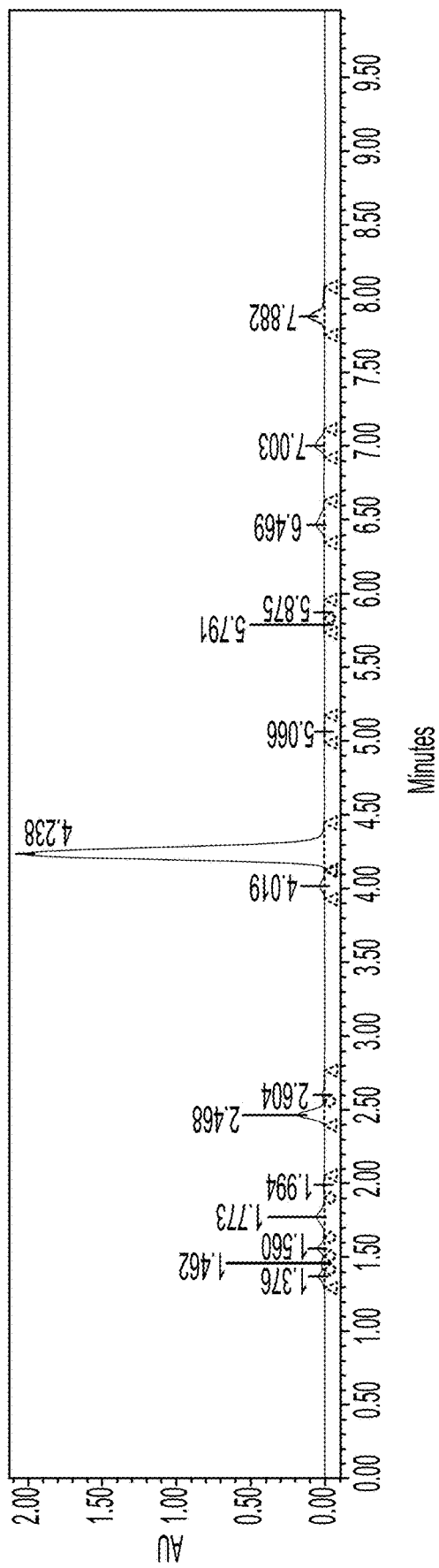
FIG. 19 depicts a HPLC chromatogram of the CBT reaction as described in Example 15.
Figure 20:
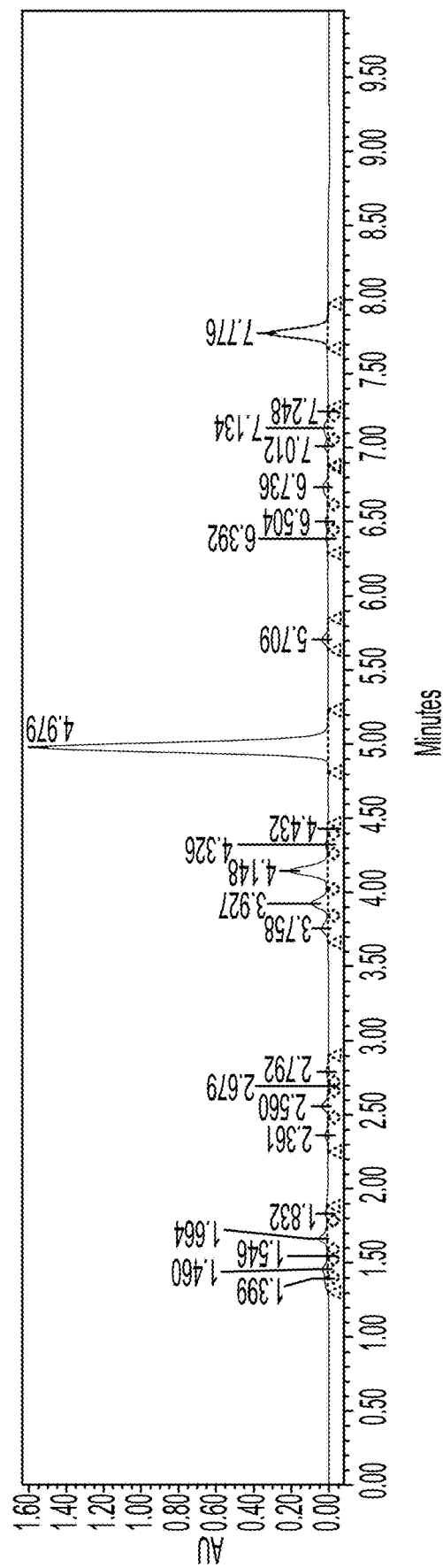
FIG. 20 depicts a HPLC chromatogram of the CBT reaction as described in Example 15.
Figure 21:
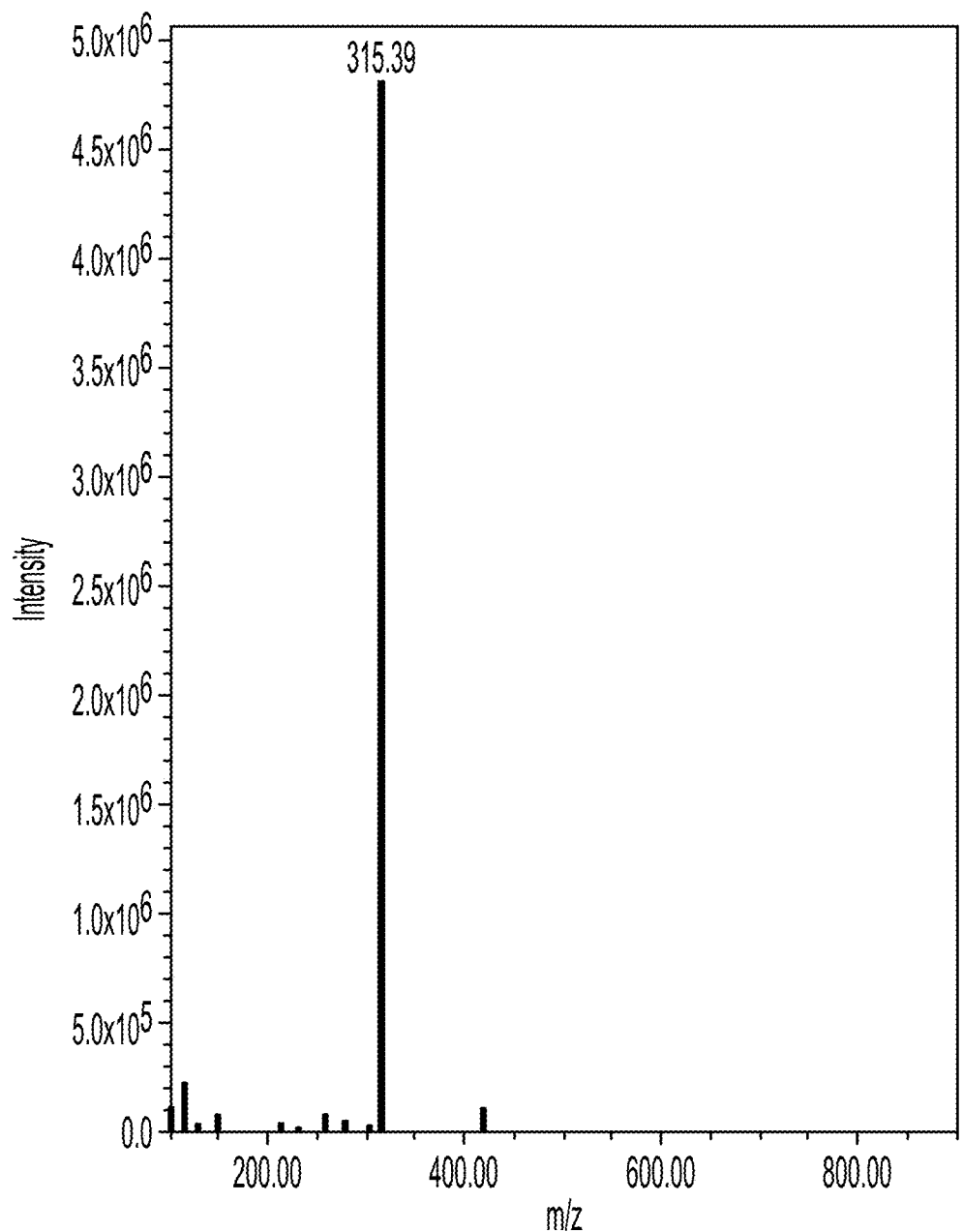
FIG. 21 depicts the Quadrupole Dalton mass spectra of CBT M+1 prepared from the experiment described in Example 15.

A 2-neck round bottom flask (2 L) equipped with a reflux condenser was loaded with olivetol (80.4 g, 448.0 mmol, 1.00 equiv.), Toluene (1 L), and citral (84.0 mL, 491.2 mmol, 1.09 equiv.). Next, ethylenediamine (6.0 mL, 89.6 mmol, 20 mol %) was added to the reaction dropwise while stirring. The resulting solution was stirred at reflux while being monitored by HPLC analysis. After 4 hours, the reaction showed no further signs of consuming the remaining olivetol. The reaction mixture was then cooled to room temperature. The reaction mixture was filtered through a pad of celite and solvent was removed by roto evap. The reaction mixture was then distilled under vacuum at 10.0 mbar. A yellow oil (92.0 g) started to come off at around 192° C. (Nomograph predicted the CBC compound coming off at 86.7° C.). An aliquot of the yellow oil was removed for HPLC analysis, HPLC showed the desired CBC compound decomposed into a new product (cannabicitran (CBT) 61.32% purity). HPLC before distillation is shown in FIG. 19 and Table 17. HPLC after distillation is shown in FIG. 20 and Table 18. FIG. 21 depicts the Quadrupole Dalton mass spectra of CBT M+1.

TABLE 17

| | Retention Time | Area | % Area | Height |
|---|---|---|---|---|
| 1 | 1.376 | 172189 | 1.22 | 43041 |
| 2 | 1.462 | 83754 | 0.60 | 20260 |
| 3 | 1.560 | 172171 | 1.22 | 47168 |
| 4 | 1.773 | 325406 | 2.31 | 53104 |
| 5 | 1.994 | 35791 | 0.25 | 7372 |
| 6 | 2.468 | 732258 | 5.21 | 181518 |
| 7 | 2.604 | 54662 | 0.39 | 12643 |
| 8 | 4.019 | 144709 | 1.03 | 32264 |
| 9 | (CBC) 4.238 | 11190832 | 79.57 | 2024907 |
| 10 | 5.066 | 9497 | 0.07 | 2305 |
| 11 | 5.791 | 11176 | 0.08 | 3156 |
| 12 | 5.875 | 11390 | 0.08 | 3022 |
| 13 | 6.469 | 321704 | 2.29 | 52760 |
| 14 | 7.003 | 308854 | 2.20 | 61800 |
| 15 | 7.882 | 490497 | 3.49 | 106232 |

TABLE 18

| | Retention Time | Area | % Area | Height |
|---|---|---|---|---|
| 1 | 1.399 | 70344 | 0.61 | 17473 |
| 2 | 1.460 | 127314 | 1.11 | 27614 |
| 3 | 1.546 | 16253 | 0.14 | 4977 |
| 4 | 1.664 | 178910 | 1.55 | 44728 |
| 5 | 1.832 | 28183 | 0.24 | 9490 |
| 6 | 2.361 | 76981 | 0.67 | 15316 |
| 7 | 2.560 | 146362 | 1.27 | 35920 |
| 8 | 2.697 | 7731 | 0.07 | 2365 |
| 9 | 2.792 | 53396 | 0.46 | 10361 |
| 10 | 3.758 | 166224 | 1.44 | 35271 |
| 11 | 3.927 | 425009 | 3.69 | 89836 |
| 12 | (CBC) 4.148 | 947667 | 8.23 | 202705 |
| 13 | 4.326 | 48199 | 0.42 | 11899 |
| 14 | 4.432 | 4820 | 0.04 | 1580 |
| 15 | (CBT) 4.979 | 7227420 | 62.75 | 1554124 |
| 16 | 5.709 | 131258 | 1.14 | 32544 |
| 17 | 6.392 | 39721 | 0.34 | 9723 |
| 18 | 6.504 | 57529 | 0.50 | 15215 |
| 19 | 6.736 | 144586 | 1.26 | 26807 |
| 20 | 7.012 | 69414 | 0.60 | 19318 |
| 21 | 7.134 | 123734 | 1.07 | 22363 |
| 22 | 7.248 | 3067 | 0.03 | 1321 |
| 23 | 7.776 | 1423361 | 12.36 | 327684 |

Example 16: Preparation of Cannabicitran by Distillation

A reactor (2 L) equipped with a reflux condenser was loaded with olivetol (100 g, 0.554 mol, 1.00 equiv.), Toluene (1.23 L). Heat to 30° C. Ethylenediamine (7.4 mL, 0.110 mol, 20 mol %) was added once all of the olivetol was dissolved. (Note: While adding ethylenediamine, the temperature of the reaction increased to 31.6° C. from 27.4° C. and turned cloudy). Then the solution was heated to 100° C. Next, citral (94.8 mL, 0.554 mol, 1.00 equiv.) in Toluene (270 mL) was added with an agitation speed of 520 rpm. (Note: The reaction bubbled during this time.) After the addition of citral solution ended, the reaction mixture was stirred at 100° C. for 30 minutes. After the allotted time, the reaction mixture was cooled to 20° C. Once the solution reached the desired temperature, the reaction mixture was washed with water (1.5 L×2) agitation (380 rpm). The organic phase was then collected and dried over sodium sulfate (150 g). The organic phase was filtered through a fritted funnel and the sodium sulfate was washed with another 100 mL of toluene. The solvent was then removed by rotary evaporation and dried overnight.

Figure 22:
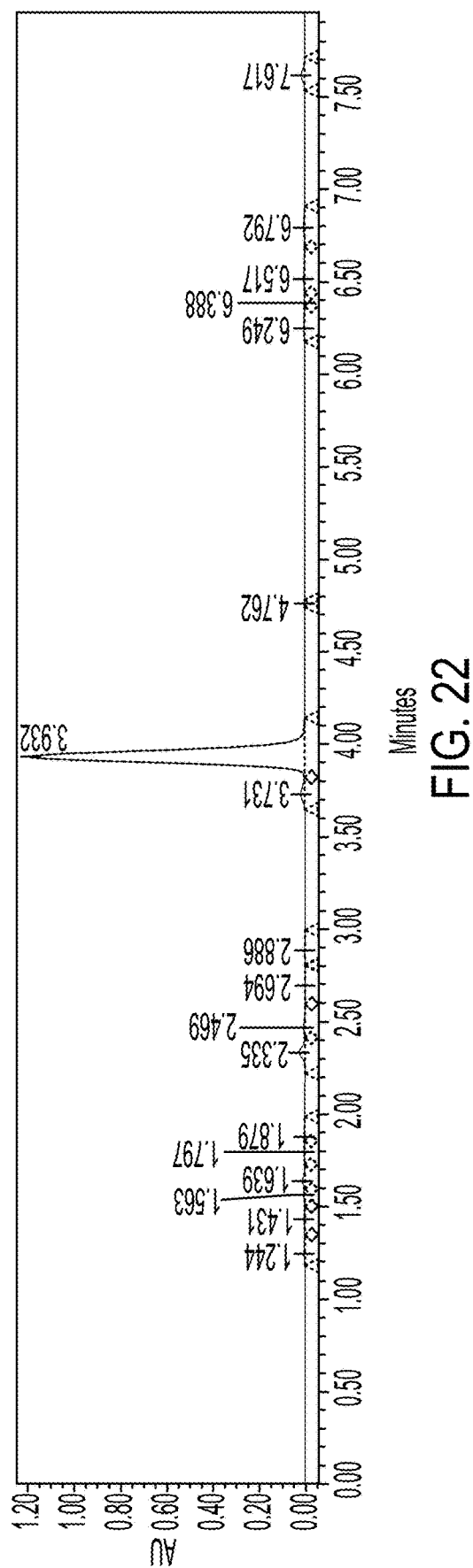
FIG. 22 depicts a HPLC chromatogram of the CBT reaction as described in Example 16.

HPLC of the CBC (91.10%) after drying overnight is shown in FIG. 22 and Table 19.

TABLE 19

|  | Retention Time | Area | % Area | Height |
|---|---|---|---|---|
| 1 | 1.244 | 28674 | 0.49 | 4747 |
| 2 | 1.431 | 27560 | 0.47 | 4124 |
| 3 | 1.563 | 21422 | 0.36 | 5033 |
| 4 | 1.639 | 41547 | 0.70 | 10720 |
| 5 | 1.797 | 16385 | 0.28 | 2677 |
| 6 | 1.879 | 10093 | 0.17 | 2158 |
| 7 | 2.335 | 98827 | 1.67 | 25460 |
| 8 | 2.469 | 28049 | 0.47 | 6300 |
| 9 | 2.694 | 888 | 0.02 | 132 |
| 10 | 2.886 | 7154 | 0.12 | 1638 |
| 11 | 3.731 | 91937 | 1.56 | 16866 |
| 12 | (CBC) 3.932 | 5381201 | 91.10 | 1190087 |
| 13 | 4.762 | 203 | 0.00 | 133 |
| 14 | 6.249 | 26760 | 0.45 | 3788 |
| 15 | 6.388 | 2341 | 0.04 | 714 |
| 16 | 6.517 | 27113 | 0.46 | 5762 |
| 17 | 6.792 | 31436 | 0.53 | 6264 |
| 18 | 7.617 | 65162 | 1.10 | 15810 |

Figure 23:
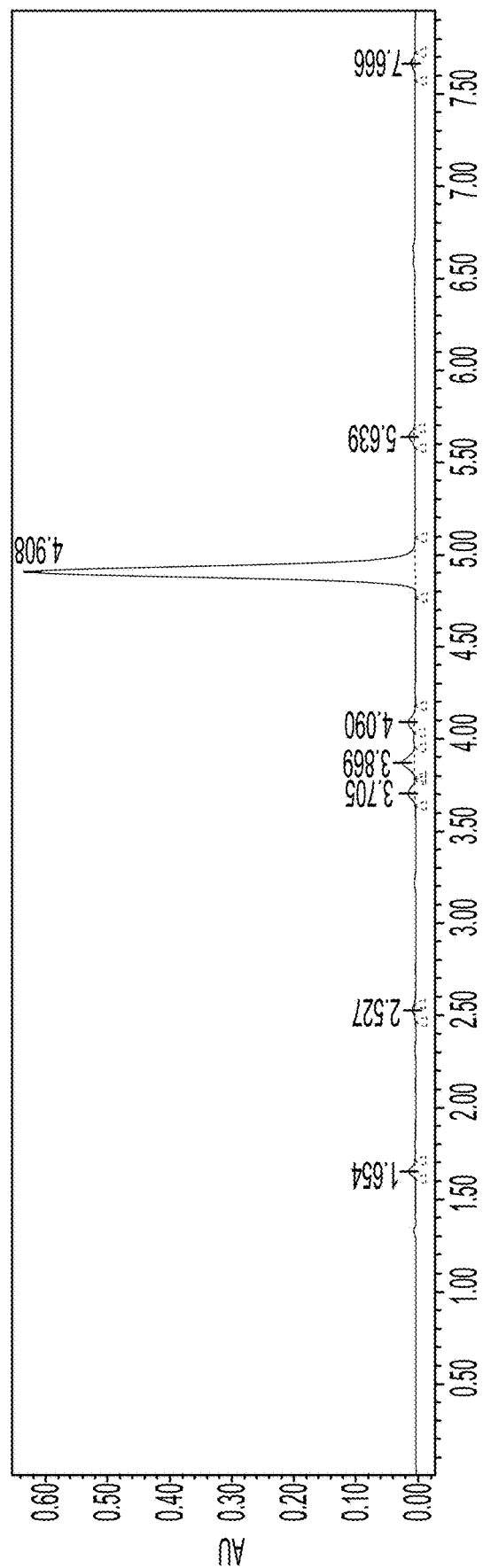
FIG. 23 depicts a HPLC chromatogram of the CBT reaction as described in Example 16.

First Distillation: A 500 mL round bottom flask was attached to a fractional column with a condenser and heated slowly to the temperatures described. The major fraction (see HPLC, FIG. 23 and Table 20) was collected at ~140 C under the oil pump vacuum (at ~0 mmbar).

TABLE 20

|  | Retention Time | Area | % Area | Height |
|---|---|---|---|---|
| 1 | 1.654 | 24144 | 0.81 | 8661 |
| 2 | 2.527 | 8070 | 0.27 | 2997 |
| 3 | 3.705 | 39506 | 1.33 | 9884 |
| 4 | 3.869 | 79235 | 2.66 | 18962 |
| 5 | 4.090 (CBC) | 35076 | 1.18 | 9127 |
| 6 | 4.908 (CBT) | 2745843 | 92.30 | 619988 |
| 7 | 5.639 | 23233 | 0.78 | 6990 |
| 8 | 7.666 | 19776 | 0.66 | 5227 |

Figure 24:
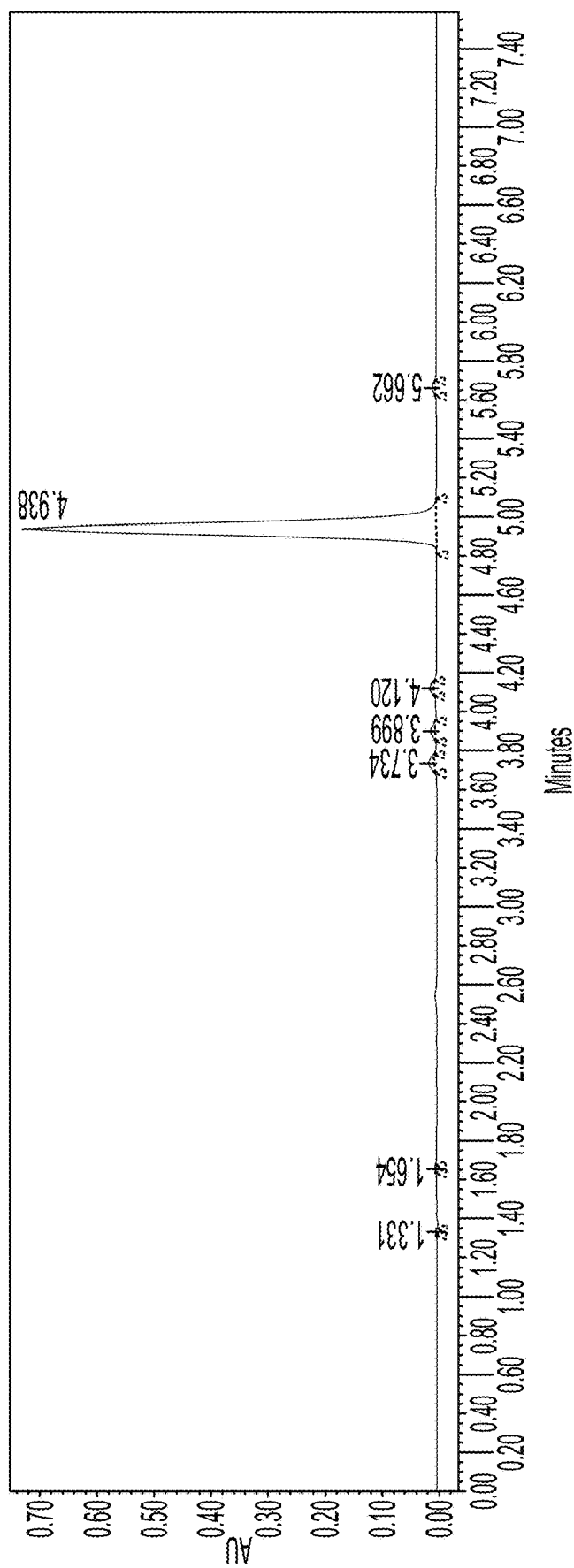
FIG. 24 depicts a HPLC chromatogram of the CBT reaction as described in Example 16.

Second Distillation: The material was re-distilled under the same conditions as the first distillation. 90 g CBT (97.03 area %, see HPLC, FIG. 24 and Table 21) was collected as the major fraction.

TABLE 21

|  | Retention Time | Area | % Area | Height |
|---|---|---|---|---|
| 1 | 1.331 | 1635 | 0.05 | 1321 |
| 2 | 1.654 | 1701 | 0.05 | 1128 |
| 3 | 3.734 | 32875 | 1.01 | 10122 |
| 4 | 3.899 | 27786 | 0.86 | 7836 |
| 5 | 4.120 (CBC) | 19005 | 0.59 | 6627 |

TABLE 21-continued

|  | Retention Time | Area | % Area | Height |
|---|---|---|---|---|
| 6 | 4.938 (CBT) | 3143207 | 97.03 | 712216 |
| 7 | 5.662 | 13156 | 0.41 | 4672 |

Figure 25:
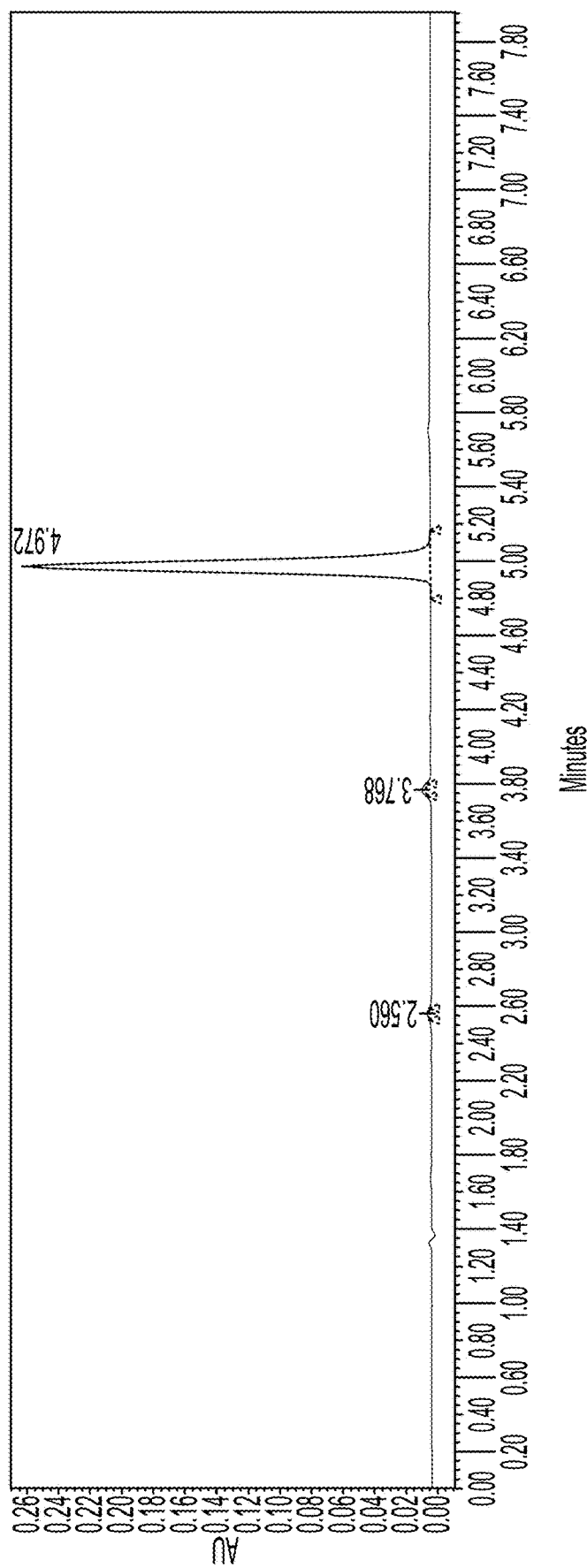
FIG. 25 depicts a HPLC chromatogram of the CBT reaction as described in Example 16.

Third Distillation: The 90 g CBT above (97.03 area %) was distilled again. 70 g CBT was collected as the major fraction. The Purity was 99.15% (see HPLC, area %, FIG. 25 and Table 22)

TABLE 22

|  | Retention Time | Area | % Area | Height |
|---|---|---|---|---|
| 1 | 2.560 | 2827 | 0.25 | 1282 |
| 2 | 3.768 | 6802 | 0.60 | 2756 |
| 3 | 4.972 (CBT) | 1122634 | 99.15 | 253908 |

Example 17: Citral Dosing Study A

Figure 26:
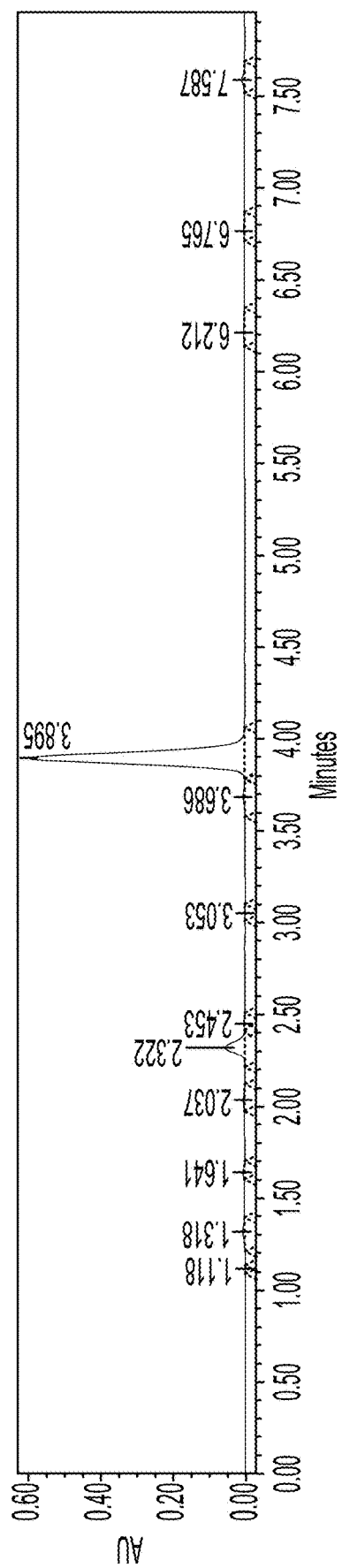
FIG. 26 depicts a HPLC chromatogram of the citral dosing experiments as described in Example 17.

An EasyMax reactor (50 mL) equipped with a reflux condenser was loaded with olivetol (2.70 g, 15.0 mmol, 1.00 equiv.), Toluene (33 mL), and ethylenediamine (200 µL, 3.00 mmol, 20 mol %). Then the solution was heated to 100° C. (Note: The reaction turned cloudy when ethylenediamine was added. The solution turned clear while heating to 100° C. Citral (2.80 mL, 16.35 mmol, 1.09 equiv.) in Toluene (8.17 mL) was added over a ten-minute period. (Note: The reaction bubbled during this time.) The reaction mixture was stirred at 100° C. for 30 minutes (Note: The reaction was no longer bubbling after ~5 minutes.). After the allotted time, the reaction mixture was cooled to 20° C. HPLC is shown in FIG. 26 and Table 23.

TABLE 23

|  | Retention Time | Area | % Area | Height |
|---|---|---|---|---|
| 1 | 1.118 | 54 | 0.00 | 35 |
| 2 | 1.318 | 29003 | 0.95 | 6523 |
| 3 | 1.641 | 14370 | 0.47 | 5350 |
| 4 | 2.037 | 12588 | 0.41 | 3379 |
| 5 | 2.322 | 218824 | 7.21 | 54751 |
| 6 | 2.453 | 7742 | 0.25 | 2174 |
| 7 | 3.053 | 169 | 0.01 | 70 |
| 8 | 3.686 | 22107 | 0.73 | 4798 |
| 9 | (CBC) 3.895 | 2677302 | 88.15 | 595727 |
| 10 | 6.212 | 14642 | 0.48 | 2264 |
| 11 | 6.765 | 12187 | 0.40 | 2353 |
| 12 | 7.587 | 28100 | 0.93 | 6828 |

Example 18: Citral Dosing Study B

Figure 27:
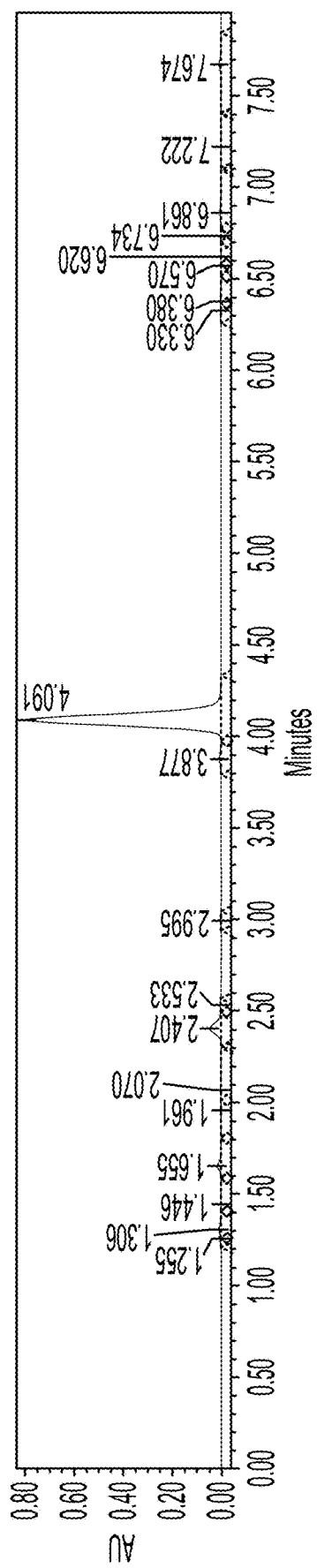
FIG. 27 depicts a HPLC chromatogram of the citral dosing studies as described in Example 18.

An EasyMax reactor (50 mL) equipped with a reflux condenser was loaded with olivetol (2.70 g, 15.0 mmol, 1.00 equiv.), Toluene (33 mL), and ethylenediamine (200 µL, 3.00 mmol, 20 mol %). Then the solution was heated to 100° C. (Note: The reaction turned cloudy when ethylenediamine was added. The solution turned clear while heating to 100° C.) Citral (2.57 mL, 15.00 mmol, 1.00 equiv.) in Toluene (7.35 mL) was added over a ten-minute period. (Note: The reaction bubbled during this time.) The reaction mixture was stirred at 100° C. for 30 minutes (Note: The reaction was no longer bubbling after ~5 minutes.). After the allotted time, the reaction mixture was cooled to 20° C. HPLC is shown in FIG. 27 and Table 24.

TABLE 24

| | Retention Time | Area | % Area | Height |
|---|---|---|---|---|
| 1 | 1.255 | 7981 | 0.20 | 3841 |
| 2 | 1.306 | 32144 | 0.81 | 7272 |
| 3 | 1.446 | 7681 | 0.19 | 873 |
| 4 | 1.655 | 50423 | 1.28 | 15679 |
| 5 | 1.961 | 11907 | 0.30 | 1827 |
| 6 | 2.070 | 9478 | 0.24 | 1806 |
| 7 | 2.407 | 185206 | 4.69 | 45501 |
| 8 | 2.533 | 5139 | 0.13 | 1864 |
| 9 | 2.995 | 5664 | 0.14 | 1596 |
| 10 | 3.877 | 30790 | 0.78 | 6535 |
| 11 | (CBC) 4.091 | 3535125 | 89.53 | 792499 |
| 12 | 6.330 | 7775 | 0.20 | 1718 |
| 13 | 6.380 | 5915 | 0.15 | 1559 |
| 14 | 6.570 | 854 | 0.02 | 334 |
| 15 | 6.620 | 2079 | 0.05 | 432 |
| 16 | 6.734 | 619 | 0.02 | 165 |
| 17 | 6.861 | 16883 | 0.43 | 3014 |
| 18 | 7.222 | 2103 | 0.05 | 356 |
| 19 | 7.674 | 30785 | 0.78 | 6907 |

Example 19: Citral Dosing Study C

Figure 28:
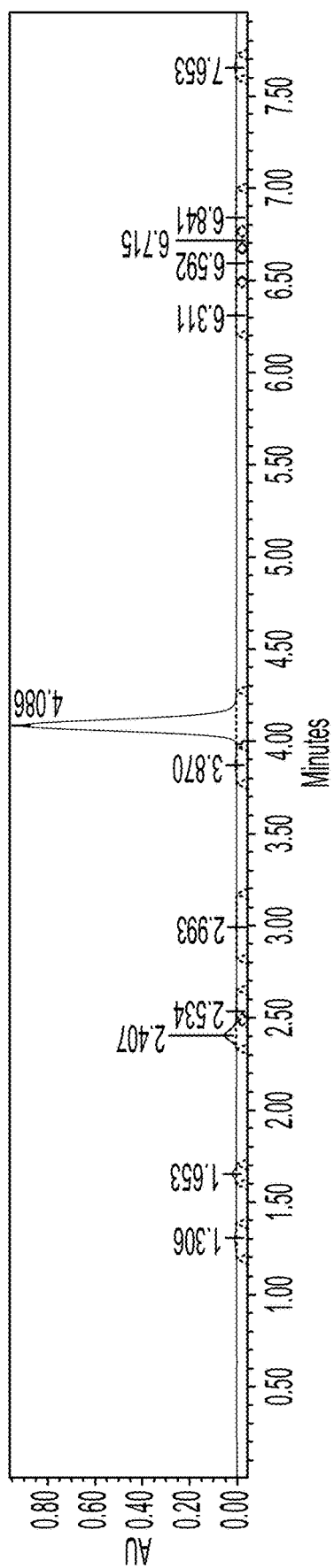
FIG. 28 depicts a HPLC chromatogram of the citral dosing studies described in Example 19.

An EasyMax reactor (50 mL) equipped with a reflux condenser was loaded with olivetol (2.70 g, 15.0 mmol, 1.00 equiv.), Toluene (33 mL), and ethylenediamine (200 μL, 3.00 mmol, 20 mol %). Then the solution was heated to 100° C. (Note: The reaction turned cloudy when ethylenediamine was added. The solution turned clear while heating to 100° C.) Next, citral (2.44 mL, 14.25 mmol, 0.95 equiv.) in Toluene (6.98 mL) was added over a ten-minute period. (Note: The reaction bubbled during this time.) The reaction mixture was stirred at 100° C. for 30 minutes (Note: The reaction was no longer bubbling after ~5 minutes.). After the allotted time, the reaction mixture was cooled to 20° C. Purification of reaction mixture by FCC on the Buchi using the CBC method. The crude reaction mixture was purified by FCC. The pure fractions were combined, and solvent was removed by rotary evaporation to give 4.13 g of a light-yellow crude oil. HPLC is shown in FIG. 28 and Table 25.

TABLE 25

| | Retention Time | Area | % Area | Height |
|---|---|---|---|---|
| 1 | 1.306 | 43170 | 0.97 | 8391 |
| 2 | 1.653 | 46550 | 1.04 | 16329 |
| 3 | 2.407 | 192383 | 4.31 | 49453 |
| 4 | 2.534 | 19063 | 0.43 | 4303 |
| 5 | 2.993 | 9310 | 0.21 | 2035 |
| 6 | 3.870 | 34431 | 0.77 | 7443 |
| 7 | (CBC) 4.086 | 4047071 | 90.64 | 909862 |
| 8 | 6.311 | 19262 | 0.43 | 2357 |
| 9 | 6.592 | 4034 | 0.09 | 537 |
| 10 | 6.715 | 1280 | 0.03 | 250 |
| 11 | 6.841 | 19497 | 0.44 | 3554 |
| 12 | 7.653 | 28880 | 0.65 | 7463 |

Example 20: Citral Dosing Study D

Figure 29:
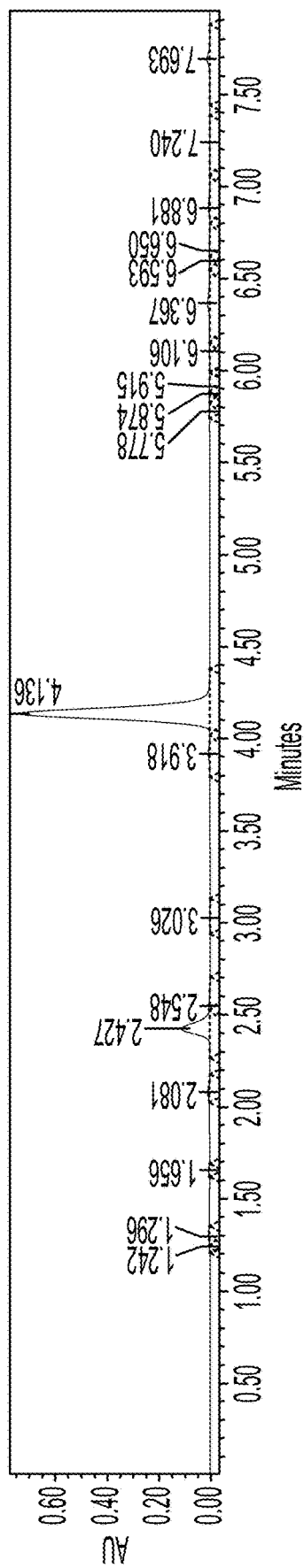
FIG. 29 depicts a HPLC chromatogram of the citral dosing studies described in Example 20.

An EasyMax reactor (50 mL) equipped with a reflux condenser was loaded with olivetol (2.70 g, 15.0 mmol, 1.00 equiv.), Toluene (33 mL), and ethylenediamine (200 μL, 3.00 mmol, 20 mol %). Then the solution was heated to 100° C. (Note: The reaction turned cloudy when ethylenediamine was added. The solution turned clear while heating to 100° C.) Next, citral (3.03 mL, 17.7 mmol, 1.18 equiv.) in Toluene (8.67 mL) was added over a ten-minute period. (Note: The reaction bubbled during this time.) The reaction mixture was stirred at 100° C. for 30 minutes (Note: The reaction was no longer bubbling after ~5 minutes.). After the allotted time, the reaction mixture was cooled to 20° C. HPLC is shown in FIG. 29 and Table 26.

TABLE 26

| | Retention Time | Area | % Area | Height |
|---|---|---|---|---|
| 1 | 1.242 | 1379 | 0.03 | 858 |
| 2 | 1.296 | 13808 | 0.35 | 3933 |
| 3 | 1.656 | 7561 | 0.19 | 3080 |
| 4 | 2.081 | 17947 | 0.45 | 4954 |
| 5 | 2.427 | 469128 | 11.82 | 112003 |
| 6 | 2.548 | 15120 | 0.38 | 3605 |
| 7 | 3.026 | 4679 | 0.12 | 1004 |
| 8 | 3.918 | 27397 | 0.69 | 5794 |
| 9 | (CBC) 4.136 | 3277468 | 82.56 | 735894 |
| 10 | 5.778 | 966 | 0.02 | 280 |
| 11 | 5.874 | 674 | 0.02 | 216 |
| 12 | 5.915 | 948 | 0.02 | 245 |
| 13 | 6.106 | 1284 | 0.03 | 219 |
| 14 | 6.367 | 50783 | 1.28 | 7598 |
| 15 | 6.593 | 2508 | 0.06 | 661 |
| 16 | 6.650 | 5010 | 0.13 | 705 |
| 17 | 6.881 | 25134 | 0.63 | 4427 |
| 18 | 7.240 | 2147 | 0.05 | 240 |
| 19 | 7.693 | 45948 | 1.16 | 10436 |

Example 21: Citral Dosing Study E

Figure 30:
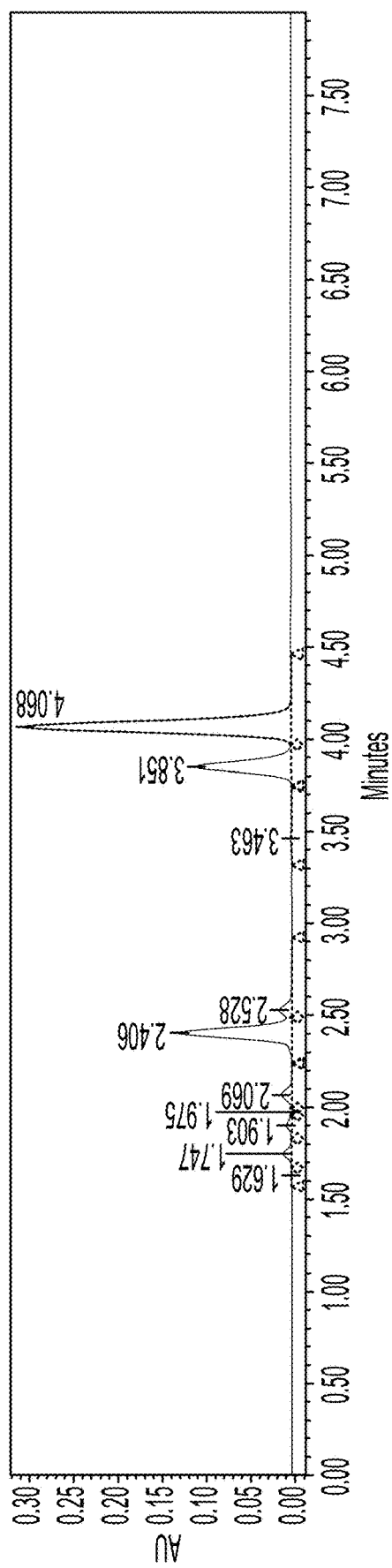
FIG. 30 depicts a HPLC chromatogram of the citral dosing studies described in Example 21.
Figure 31:
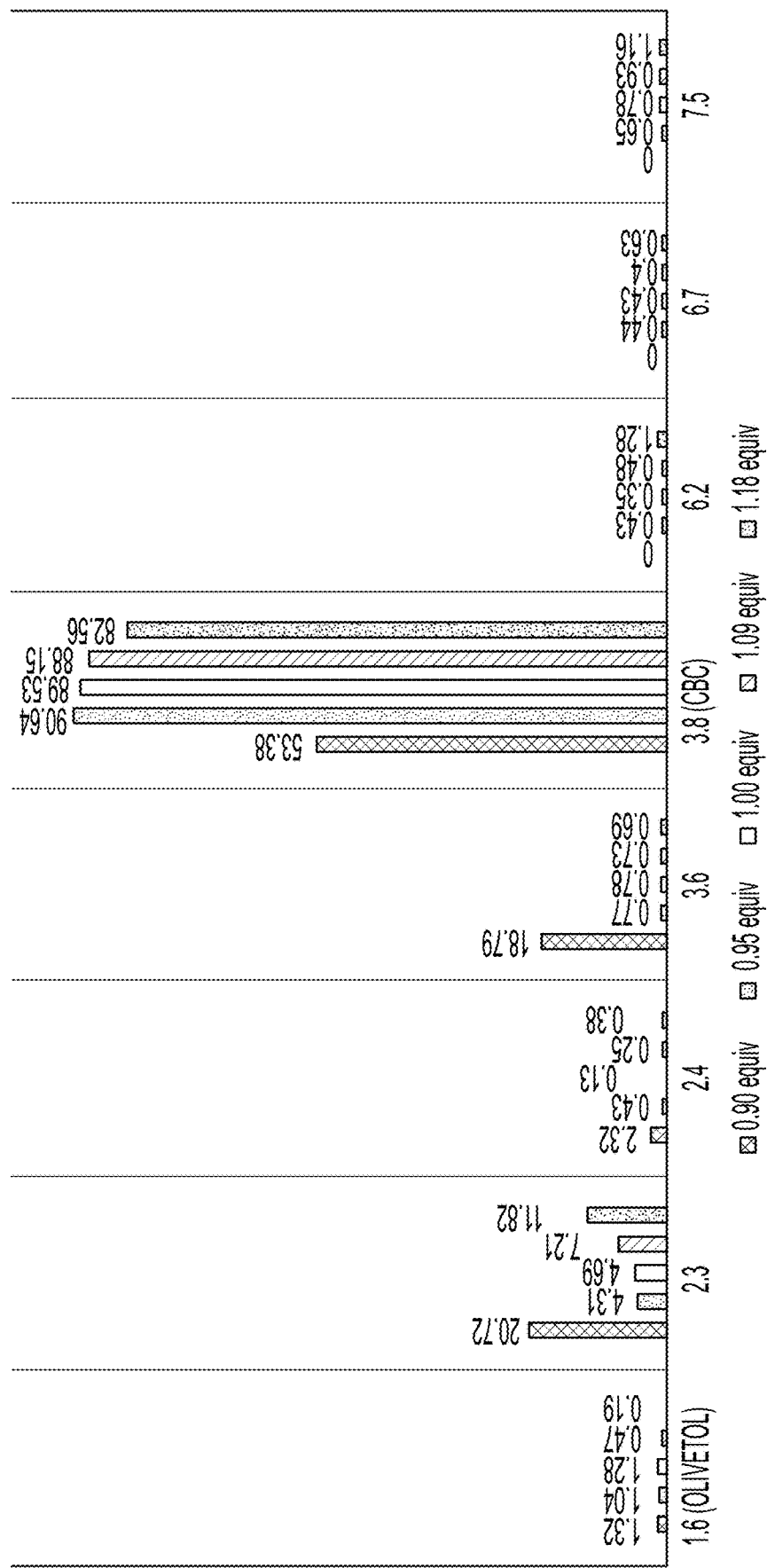
FIG. 31 is a histogram of the data for citral loading to CBC conversion.

An EasyMax reactor (50 mL) equipped with a reflux condenser was loaded with olivetol (2.70 g, 15.0 mmol, 1.00 equiv.), Toluene (33 mL), and ethylenediamine (200 μL, 3.00 mmol, 20 mol %). Then the solution was heated to 100° C. (Note: The reaction turned cloudy when ethylenediamine was added. The solution turned clear while heating to 100° C.) Next, citral (2.34 mL, 13.5 mmol, 0.90 equiv.) in Toluene (6.61 mL) was added over a ten-minute period. (Note: The reaction bubbled during this time.) The reaction mixture was stirred at 100° C. for 30 minutes (Note: The reaction was no longer bubbling after ~5 minutes.). After the allotted time, the reaction mixture was cooled to 20° C. HPLC is shown in FIG. 30 and Table 27. FIG. 31 shows the data for the citral dosing studies.

TABLE 27

| | Retention Time | Area | % Area | Height |
|---|---|---|---|---|
| 1 | 1.629 | 2307 | 0.09 | 735 |
| 2 | 1.747 | 33133 | 1.32 | 9426 |
| 5 | 1.903 | 23198 | 0.92 | 6263 |
| 4 | 1.975 | 3775 | 0.15 | 1616 |
| 5 | 2.069 | 50229 | 1.99 | 11776 |
| 6 | 2.406 | 521724 | 20.72 | 128034 |
| 7 | 2.528 | 58504 | 2.32 | 14654 |
| 8 | 3.463 | 7972 | 0.32 | 1317 |
| 9 | 3.851 | 473281 | 18.79 | 107947 |
| 10 | (CBC) 4.068 | 1344284 | 53.38 | 302611 |

Example 22: Temperature Study A

An EasyMax reactor (50 mL) equipped with a reflux condenser was loaded with olivetol (2.70 g, 15.0 mmol, 1.00 equiv.), Toluene (33 mL), and ethylenediamine (200 μL, 3.00 mmol, 20 mol %). Then the solution was heated to 100°

Figure 32:
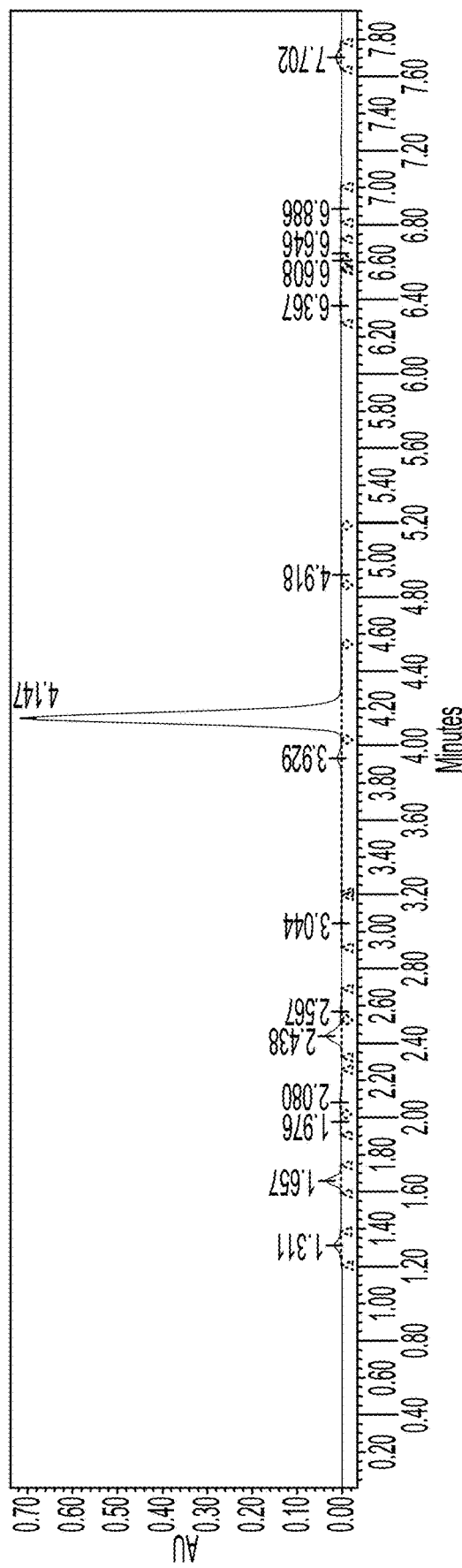
FIG. 32 depicts a HPLC chromatogram of the temperature studies described in Example 22.

C. (Note: The reaction turned cloudy when ethylenediamine was added. The solution turned clear while heating to 80° C.) Next, citral (2.57 mL, 15.00 mmol, 1.00 equiv.) in Toluene (7.35 mL) was added over a ten-minute period. (Note: The reaction bubbled during this time.) The reaction mixture was stirred at 80° C. for 30 minutes (Note: The reaction was no longer bubbling after ~5 minutes.). After the allotted time, the reaction mixture was cooled to 20° C. HPLC is shown in FIG. 32 and Table 28.

TABLE 28

|  | Retention Time | Area | % Area | Height |
|---|---|---|---|---|
| 1 | 1.311 | 56990 | 1.56 | 14609 |
| 2 | 1.657 | 97382 | 2.67 | 32040 |
| 3 | 1.976 | 5983 | 0.16 | 1539 |
| 4 | 2.080 | 14300 | 0.39 | 3277 |
| 5 | 2.438 | 144343 | 3.96 | 33626 |
| 6 | 2.567 | 14557 | 0.40 | 2927 |
| 7 | 3.044 | 8906 | 0.24 | 1895 |
| 8 | 3.929 | 54273 | 1.49 | 8908 |
| 9 | (CBC) 4.147 | 3156518 | 86.50 | 703347 |
| 10 | 4.918 | 16796 | 0.46 | 1095 |
| 11 | 6.367 | 15895 | 0.44 | 1981 |
| 12 | 6.608 | 1568 | 0.04 | 817 |
| 13 | 6.646 | 4164 | 0.11 | 1061 |
| 14 | 6.886 | 11861 | 0.33 | 2063 |
| 15 | 7.702 | 45517 | 1.25 | 11430 |

Example 23: Temperature Study B

Figure 33:
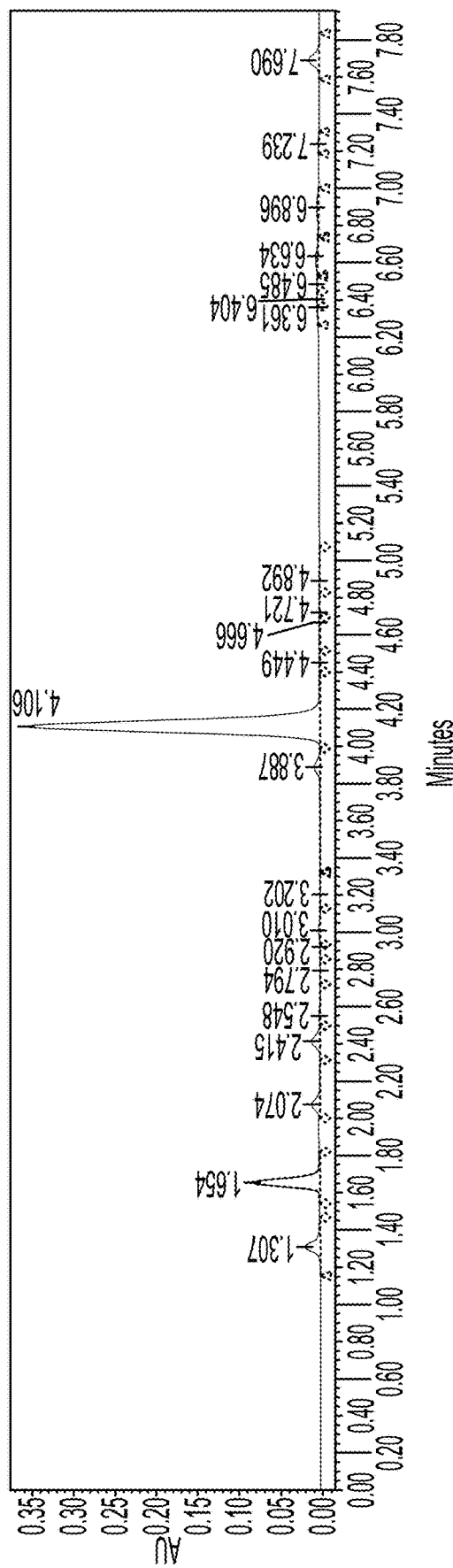
FIG. 33 depicts a HPLC chromatogram of the temperature studies described in Example 23.
Figure 34:
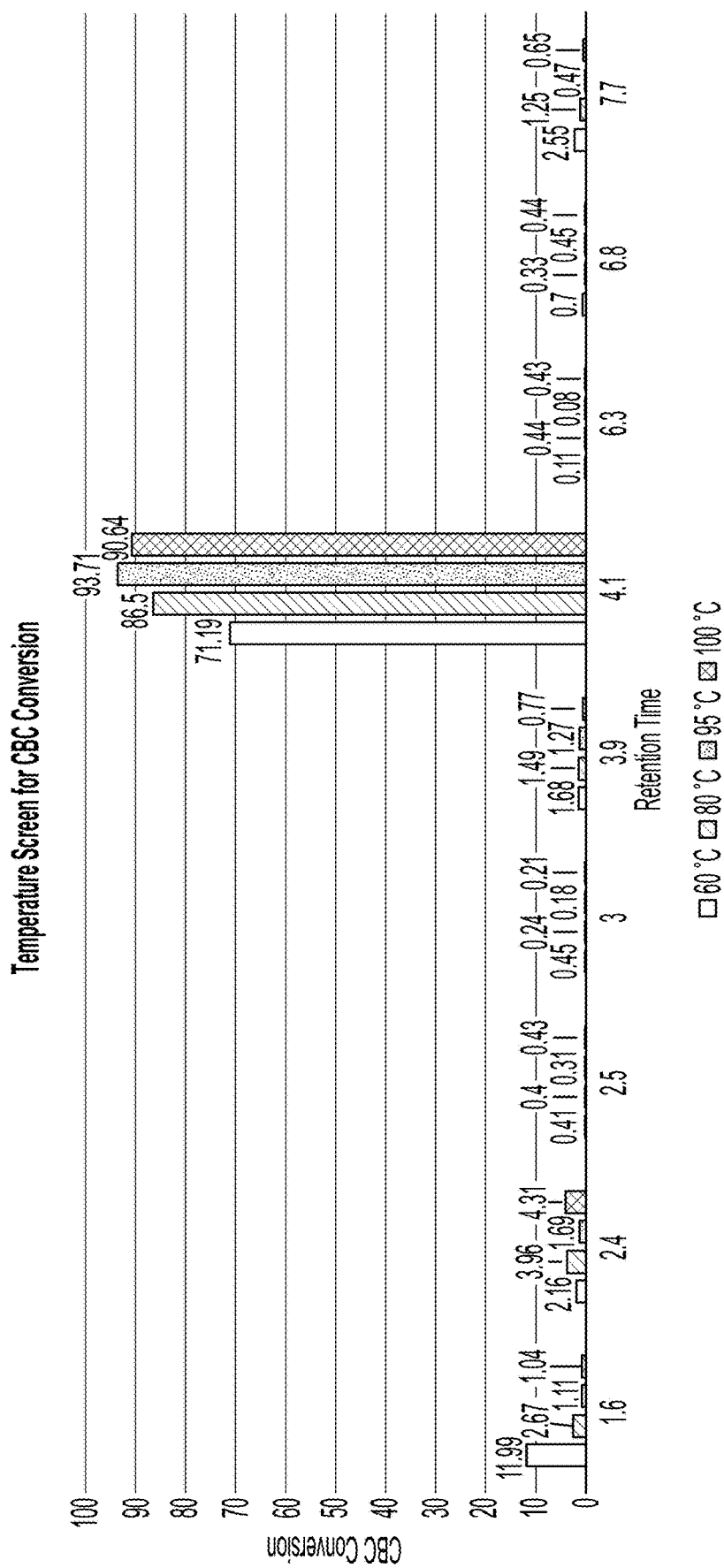
FIG. 34 is a histogram of the data for the temperature screen studies.

An EasyMax reactor (50 mL) equipped with a reflux condenser was loaded with olivetol (2.70 g, 15.0 mmol, 1.00 equiv.), Toluene (33 mL), and ethylenediamine (200 µL, 3.00 mmol, 20 mol %). Then the solution was heated to 100° C. (Note: The reaction turned cloudy when ethylenediamine was added. The solution turned clear while heating to 60° C.) Next, citral (2.57 mL, 15.00 mmol, 1.00 equiv.) in Toluene (7.35 mL) was added over a ten-minute period. (Note: The reaction turned cloudy during and after addition of diluted citral. After 10 minutes the solution was no longer cloudy and was a clear orange.) The reaction mixture was stirred at 60° C. for 30 minutes (Note: The reaction did not bubble.). After the allotted time, the reaction mixture was cooled to 20° C. HPLC is shown in FIG. 33 and Table 29. FIG. 34 shows the data for the temperature screen.

TABLE 29

|  | Retention Time | Area | % Area | Height |
|---|---|---|---|---|
| 1 | 1.307 | 81944 | 3.67 | 18735 |
| 2 | 1.654 | 267524 | 11.99 | 82072 |
| 3 | 2.074 | 55636 | 2.49 | 10710 |
| 4 | 2.415 | 48093 | 2.16 | 10653 |
| 5 | 2.548 | 9166 | 0.41 | 1580 |
| 6 | 2.794 | 1259 | 0.06 | 204 |
| 7 | 2.920 | 1141 | 0.05 | 319 |
| 8 | 3.010 | 9976 | 0.45 | 1995 |
| 9 | 3.202 | 1419 | 0.06 | 335 |
| 10 | 3.887 | 37392 | 1.68 | 6938 |
| 11 | (CBC) 4.106 | 1588613 | 71.19 | 354542 |
| 12 | 4.449 | 4760 | 0.21 | 758 |
| 13 | 4.666 | 9292 | 0.42 | 1053 |
| 14 | 4.721 | 6916 | 0.31 | 1070 |
| 15 | 4.892 | 9320 | 0.42 | 981 |
| 16 | 6.361 | 2363 | 0.11 | 927 |
| 17 | 6.404 | 4409 | 0.20 | 1220 |
| 18 | 6.485 | 2728 | 0.12 | 938 |
| 19 | 6.634 | 14431 | 0.65 | 2638 |

TABLE 29-continued

|  | Retention Time | Area | % Area | Height |
|---|---|---|---|---|
| 20 | 6.896 | 15704 | 0.70 | 2109 |
| 21 | 7.239 | 2669 | 0.12 | 735 |
| 22 | 7.690 | 56843 | 2.55 | 13083 |

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

Citation or identification of any reference in this application is not an admission that such reference is available as prior art.

Efforts have been made to ensure accuracy with respect to numbers used (e.g. amounts, temperature, etc.) but some experimental errors and deviations should be accounted for.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller ranges is also encompassed, subject to any specifically excluded limit in the stated range. Where the stated range includes one or both of the limits, ranges excluding either or both of those included limits are also included.

Unless defined otherwise, technical and scientific terms used herein have the same meaning as commonly understood by one of ordinary skill in the art to which this subject matter belongs, and are consistent with: Singleton et al (1994) Dictionary of Microbiology and Molecular Biology, 2nd Ed., J. Wiley & Sons, New York, NY; and Janeway, C., Travers, P., Walport, M., Shlomchik (2001) Immunobiology, 5th Ed., Garland Publishing, New York.

The disclosures of all cited references including publications, patents, and patent applications are expressly incorporated herein by reference in their entirety.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation. One skilled in the art will recognize many methods and materials similar or equivalent to those described herein, which could be used in the practicing the subject matter described herein. The present disclosure is in no way limited to just the methods and materials described.

The invention claimed is:

1. A method of preparing a compound of Formula I or II,

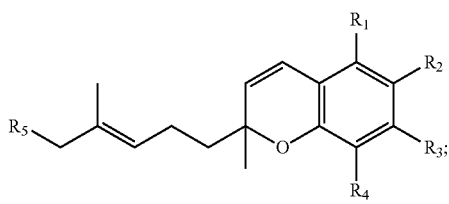

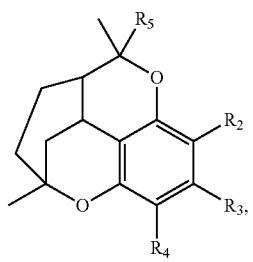

wherein,
R₁ is selected from the group consisting of hydroxyl and C$_{1-5}$alkoxy;
R₂ and R₄ are in each instance independently selected from the group consisting of hydrogen, —C$_{1-5}$alkyl, —CF₃, cyano, nitro, phenyl, —C(O)R₆, —NR$_a$R$_b$, —C(O)OR₆, —O—C(O)R₆, —O—R₆, —O—R₆, —C(H)=C(R₆)₂, —N(H)C(O)R₆, halo, —N(R₆)₃;
wherein, R$_a$ and R$_b$ are each independently hydrogen or C$_{1-5}$alkyl;
wherein, R₆ is hydrogen or C$_{1-5}$alkyl;
R₃ is selected from the group consisting of hydrogen, linear or branched C$_{1-10}$alkyl;
R₅ is selected from the group consisting of hydrogen, C$_{1-5}$alkyl, C$_{1-5}$alkenyl and prenyl;
comprising:
dosing at a first temperature above 65° C. a compound of Formula Ia

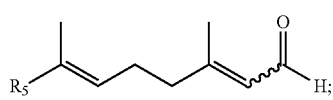

wherein, R₅ is as described above;
to a first mixture, said first mixture comprising an amine and a compound of Formula Ib

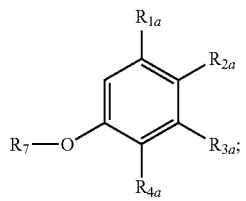

wherein,
R$_{1a}$ is selected from the group consisting of hydroxyl and C$_{1-5}$alkoxy;
R$_{2a}$ and R$_{4a}$ are each as described above for R₂ and R₄;
R$_{3a}$ is selected from the group consisting of hydrogen, linear or branched C$_{1-10}$alkyl; and
R₇ is selected from the group consisting of hydrogen, —C(O)R$_c$,
wherein R$_c$ is hydrogen or C$_{1-5}$alkyl;
to form a second mixture; and,
allowing the second mixture to react at a second temperature;
wherein, a compound of Formula I or II is prepared.

2. The method of claim 1, wherein R₁ is hydroxyl.

3. The method of claim 1, wherein R₃ is branched or linear C$_{3-10}$ alkyl.

4. The method of claim 1, wherein the compound of Formula Ib has the formula:

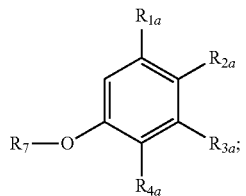

wherein,
R$_{1a}$ is selected from the group consisting of hydroxyl and C$_{1-5}$alkoxy;
R$_{3a}$ is selected from the group consisting of hydrogen, linear or branched C$_{1-10}$alkyl; and
R₇ is selected from the group consisting of hydrogen, —C(O)R$_c$, wherein R$_c$ is hydrogen or C$_{1-5}$alkyl.

5. The method of claim 4, wherein
R$_{1a}$ is hydroxyl or C$_{1-5}$alkoxy;
R$_{3a}$ is a linear C$_{1-10}$alkyl; and
R₇ is selected from the group consisting of hydrogen, —C(O)R$_c$,
wherein R$_c$ is hydrogen or C$_{1-5}$alkyl.

6. The method of claim 5, wherein the compound of Formula Ib is:

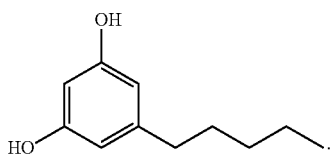

7. The method of claim 1, wherein the compound of Formula Ia is:

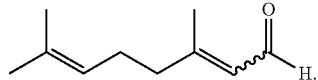

8. The method of claim 1, wherein the dosing at a first temperature above 65° C. a compound of Formula Ia comprises contacting about 0.8 to about 1.3 molar equivalents of a compound of Formula Ia to a compound of Formula Ib.

9. The method of claim 1, wherein the dosing at a first temperature above 65° C. a compound of Formula Ia comprises contacting about 0.95 to about 1.09 molar equivalents of a compound of Formula Ia to a compound of Formula Ib.

10. The method of claim 1, wherein the second temperature is from about 70° C. to about 200° C.

11. The method of claim 1, further comprising after the allowing the second mixture to react at a second temperature, separating an organic layer to collect an organic phase.

12. The method of claim 11, further comprising distilling the organic phase to prepare a purified compound of Formula II.

13. The method of claim 11, further comprising contacting the organic phase with chromatographic media and collecting fractions containing a compound of Formula I.

14. The method of claim 13, wherein the compound of Formula I has the structure:

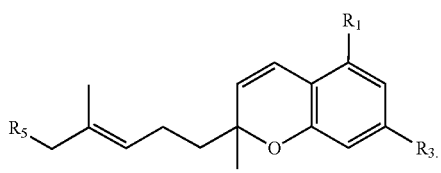

15. The method of claim 14, wherein the compound of Formula I has the structure:

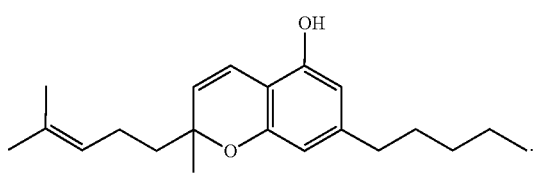

16. The method of claim 1, for preparing a compound of Formula I,

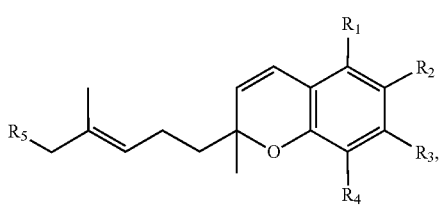

wherein,
$R_1$ is selected from the group consisting of hydroxyl and $C_{1-5}$alkoxy;

$R_2$ and $R_4$ are in each instance independently selected from the group consisting of hydrogen, —$C_{1-5}$alkyl, —$CF_3$, cyano, nitro, phenyl, (O)$R_6$, —$NR_aR_b$, —C(O)O$R_6$, —O—C(O)$R_6$, —O—$R_6$, —O—$R_6$, —C(H)=C($R_6$)$_2$, —N(H)C(O)$R_6$, halo, —N($R_6$)$_3$;

wherein, $R_a$ and $R_b$ are each independently hydrogen or $C_{1-5}$alkyl;

wherein, $R_6$ is hydrogen or $C_{1-5}$alkyl;

$R_3$ is selected from the group consisting of hydrogen, linear or branched $C_{1-10}$alkyl;

$R_5$ is selected from the group consisting of hydrogen, $C_{1-5}$alkyl, $C_{1-5}$ alkenyl and prenyl;

comprising:
dosing at a first temperature above 65° C. a compound of Formula Ia

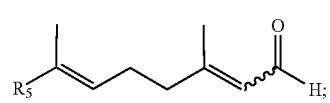

wherein, $R_5$ is as described above;
to a first mixture, said first mixture comprising an amine and a compound of Formula Ib

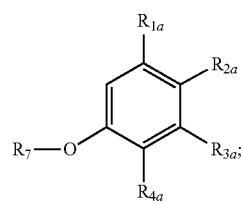

wherein,
$R_{1a}$ is selected from the group consisting of hydroxyl and $C_{1-5}$alkoxy;

$R_{2a}$ and $R_{4a}$ are each as described above for $R_2$ and $R_4$;

$R_{3a}$ is selected from the group consisting of hydrogen, linear or branched $C_{1-10}$alkyl; and $R_7$ is selected from the group consisting of hydrogen, —C(O)$R_c$, wherein $R_c$ is hydrogen or $C_{1-5}$alkyl;

to form a second mixture;

allowing the second mixture to react at a second temperature;

separating an organic layer to collect an organic phase;

contacting the organic phase with chromatographic media;

eluting and collecting an eluate;

distilling the eluate;

wherein, a compound of Formula I is prepared.

17. The method of claim 16, wherein the compound of Formula I is:

the compound of Formula Ia is:

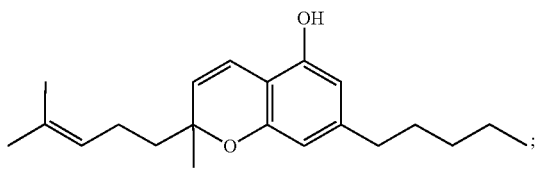

and, the compound of Formula Ib is:

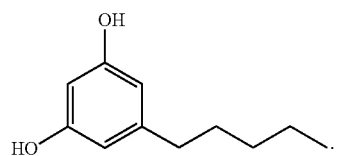

18. The method of claim 1, for preparing a compound of Formula II,

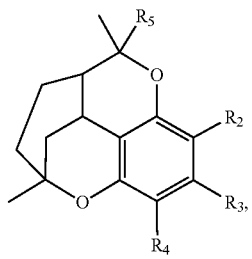

wherein,
R$_2$ and R$_4$ are in each instance independently selected from the group consisting of hydrogen, —C$_{1-5}$alkyl, —CF$_3$, cyano, nitro, phenyl, —C(O)R$_6$, —NR$_a$R$_b$, —C(O)OR$_6$, —O—C(O)R$_6$, —O—R$_6$, —O—R$_6$, —C(H)=C(R)$_2$, —N(H)C(O)R$_6$, halo, —N(R$_6$)$_3$;
wherein, R$_a$ and R$_b$ are each independently hydrogen or C$_{1-5}$alkyl;
wherein, R$_6$ is hydrogen or C$_{1-5}$alkyl;
R$_3$ is selected from the group consisting of hydrogen, linear or branched C$_{1-10}$alkyl;
R$_5$ is selected from the group consisting of hydrogen, C$_{1-5}$alkyl, C$_{1-5}$alkenyl and prenyl;
comprising:
dosing at a first temperature above 65° C. a compound of Formula Ia

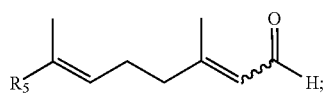

wherein, R$_5$ is as described above;
to a first mixture, said first mixture comprising an amine and a compound of Formula Ib

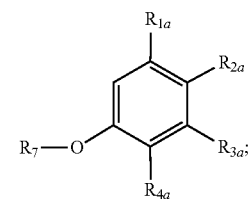

wherein,
R$_{1a}$ is selected from the group consisting of hydroxyl and C$_{1-5}$alkoxy;
R$_{2a}$ and R$_{4a}$ are each as described above for R$_2$ and R$_a$;
R$_{3a}$ is selected from the group consisting of hydrogen, linear or branched C$_{1-10}$alkyl; and
R$_7$ is selected from the group consisting of hydrogen, —C(O)R$_c$,
wherein R$_c$ is hydrogen or C$_{1-5}$alkyl;
to form a second mixture;
allowing the second mixture to react at a second temperature;
separating an organic layer to prepare an organic phase;
distilling the organic phase;
wherein, a compound of Formula II is prepared.

19. The method of claim 18, wherein the compound of Formula II is:

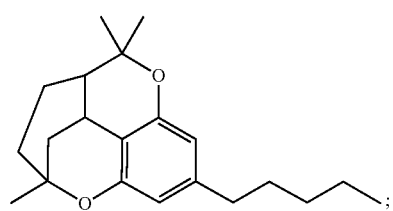

the compound of Formula Ia is:

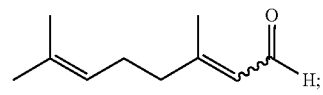

and, the compound of Formula Ib is:

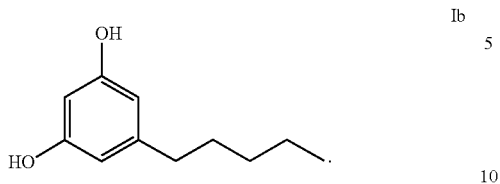

20. The method of claim 1, wherein $R_2$ and $R_4$ are in each instance independently selected from the group consisting of hydrogen, cyano, —C(O)OR$_6$, and halo,
 wherein, $R_6$ is hydrogen or $C_{1-5}$alkyl.
21. The method of claim 20, $R_6$ is hydrogen.
22. The method of claim 21, wherein $R_2$ is —C(O)OH and $R_4$ is hydrogen.
23. The method of claim 1, wherein $R_3$ and $R_{3a}$ are each propyl, butyl or pentyl.
24. The method of claim 12, wherein said method does not comprise a chromatographic purification.

\* \* \* \* \*

UNITED STATES PATENT AND TRADEMARK OFFICE
CERTIFICATE OF CORRECTION

PATENT NO. : 12,269,810 B2
APPLICATION NO. : 17/997597
DATED : April 8, 2025
INVENTOR(S) : Wen-Chun Zhang et al.

Page 1 of 1

It is certified that error appears in the above-identified patent and that said Letters Patent is hereby corrected as shown below:

On the Title Page

In Column 1, item (72), Inventors, Line 2, delete "P" and insert -- P. --, therefor.

In the Claims

In Column 54, Line 28, Claim 3, delete "$C_{3-10}$ alkyl." and insert -- $C_{3-10}$alkyl. --, therefor.
In Column 56, Line 6, Claim 16, delete "(O)$R_6$," and insert -- —C(O)$R_6$, --, therefor.
In Column 56, Line 7, Claim 16, delete "—O—$R_6$, —O—$R_6$," and insert -- —O—$R_6$, --, therefor.
In Column 56, Line 16, Claim 16, delete "$C_{1-5}$ alkenyl" and insert -- $C_{1-5}$alkenyl --, therefor.
In Column 57, Line 54, Claim 18, delete "—O—$R_6$, —O—$R_6$," and insert -- —O—$R_6$, --, therefor.
In Column 57, Line 55, Claim 18, delete "—C(H)=C(R)$_2$," and insert -- —C(H)=C($R_6$)$_2$, --, therefor.
In Column 58, Line 29, Claim 18, delete "$R_a$;" and insert -- $R_4$; --, therefor.

Signed and Sealed this
Eighteenth Day of November, 2025

John A. Squires
*Director of the United States Patent and Trademark Office*